US010202614B2

(12) United States Patent
Brandizzi et al.

(10) Patent No.: US 10,202,614 B2
(45) Date of Patent: Feb. 12, 2019

(54) DIGESTIBILITY OF PLANT BIOMASS

(71) Applicants: Ohio University, Athens, OH (US); Board of Trustees of Michigan State University, East Lansing, MI (US)

(72) Inventors: Federica Brandizzi, East Lansing, MI (US); Curtis Wilkerson, Swartz Creek, MI (US); Sang Jin Kim, Okemos, MI (US); Michael Held, Athens, OH (US)

(73) Assignee: Board of Trustees of Michigan State University, East Lansing, MI (US)

( * ) Notice: Subject to any disclaimer, the term of this patent is extended or adjusted under 35 U.S.C. 154(b) by 47 days.

(21) Appl. No.: 14/901,904

(22) PCT Filed: Jun. 27, 2014

(86) PCT No.: PCT/US2014/044662
§ 371 (c)(1),
(2) Date: Dec. 29, 2015

(87) PCT Pub. No.: WO2015/002841
PCT Pub. Date: Jan. 8, 2015

(65) Prior Publication Data
US 2016/0340686 A1 Nov. 24, 2016

(51) Int. Cl.
*C12N 15/82* (2006.01)
*C12P 19/02* (2006.01)
*C12P 19/14* (2006.01)
*C12N 9/10* (2006.01)

(52) U.S. Cl.
CPC ....... *C12N 15/8261* (2013.01); *C12N 9/1007* (2013.01); *C12P 19/02* (2013.01); *C12P 19/14* (2013.01); *C12Y 201/01* (2013.01); *Y02A 40/146* (2018.01)

(58) Field of Classification Search
None
See application file for complete search history.

(56) References Cited

U.S. PATENT DOCUMENTS

2007/0039067 A1* 2/2007 Feldmann ............ C07K 14/415
800/278

FOREIGN PATENT DOCUMENTS

| EP | 1586645 A2 | 10/2005 |
| EP | 2204451 A1 | 7/2010 |
| WO | WO-2011160050 A2 | 12/2011 |
| WO | WO-2015002841 A2 | 1/2015 |
| WO | WO-2015002841 A3 | 1/2015 |

OTHER PUBLICATIONS

"International Application Serial No. PCT/US2014/044662, International Search Report dated Jan. 15, 2015", 7 pgs.
"International Application Serial No. PCT/US2014/044662, Invitation to Pay Additional Fees and Partial Search Report dated Nov. 4, 2014", 6 pgs.
"International Application Serial No. PCT/US2014/044662, Written Opinion dated Jan. 15, 2015", 7 pgs.
Held, M. A., et al., "CGR3: A Golgi-Localized Protein Influencing Homogalacturonan Methylesterification", Molecular Plant, 4(5), (Sep. 2011), 832-844.
Lionetti, Vincenzo, et al., "Engineering the cell wall by reducing de-methyl-esterified homogalacturonan improves saccharification of plant tissues for bioconversion", Proceedings of the National Academy of Sciences, National Academy of Sciences, vol. 107, No. 2, (Jan. 12, 2010), 616-621.
Mouille, Gregory, et al., "Homogalacturonan synthesis in *Arabidopsis thaliana* requires a Golgi-localized protein with a putative methyltransferase domain", Plant Journal, vol. 50, No. 4, (May 2007), 605-614.
"International Application Serial No. PCT/US2014/044662, International Preliminary Report on Patentability dated Jan. 14, 2016", 10 pgs.
Kim, Sang-Jin, et al., "CGR2 and CGR3 have critical overlapping roles in pectin methylesteri?cation and plant growth in *Arabidopsis thaliana*", The Plant Journal, 82, (2015), 208-220.
Weraduwage, Sarathi M., "Pectin Methylesteri?cation Impacts the Relationship between Photosynthesis and Plant Growth", Plant Physiology, 171, (Jun. 2016), 833-848.

* cited by examiner

*Primary Examiner* — Brent T Page
(74) *Attorney, Agent, or Firm* — Schwegman Lundberg & Woessner, P.A.

(57) ABSTRACT

Plants described herein have increased biomass and are more readily digested into fermentable sugars when the plants express increased levels of one or more types of CGR2 and/or CGR3 enzymes.

17 Claims, 22 Drawing Sheets
Specification includes a Sequence Listing.

```
QUA2  MSMPLQRGI-SGVRVSDSSDDLRDSQMKDKTERARSTENNNLTLRFPF-GFLFSNQSSSK
CGR2  MA---RRQVGSTRRVGDGGS---------------------------FPFAGALHSKSRSSP
CGR3  MS---RRQV---RRVGDSGS---------------------------FPFVGALHSKSRSSP
       *:   :*: : :  **.*..                          *** * .*.*:. **
QUA2  HGGGGENGFSADPYSARSRHRLMLLFLKISLVLIVVIALAGSFWWTISISTSSRGHVYHN
CGR2  ------------------------LLSICLVL----------------------------
CGR3  ------------------------LLSVCLVL----------------------------
                              :*.:.***
QUA2  YRRLQEQLVSDLWDIGEISLGPNRWKELEYCNIESENFVPCFNVSENLALGYSNGDENDR
CGR2  -----------------------------------------------VGACLLIGYA-------
CGR3  -----------------------------------------------VGACLLIGYA-------
                                                      *.  *  :**:
QUA2  FCGPGSKQECLELPPVKYRVPLRWPTGKDIIWHSNVKITAQEVVSSGSITKRMMMMEDDQ
CGR2  YSGPG-------------------------------------------------------
CGR3  YSGPG-------------------------------------------------------
       :.***
QUA2  ISFRSASPMSDEVEDYS--HQIAEMIGIKKDNFIEAGVRTILDIGCGYGSFGAHLLSK--
CGR2  -IFKSIKEVSKVTGDYSCTAEVQRAIPVLKKAYGD-GMRKVLHVGPDTCSVVSSLLKEEE
CGR3  -MFKSIREVSKITGDYSCTAEVQRAIPILKSAYGD-SMRKVLHVGPETCSVVSSLLNEEE
        *.*  .*.  ***   ..    *  . * .*  :*.*.*   *  *   **.
QUA2  -QILTMCIANYEASGSQVQLTLERGLPAMIGSFISKQLPYPSLSFDMLHCLRCGIDWDQK
CGR2  TEAWGVEPYDIEDADSHCKSFVSKGLVRV--ADIKFPLPYRAKSFSLV------IVSDAL
CGR3  TEAWGVEPYDVEDADSNCKSLLHKGLVRV--ADIKFPLPYRSKSFSLV------IVSDAL
         .    . :* * .*..*: : :** **    * . ****..*.*:**     *  *
QUA2  DGL------LLVEIDRVLKPGGYFVWTSPLTNPRNKDHLKRWNFVHDFAESICW----T
CGR2  DYLSPKYLNKTVPELARVASDGVVLFAGLPGQQRAKVAELSKFGRPAKMRSASWWNRFFV
CGR3  DYLSPRYLNKTVPELARVASDGVVLLAGNPGQQKAKGGELSKFGRPAKMRSSSWWIRFFS
       * *        : *: **   * : ::    *  : : : .*.::  ..  ..:  *
QUA2  LLNQQDETVVWKKTINTKCYSSRKPGVGPSVCTKGHDVESPYYRPLQMCIGGTRSRRWIP
CGR2  QTNLEENDAPSKKFEQAVSKGLYKPA----------------------------------
CGR3  QTNLEENEAASKKFEQAASKSSYKPA----------------------------------
        *  :::  .  **  :: .  **.
QUA2  IEGRTRWPSRSNMNKTELSLYGLHPEVLGEDAENWKITVREYWSLLSPLIFSDHPKRPGD
CGR2  ------------------------------------------------------------
CGR3  ------------------------------------------------------------

QUA2  EDPSPPYNMLRNVLDMNAQFGGLNSALLEARKSVWVMNVVPTAGPNHLPMILDRGFVGVL
CGR2  ------------------------------------------------------------
CGR3  ------------------------------------------------------------

QUA2  HNWCEPFPTYPRTYDLVHADNLLSLQTSQPRKTCLLIDIFTEIDRLLRPEGWVIIRDTAQ
CGR2  ---CQVFHLKP-----LH------------------------------------------
CGR3  ---CQVFHLKP-----LH------------------------------------------
         *.  * *      .*
QUA2  LVEKARETITQLKWEARVIEVESSSEQRLLICQKPFTKRQSI  (SEQ ID NO:25)
CGR2  ------------------------------------------  (SEQ ID NO:2)
CGR3  ------------------------------------------  (SEQ ID NO:19)
```

▭▭▭ PF08241 (methyltransferase domain)
▭ ▭ ▭ DUF248 (methyltransferase domain)
▭▭▭ SAM binding domain    Mafet used

*Fig. 1A*

WT  cgr2-1 cgr3-1  cgr2-1  cgr3-1

DIGESTIBILITY OF PLANT BIOMASS

This invention was made with government support under DE-FG02-91ER20021 and DE-FC02-07ER64494 awarded by the U.S. Department of Energy. The government has certain rights in the invention.

This application is a U.S. National Stage Filing under 35 U.S.C. 371 from International Application No. PCT/US2014/044662 filed Jun. 27, 2014, which application claims benefit of the filing date of U.S. Provisional Application Ser. No. 61/842,077, filed Jul. 2, 2013, the contents of which applications are specifically incorporated here by reference in their entirety.

BACKGROUND

The ease of digesting various biomass sources into simpler molecules such as fermentable sugars relates to the utility of those sources for generating biofuels and other useful products. Pretreatment of plant biomass using harsh chemicals (strong acids, strong bases, ammonia) can help break down some of the complex polymers in plant materials. However, such pretreatment is expensive and the harsh chemicals employed can be toxic. What are needed are new types of plant biomass and methods of generating plant biomass that is more readily digested.

SUMMARY

As described herein, plants that express increased levels of CGR2 or CGR3 have increased biomass and the biomass from such plants is more readily digested into fermentable sugars.

Accordingly, one aspect of the invention is a plant that includes an expression cassette having an isolated nucleic acid segment encoding a CGR2 enzyme and/or an isolated nucleic acid segment encoding a CGR3 enzyme. The expression cassette can express the CGR2 enzyme and/or the CGR3 enzyme, or can be induced to express the CGR2 enzyme and/or the CGR3 enzyme, at levels sufficient to increase the plant's biomass by at least 5% compared to a wild type plant of the same species that does not comprise the expression cassette. Moreover, the plant's pectin has at least 5% more methylesters than a wild type plant of the same species that does not have the expression cassette. In addition, enzymatic digestion of biomass from the plant releases at least 15% more fermentable sugar than is released than from a wild type plant biomass of the same species that does not have the expression cassette.

Another aspect of the invention is a seed derived from such a plant.

A further aspect of the invention is a biomass derived from such a plant.

Another aspect of the invention is a method that involves digesting biomass from such a plant to yield fermentable sugars.

BRIEF DESCRIPTION OF THE FIGURES

FIGS. 1A-1G illustrate that CGR2 and CGR3 constitute a plant-specific gene family in *Arabidopsis* and provide expression and structural information on these gene products. FIG. 1A shows an amino acid sequence alignment of CGR2 (SEQ ID NO:2), CGR3 (SEQ ID NO:19) and QUA2 (SEQ ID NO:25) using an MAFFT sequence alignment program. QUA2 contains a putative methyltransferase domain (DUF248, boxed with a large broken line, and including positions 257-676 of SEQ ID NO:25), while CGR2 and CGR3 have a putative methyltransferase domain (PF08241, boxed with a dotted line, and including amino acids 146-187 of SEQ ID NO:2). The PF08241 methyltransferase domain of the CGR2 and CGR3 proteins is different from DUF248 domain commonly found in QUA2-like proteins. The SAM binding domain is boxed in a solid line and includes amino acids 276-376 of the QUA2 sequence (SEQ ID NO:25). FIG. 1B shows CGR2, CGR3 and QUA2 protein domain structures. Transmembrane domains are predicted to be at the N-terminus for all three proteins. Numbers on the top of the schematics indicate amino acid residue numbers. FIG. 1C shows confocal images of tobacco epidermal cells transiently co-expressing ManI-YFP (Golgi marker, center), a fusion of cerulean fluorescent protein (CFP) fused to the C-terminus of CGR2 (CGR2-cCFP; left) and a combination thereof (right). Scale=5 µm. FIG. 1D shows confocal images of tobacco epidermal cells transiently co-expressing ManI-YFP (Golgi marker, center), a fusion of cerulean fluorescent protein (CFP) fused to the C-terminus of CGR3 (CGR3-cCFP; left) and a combination thereof (right). Scale=5 µm. FIG. 1E shows a probability plot for the topology of CGR2 as predicted using TMHMM software (see website at cbs.dtu.dk/services/TMHMM-2.0/), where the amino acid number is shown along the X-axis and the probability of a domain being a transmembrane domain is plotted along the Y-axis. Segments predicted to be the inside domain (light line to the left) and the outside domain (dotted line to the right) of the protein are also identified. Note that due to the topology of the secretory pathway, 'outside' indicates a lumen orientation and 'inside' indicates a cytosolic orientation. FIG. 1F illustrates that CGR2 and CGR3 are type-II membrane proteins. Microsomes from CGR2-cCFP and CGR3-cCFP transgenic *Arabidopsis* plants were treated with either Triton X-100, proteinase K, or both. Bands of the predicted molecular size of CGR2-cCFP and CGR3-cCFP (56 kDa) were detected from non-treated and Triton X-100 treated samples. Truncated forms of CGR2-cCFP and CGR3-cCFP (52 kDa; asterisks) were detected from samples treated with proteinase K only. Cerulean fluorescent protein (CFP) degradation products were detected when the microsome lumen was accessed by proteinase K upon Triton X-100 treatment. FIG. 1G is a schematic representation of the topology of CGR2 and CGR3 with respect to the Golgi membrane and lumen.

FIG. 2A is a schematic diagram of the open reading frame of CGR2 showing the location of a T-DNA insertion in the fifth exon (cgr2-1). (Black bar—Exon; Grey bar—5' and 3' untranslated region; Thin Black line—intron).

Error bars represent the SE (n=3). FIG. 2I shows images of 6 week-old rosette leaves. Scale bar=5 cm. FIG. 2P shows images of silique from cgr2-1 cgr3-1 mutant plants transformed with CGR2-cCFP (CGR2com) or CGR3-cCFP (CGR3com).

FIG. 4A shows images of wild type and cgr2-1 cgr3-1 mutant pollen incubated within in vitro germination media after 24 hr incubation. Note the lack of extended tube elongation in the mutant compared to wild type. Scale bar=100 μm. FIG. 4B graphically illustrates the pollen tube length of wild type and cgr2-1 cgr3-1 mutant pollen tube lengths. Error bars represent SD; n=40 for each genotype. a, P<0.0001; b, P<0.06. FIG. 4C shows images of siliques from wild type and mutants. Siliques were cleared using 80% (w/v) chloral hydrate after fixing with 3:1 (v/v) ethanol: acetic acid. Arrows indicate empty spaces in the silique. FIG. 4D shows immuno-fluorescence images of germinating pollen. Pollen grains were harvested and incubated for 3 hr in liquid pollen germination medium. The pollen was mounted onto a slide and labeled with JIM7 antibody to label the high degree methyl-esterified homogalacturonan. Decreased labeling of JIM7 in the cgr2-1 cgr3-1 mutant was observed by confocal microscopy. The arrow indicates emerging pollen tube.

FIG. 5A graphically illustrates the quantity of alcohol-insoluble residues (AIR) from leaf tissue as analyzed for the quantity of neutral sugars using alditol acetate derivatives. FIG. 5B graphically illustrates the levels of crystalline cellulose from alcohol-insoluble residues. FIG. 5C graphically illustrates uronic acid levels from alcohol-insoluble residues measured using a colorimetric method (Filisetti-Cozzi and Carpita, 1991). D-galacturonic acid was used as a standard to calculate concentration. Error bars represent the SD (n=3 for each genotype). FIG. 5D graphically illustrates the molar ratios of methylesters per uronic acid for various plants types, as estimated by release of methanol from methyl-esters after saponification of alcohol-insoluble residues (Wood and Siddiqui, 1971). Methanol was used as a standard to calculate concentration. Error bars represent SD (n=3 for each genotype).

FIG. 8A graphically illustrates glucose release from the biomass of various plants types pretreated with the EDTA or pectinase as described in Example 9 compared to no such treatment. FIG. 8B graphically illustrates glucose release from plant biomass pretreated with alkaline hydrogen peroxide. After pretreatment, the plant biomass samples were digested with Ctec:Htec (75:25) enzymes and the amount of glucose released was detected. Error bars represent the standard deviation (n=3).

DETAILED DESCRIPTION

Figure 1B:
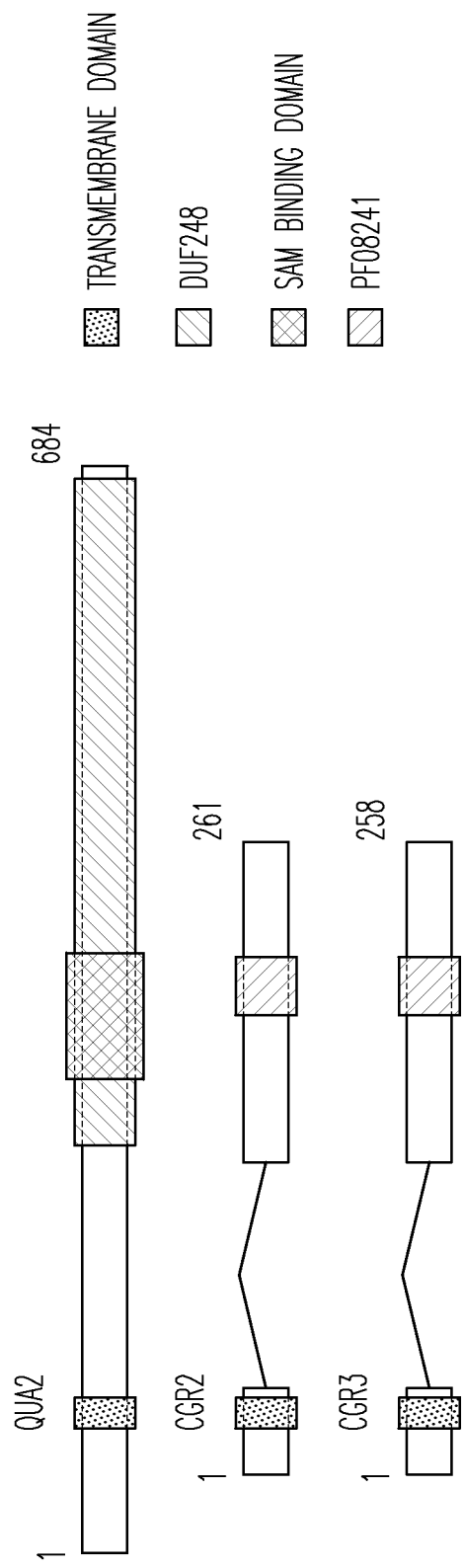

The plant biomass and methods of producing such plant biomass described herein facilitate production of useful fermentable sugars that can readily be converted into bio-fuels and other useful products. Plants and methods that include overexpression of CGR2 and CGR3 not only generate increased plant biomass but also increase the digestibility of that biomass. Accordingly, the nucleic acids, expression cassettes, plants, seeds and methods described herein can be used to improve the quality and quantity of plant materials for bio-fuel production and other uses.

Two qualities are important for bio-fuel from plants: biomass and biomass digestibility. Biomass is important as an initial input for digestion, and digestibility is important to produce more monosaccharide for fermentation to yield ethanol. The digestibility of biomass can be improved by physical or chemical pre-treatment. However, pre-treatment of biomass requires extra money and time. In contrast when plants are engineered to overexpress CGR2 and/or CGR3 proteins, up to 33%-43% increases in saccharification are observed compared to wild type plants without such overexpression. Increased methyl-esterification of homogalacturonan by CGR2 or CGR3 can therefore increase yields and reduce the costs of biomass digestion.

Pectin and Homogalacturonan

Pectins are polysaccharides, consisting of homogalacturonan (HG), rhamnogalacturonan I (RG-I), and rhamnogalacturonan II (RG-II) moieties. Homogalacturonan has a polysaccharide of alpha-1,4-linked galacturonic acid residues (GalUA). The galacturonic acid residues of the homogalacturonan backbone can be methyl-esterified on the carboxylate group at the C-6 position and can also be 0-acetylated at the C-2 or C-3 positions (O'Neill et al., 1990).

Pectins are polysaccharides in the plant cell wall and are involved in several important functions in plants, including cell wall stiffness, cell-to-cell adhesion, and mechanical strength. The methyl-esterification of homogalacturonan can regulate the cellular role of pectin.

The *Arabidopsis* genome contains 29 genes encoding putative methyltransferases that include GMT-1 and GMT-2, QUA2/TSD2 and QUA3 (Dunkley et al., 2006; Krupkova et al., 2007; Mouille et al., 2007; Miao et al., 2011), but the activity of these proteins as true homogalacturonan methyltransferases has yet to be demonstrated. Recent characterization by the inventors of a distantly related *Arabidopsis* protein named CGR3 provided some characterization of CGR3 (Held et al., 2011). However, there is no direct evidence showing that these proteins actually are homogalacturonan methyltransferases.

CGR2 and CGR3

As described herein, CGR2 and CGR3 are methyltransferases that transfer methyl groups from methyl donors to homogalacturonan, a component of pectin. Homogalacturonan is a polymer of alpha-1,4-linked galacturonic acid residues. Experimental data reported herein demonstrates that CGR2 and CGR3 transfer methyl groups to the carboxylate at position C-6 of the galacturonic acid, as illustrated below.

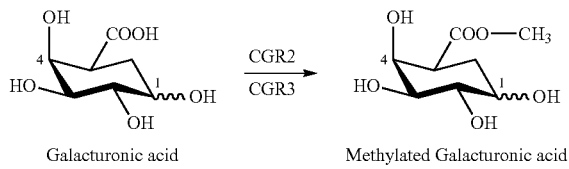

Galacturonic acid   Methylated Galacturonic acid

Sequences for CGR2 nucleic acids and proteins are available from the arabidopsis.org website. For example, one cDNA sequence for CGR2 from *Arabidopsis thaliana* has accession number At3g49720.1 and is provided below as (SEQ ID NO:1).

```
  1  AGTGATATTA ACACTTCGAA GCTTCTTCTT CCTTTAGTAA
 41  ATTCAAGTGT GAGGTGTGTT TATTGATAAA GTGCTCATTT
 81  TCTCGGATCT CAGATCTTAG ATCCAAACCC TCATTATTTC
121  ATTGATCCAA GATCTAATAG CTTGAGCTTG CTGGGATTTT
161  AGTTATGGCG AGACGGCAAG TAGGTTCAAC AAGACGTGTT
201  GGCGATGGTG GAAGCTTCCC TTTTGCAGGA GCTTTACACT
241  CAAAGTCTCG ATCTTCTCCA CTACTATCTA TTTGCCTTGT
281  TCTTGTGGGG GCTTGTCTTC TCATTGGTTA TGCTTACAGT
321  GGTCCAGGTA TATTTAAAAG TATCAAAGAA GTTAGCAAAG
361  TTACAGGTGA CTATTCTTGC ACAGCAGAAG TCCAAAGAGC
401  CATTCCTGTA CTTAAGAAGG CTTATGGAGA TGGCATGCGC
441  AAAGTCTTGC ATGTGGGCCC TGACACATGC TCAGTGGTTT
481  CCAGTCTATT GAAAGAAGAA GAGACTGAAG CATGGGGTGT
521  TGAACCATAT GATATTGAGG ATGCAGATTC TCACTGCAAG
561  AGTTTTGTGA GCAAAGGTCT TGTACGTGTT GCTGATATCA
601  AGTTTCCTCT GCCCTACCGG GCAAAATCCT TCTCTCTTGT
641  GATTGTGTCA GATGCTCTGG ATTATCTCTC ACCCAAGTAC
681  CTGAACAAGA CCGTTCCTGA ACTCGCAAGG GTGGCTTCAG
721  ACGGTGTGGT TCTTTTTGCA GGTCTCCCTG GTCAGCAGAG
761  AGCTAAAGTT GCTGAACTCT CTAAATTCGG CCGACCCGCT
801  AAAATGCGTA GCGCATCGTG GTGGAACCGC TTTTTCGTCC
841  AGACAAACTT AGAAGAAAAC GATGCACCAA GCAAGAAGTT
881  CGAACAGGCT GTTTCCAAAG GATTATACAA ACCAGCCTGC
921  CAAGTCTTCC ACCTCAAGCC ATTACATTAA CCAGCCACCA
961  CCAAAGCCTA CTGGTTCCAC ACCAAAGCAT ATTTACACGT
1001 AGAGCCGCAC GCGAAAAAAA AAAATAGCGT AATCGATATT
1041 TCTCCTTGTA TTTTGTAACA GGTCAGTTTT TATCCTTCAA
1081 TGTTGTATCC GCCAACACAA TTTTTCCTAT TCAATTAAAT
1121 CATAATTATT ATCACCAAT
```

The *Arabidopsis thaliana* CGR2 polypeptide sequence encoded by the above nucleic acid (SEQ ID NO:1) is provided below as SEQ ID NO:2:

```
  1  MARRQVGSTR RVGDGGSFPF AGALHSKSRSS PLLSICLVLV
 41  GACLLIGYAY SGPGIFKSIK EVSKVTGDYSC TAEVQRAIPV
 81  LKKAYGDGMR KVLHVGPDTC SVVSSLLKEEE TEAWGVEPYD
121  IEDADSHCKS FVSKGLVRVA DIKFPLPYRAK SFSLVIVSDA
161  LDYLSPKYLN KTVPELARVA SDGVVLFAGLP GQQRAKVAEL
201  SKFGRPAKMR SASWWNRFFV QTNLEENDAPS KKFEQAVSKG
241  LYKPACQVFH LKPLH
```

The CGR2 protein has a methyltransferase domain (PF08241) that includes amino acids 146-187 of the SEQ ID NO:2 sequence (underlined and in bold in the SEQ ID NO:2 sequence shown above).

Another CGR2 nucleic acid sequence from *Arabidopsis thaliana* is available from the arabidopsis.org database named RAFL21-52-D04 (NCBI accession no. AK317656), which has the following sequence (SEQ ID NO:3).

```
  1 ATTAACACTT CGAAGCTTCT TCTTCCTTTA GTAAATTCAA
 41 GTGTGAGGTG TGTTTATTGA TAAAGTGCTC ATTTTCTCGG
 81 ATCTCAGATC TTAGATCCAA ACCCTCATTA TTTCATTGAT
121 CCAAGATCTA ATAGCTTGAG CTTGCTGGGA TTTTAGTTAT
161 GGCGAGACGG CAAGTAGGTT CAACAAGACG TGTTGGCGAT
201 GGTGGAAGCT TCCCTTTTGC AGGAGCTTTA CACTCAAAGT
241 CTCGATCTTC TCCACTACTA TCTATTTGCC TTGTTCTTGT
281 GGGGGCTTGT CTTCTCATTG GTTATGCTTA CAGTGGTCCA
321 GGTATATTTA AAAGTATCAA AGAAGTTAGC AAAGTTACAG
361 GTGACTATTC TTGCACAGCA GAAGTCCAAA GAGCCATTCC
401 TGTACTTAAG AAGGCTTATG GAGATGGCAT GCGCAAAGTC
441 TTGCATGTGG GCCCTGACAC ATGCTCAGTG GTTTCCAGTC
481 TATTGAAAGA AGAAGAGACT GAAGCATGGG GTGTTGAACC
521 ATATGATATT GAGGATGCAG ATTCTCACTG CAAGAGTTTT
561 GTGAGCAAAG GTCTTGTACG TGTTGCTGAT ATCAAGTTTC
601 CTCTGCCCTA CCGGGCAAAA TCCTTCTCTC TTGTGATTGT
641 GTCAGATGCT CTGGATTATC TCTCACCCAA GTACCTGAAC
681 AAGACCGTTC CTGAACTCGC AAGGGTGGCT TCAGACGGTG
721 TGGTTCTTTT TGCAGGTCTC CCTGGTCAGC AGAGAGCTAA
761 AGTTGCTGAA CTCTCTAAAT TCGGCCGACC CGCTAAAATG
801 CGTAGCGCAT CGTGGTGGAA CCGCTTTTTC GTCCAGACAA
841 ACTTAGAAGA AAACGATGCA CCAAGCAAGA AGTTCGAACA
881 GGCTGTTTCC AAAGGATTAT ACAAACCAGC CTGCCAAGTC
921 TTCCACCTCA AGCCATTACA TTAACCAGCC ACCACCAAAG
961 CCTACTGGTT CCACACCAAA GCATATTTAC ACGTAGAGCC
1001 GCACGCGAAA AAAAAAAATA GCGTAATCGA TATTTCTCCT
1041 TGTATTTTGT AACAGGTCAG TTTTTATCCT TCAATGTTGT
1051 ATCCGCCAAC ACAATTTTTC CTATTCAATT AAATCATAAT
1101 TATTATCAAA AAAAAAAAA AAA
```

The foregoing nucleic acid sequence (SEQ ID NO:3) also encodes the SEQ ID NO:2 polypeptide sequence.

Nucleic acid and protein with related sequences can be used in the methods, genetic constructs, plant parts and plants described herein.

For example, *Arabidopsis lyrata* (subsp. *lyrata*) has a nucleic acid sequence with sequence homology to SEQ ID NO:1. This *Arabidopsis lyrata* sequence has accession no. XM_002866644.1 (GI:297797610) in the NCBI database and is provided below as SEQ ID NO:4.

```
  1 ATGTCAAGAA GGCAAGTAAG GCGTGTAGGG GATAGTGGAA
 41 GCTTCCCATT TGTAGGAGCT TTGCATTCGA AATCGCGTTC
 61 GTCTCCTTTG TTATCTGTTT GCCTTGTTCT CGTGGGAGCA
121 TGCCTTCTCA TTGGTTATGC TTACAGTGGT CCAGGTATGT
161 TCAAAAGTAT CAGAGAAGTC AGCAAGATCA CAGGGGACTA
201 CTCTTGCACA GCAGAAGTTC AAAGAGCCAT TCCTGTTCTT
241 AAGAGTGCGT ATGGAGATAC CATGCGCAAA GTCTTGCACG
281 TGGGTCCCGA AACATGCTCA GTCGTCTCGA GTCTGTTGAA
321 TGAAGAAGAG ACGGAAGCAT GGGGTGTTGA ACCGTATGAT
361 GTGGAGGATG CAGATTCTAA CTGCAAAAGT CTTTTGCACA
401 AAGGCCTTGT ACGTGTGGCT GACATCAAAT TCCCTCTGCC
441 TTACCGGTCA AAGTCGTTTT CTCTTGTGAT CGTCTCAGAC
481 GCATTGGATT ACCTCTCACC CAGGTACCTG AACAAAACCG
521 TGCCTGAACT TGCACGGGTC GCTTCAGATG GTGTCGTTCT
561 TTTTGCAGGT AACCCTGGTC AACAAAAGGC TAAAGGTGCG
601 GAATTGTCGA AATTTGGACG ACCAGCTAAA ATGCGTAGCT
641 CGTCCTGGTG GATCCGTTTC TTCTCACAGA CGAACTTAGA
681 GGAAAACGAA GCAGCAATCA AGAAATTCGA ACAAGCAGCT
721 TCCAAGAGTT CATACAAACC AGCTTGTCAA GTTTTCCACC
761 TCAAGCCATT ACATTAG
```

The SEQ ID NO:4 nucleic acid from *Arabidopsis lyrata* encodes a polypeptide reported to have no known function, but with 87% sequence identity to SEQ ID NO:2. The polypeptide encoded by the SEQ ID NO:4 nucleic acid has the following sequence (SEQ ID NO:5).

```
  1 MSRRQVRRVG DSGSFPFVGA LHSKSRSSPL LSVCLVLVGA
 41 CLLIGYAYSG PGMFKSIREV SKITGDYSCT AEVQRAIPVL
 81 KSAYGDTMRK VLHVGPETCS VVSSLLNEEE TEAWGVEPYD
121 VEDADSNCKS LLHKGLVRVA DIKFPLPYRS KSFSLVIVSD
161 ALDYLSPRYL NKTVPELARV ASDGVVLFAG NPGQQKAKGA
201 ELSKFGRPAK MRSSSWWIRF FSQTNLEENE AAIKKFEQAA
241 SKSSYKPACQ VFHLKPLH
```

*Vitis vinifera* also has a genomic nucleic acid with sequence homology to SEQ ID NO:1. This *Vitis vinifera* sequence has accession no. AM463368.2 (GI:147801367) in the NCBI database and is provided below as SEQ ID NO:6.

```
  1 TTTCATCAAT CAATGGTATG AGTTGAGGTG AAACACCTGG
 41 CATGCTGGCT TGTAAGACTT CTTGGCTGCA GCCTGATCAA
 81 ACTTTTTGAT GGCAGCTTCA TTCTCTTCTA AGCTGGTCTG
121 AACAAAATAC CGTATCCACC AAGATGAGCT TCGCATTTTT
161 GCCTTCACAC AGAAAAAAGG CATTGGGATA TGTCATATTT
201 TAATTAAACT GAGGTTTTAG TGATAGAATT CAATGTTACT
241 GACCAGAAAC GAACCCCATA ATAAAACAAG GCCTGCCAAA
281 AACAAAATTT TCCATACCCT TTTGTCTCAC TCCATAATAA
321 ACTAATCATC TCAGCAGATG CACTCATGTT TTTTTCAATT
361 TTCAAGCATG AAATGTAACA ATGTTACAAT TTTTTTTGGA
```

```
 401 CTAATCTTTT GTTTGGTCTC TTTATAAAAT TAAATATTCC
 441 ACTCCGTATC TTCCTGTTGT TATTACCAAG TTGCCATTAT
 481 TTGATTGTTT TACTGTAAGT TCTAATCATA AAAATTTTGT
 521 ATGGAACAAG TAAAATTGTA CAAGCAGTAG ATCGCCACTT
 561 ACTGGCCGTC CAAATTTGGA TAACTCTGCA ACTTTAGCTT
 601 TCTGTTGACC AGGAAGACCT ACACAGAAAT TGAAAACAGT
 641 GAAAACCCAT TAACATTAAC CACTTTTTAT GTCAATTGAA
 681 CTTTTAGCGC TAGAAAAATT ACAGATGAAG TTTATTTGCC
 721 CAAGCAAACA AACTACTGAA GTTCACCCGG AGGAACCTGG
 761 GAGATATACA ACATGCAATT AAACAATCAT TTAGAAATCT
 801 ATTTATGTCC AACAGGAAAG TCACCTAAAC ACTAAAGAAG
 841 TTTGTATTGC TTCTAAATCG TTGATTGTGA TGAAAGGGTA
 881 ATTATAGGAG TTTCTTTCAC CGTCAACTAT CAAATCAAAA
 921 CCAAAGCTAA GAGGCAAGAA AAAATATATG ATATCATCTC
 961 TATTCACAAA ATTACCAACC TAGCAGAGAG AGTGCAATAG
1001 CTTATCATCA CATCAATTGG GAGGTTACTA AGGTTGCTCA
1041 TGCATTGACC AAAAAGGATA GCTAGACAGA GAGACCAGAA
1081 CAGCTTATCA TCGCATCAAT TGGGAGGTTA CCGAAGTTGC
1121 TGGTGTATTG GCCAAAAAAG ATGTAGCTAG AATGAAATTA
1161 TTTCCTAAAT CATCAAGTAA AACAAAAATT CTACCAAATA
1201 CGACATATTT ATATTTAGCA AATTTTCTAT AGCATGACTT
1241 TTTTTATAGG TTTTTTTCTT TCTTTCTACT TGGAATTCCC
1281 CATCCCACCC CACCCCACCC CAACCCCTTG CCACTAGAGC
1321 TAGGCCTCAA GAGCCTCTTA TGACGAATAT AAATATTTCA
1361 GGGAATTACC TGCAAAAATA CAAGACCAT CACTGGACAC
1401 CCTTGCCAAA TCAGGAAGAG TCTTGTTCAA GTACTTTGGA
1441 GAAAGGTAAT CCAATGCATC TGACACAATA ACAAGAGAAA
1481 ATGACTTTGG CCTGTAGGGC ATAGGGAACT TGATATCAGC
1521 CACACGAACA ATGCTTTTAC GGACAAGACT CTTGCAGCTC
1561 CCATCAGCAT CCTCTATGTC ATATGGTTCT ACACCCCATG
1601 CTTCTGTTTC CTCCTCCTTT AACAATTTAG AGACCACTGA
1641 ACAGGTATCA GGGCCCACAT GCAAAACTTT GCGCATGCTG
1681 TCACCATATG CTTTCTTTAG AATAGGTATT GCTCTCTGAA
1721 CTTCTAAGGT GCATGAAAAA TCACCTACAT GCATTGACAT
1761 ATTTGAGTCT TTCTGCAGGA GATAAATAGT TCCATCCTAA
1801 TAAAATGAAA TTCCAACTAC CACTATCATG AAGGTTAAAG
1841 ATAGTGCTAA TGGTTCTTAA CCACAAAACA TTTACTAGTG
1881 CTTTATCCAT ACCAGTTCAA ACCTCATTTT TTTGGCCAGA
1921 ATTTCAGTAG CAACTTGAGA TGGAAATAAT ATATTACTAA
1961 AAAGCTAAAA CCGATTAGCA TTATGAAATG GCTAAATTAA
2001 AAATAAAAAC AAAAATGAAA ATCTAAGTCT CAAGAACTGG
2041 TAGAGGGTTA CAGCCTTTAT CTATAAAGAT AAAGGGTAGG
2081 AATATTTCAA GGTGACCAAC TCGTTATACT GAATCCACGA
2121 GGAAACCATA ACAAGGACAT AATAATACAA GAAATTATCT
2161 TGAATAACAT TTTTGGAGTT CAAGTCAAAA GTTAGAATAT
2201 CCTTTCAATC ATTTCCACTA TGGAAGAACA ATTGTTAGTC
2241 TTCTGTATGG CCATTTACAA GAGAAGAARA GATCCATGGG
2281 CAGCAACATT ACTGAAGAAA TTAGACAAGA AGTCATAGCA
2321 CTCCATCCTG CAGACTCCTG AACAAGAAAT CCAACAAGAT
2361 GAGAATAAAA GAGCCAAATT TTTTTTACCT TCAACCTTAC
2401 TAAAAGCTTC CTTGTCACCA CCAAATAGAC CTGTATTGTG
2441 AAAAACAAGA TCGAAATCAA TTTAAAGAAA GAAAAATGTA
2481 CAACTGTCTA GAATTTCAAA GCAAGTATGG CAAATCAAGA
2521 CATGAGAATC ATCCTAAGAT TAAAAGTGTA ATAGTTCATG
2561 ATGTAGATAG CTATCTATGA CAGCAAGAAG CCAAGTTCCC
2601 ATGACTAGTC CATTGGATTG AAAGAAAAGC AAATACAGAC
2641 CTGACCCACT ATAAGAATAA GCAACAAGAA GGAATGCCCC
2681 CTGCATGTTT CAAGAAAAAA GAATCAGAAC TTGTATTGTC
2721 AACCAGAACC ACTTGTGGTG TTTCTCAAAG TGGGGAAATA
2761 TTTGGGCAAC AATAACCAAT TAACCATAAT CTTTAAATGA
2801 AGTAATAACC AATGCTAGAA ATTGTCAAAA GGAAAAGGTG
2841 AACCAGAGAC GAGAAATACC AGAAGGACAA GACCAATGGA
2881 TAATAAGGGA GAAGAGCGTG ATTTTGAATG TAAGGCTCCT
2921 GCAAATGGAA TGCTTCCACT GTCCACAAAG CGCCGTGAGG
2961 GATTTACTTG TCTCCTTGAC ATGACTACTC TTGTAATACA
```

The SEQ ID NO:6 nucleic acid from encodes a *Vitis vinifera* polypeptide reported to have no known function, but with 77% sequence identity to SEQ ID NO:2. The polypeptide encoded by the SEQ ID NO:6 nucleic acid has accession number CAN74732.1 (GI:147801370) in the NCBI database, and the following sequence (SEQ ID NO:7).

```
  1 MSRRQVNPSR RFVDSGSIPF AGALHSKSRS SPLLSIGLVL
 41 LGAFLLVAYS YSGSDSNMSM HVGDFSCTLE VQRAIPILKK
 81 AYGDSMRKVL HVGPDTCSVV SKLLKEEETE AWGVEPYDIE
121 DADGSCKSLV RKSIVRVADI KFPMPYRPKS FSLVIVSDAL
161 DYLSPKYLNK TLPDLARVSS DGLVIFAGLP GQQKAKVAEL
201 SKFGRPAKMR SSSWWIRYFV QTSLEENEAA IKKFDQAAAK
241 KSYKPACQVF HLNSYH
```

*Cucumis sativus* also has a nucleic acid with sequence homology to SEQ ID NO:1. This *Cucumis sativus* sequence has accession no. XM_004142316.1 (GI:449449221) in the NCBI database and is provided below as SEQ ID NO:8.

```
  1 GTATTTCTAT TTCCCACTTG CACTTCCTTC TTTCTCCACC
 41 TCTCCACCTC TCCACCTCTC TACCTCTCTA CCATCCATCC
 81 TGTTGGATGT AACTACGCCA CAACGAACTA ATAAAACCCC
121 CCAAAAGAGG AATTTAATTT CCAGATCCAA GATCTACACT
161 TTCACAAACT AAATGCTGCT TTCCTTCTTG TCTGATCTGA
201 TCTGAGGTGG TTTTTCCAGA TCCGATTCAA TTTCTCTTAC
241 CTTTGTGTTT GATTCCAGAA ACATATTCTT TGGAACTCTT
281 AATTATGCAA CGGAGGCAAC CCACTTCGAC TCGTCGCAAT
321 GGAAGCTTTC CATTTGCTGG GGCCCTCAAT GCCAAATCAA
361 AAGCATCTCC CTTGCTATCT ATATGCTTGG TCCTTGTGGG
401 AGCAATTCTT CTACTTGTCT ATGCTTTTAG TGGACCAGGT
441 TTATTTGGAG GCACCAAGAT AGTCAGCAAG ATTGAAGGTG
481 ATTTTTCATG CACATTGGAG TTGCAAAGAG CAATACCCAT
521 CTTAAAGAAA GCATTCGGCG ATAGCATGCG CAAAGTTTTG
561 CATGTTGGTC CCGATACCTG TTTCGTGGTA TCCAAGCTGT
601 TGAAAGAAGG TGAAACAGAA GCATGGGGCA TAGAACCATA
641 CGACATAGAA GATGCTGATG GAAAGTGCAA ATCACTTGTG
681 AACAAAGGCA TTGTACGTGT GGCAGATATC AAATTCCCTC
721 TACCCTATAG GTCAAAGTCA TTTTCCCACG TTATTGTGTC
761 CGATGCATTG GACTACCTAT CCCCCAAATA CCTGAACAAA
801 ACTCTTCCAG AATTTGCAAG GGTTTCTTCT GATGGTCTTG
841 TTATATTTAC AGGTTCCCCT GGTCAACAGA AAGCTAAAGT
881 AAACGAGTTA TCAAAGTTTG GACGACCGGC CAAATTGCGG
921 AGCTCGTCTT GGTGGATTCG ATTTTTTGTC CAAACAAGCT
961 TAGAAGAGGA CGAAGGTTCT GCCAAGAAAT TTGAGCAAGC
1001 AGCATCGAAG CAGTCTTACA AGCCCGGTTG TCAAGTTTTC
1041 CATCTCAATT CATACCATTG ATATCGTGAA ATCACAAGCT
1081 ATGAAATTAT TTTCTTACCC CCTTTTTGTC TCCTTTTCTT
1121 CTCCGTCTTA TGTTATAAAC AAACACAAGA GAAGCTAGGG
1161 AGGTGGATTT GTTTTGTTTT GTTTTGTTTT TTATATGGTA
1201 GGTTGGGGGA ACGTTTTTGG CACATAATTG TGAACCATAG
1241 GAGATTTTAG TGTTCTCAAA TTCTTACATT ACGATATATT
1281 AATTATTTTT TATTTAATGA GATAAATATA ACTGATATTC
1321 ATA
```

The SEQ ID NO:8 nucleic acid from encodes a *Cucumis sativus* polypeptide reported to have no known function, but with 76% sequence identity to SEQ ID NO:2. The polypeptide encoded by the SEQ ID NO:8 nucleic acid has accession number XP_004142364.1 (GI:449449222) in the NCBI database, and the following sequence (SEQ ID NO:9).

```
  1 MQRRQPTSTR RNGSFPPAGA LNAKSKASPL LSICLVLVGA
 41 ILLLVYAFSG PGLFGGTKIV SKIEGDFSCT LELQRAIPIL
 81 KKAFGDSMRK VLHVGPDTCS VVSKLLKEGE TEAWGIEPYD
121 IEDADGKCKS LVNKGIVRVA DIKFPLPYRS KSFSHVIVSD
161 ALDYLSPKYL NKTLPEFARV SSDGLVIFTG SPGQQKAKVN
201 ELSKFGRPAK LRSSSWWIRF FVQTSLEEDE GSAKKFEQAA
241 SKQSYKPGCQ VFHLNSYH
```

*Fragaria vesca* also has a nucleic acid with sequence homology to SEQ ID NO:1. This *Fragaria vesca* sequence has accession no. XM_004289676.1 (GI:470106751) in the NCBI database and is provided below as SEQ ID NO:10.

```
  1 GTAGAAATCG GTGTGTCCCA AGCTACGACT CTCTTCAACC
 41 TTCAGTATTA GAAACTTAGT CTAAGCTCTC CAAAGTGTAA
 61 GACCAGCAGT CCAGCACAGA TCTGAATCGG CCTTCCCCTA
121 GATCTCTATT TCCACTTAAG GTCCATTGCT ATTATATCAG
161 CATGTCCAGG AGGCCAGTCA ATCCTGCTAG GCGCATTGGT
201 GATGGTGGAA GCATCCCATT TGTGGGTGCG GTGCAGGCCA
241 AAGCGAGCTC ATCACCTGTA CTGTCTGTAG CGCTTGTGCT
281 TCTGGGTACA ATTCTTCTTG TCTGCTATGC TTTTAGCGGG
321 TCAGGTGGAG TGAGCAGTAA AGAGGCTGTG ATTAAACTTG
361 AAGGTGGTGT TTCATGTACA CTCGAAGTTC AGAGAGCAAT
401 ACCTATACTA AAGAAGGCAT ATGGTGATAG CATGCATAAG
441 GTATTGCATG TAGGCCCTGA AACATGTTCA GTTGTATCTA
481 AATTATTAAA AGAGGAGGAG ACTGAAGCCT GGGGTGTGGA
521 ACCATATGAC TTGGAAGATG TTGATGGAAA TTGCAAGAGT
561 CTTGTGAACA AAGGCATTGT GCGTGCTGCT GATATAAAGT
601 TTCCTCTTCC ATACCGGGCA AAATCATTTT CTCTGGTAAT
641 AGTATCAGAT GCATTAGATT ACTTGTCTCC GAAGTACCTC
681 AACAGAACTC TTCCAGAGTT AGCAAGGGTA TCTGCTGATG
721 GCGTAATTAT TTTCTCTGGT TATCCAGGTC AACAAAGAGC
761 TAAAGTTGCA GAGCTATCCA AATTTGGCCG TCCAGCCAAA
801 TTGCGAAGCT CATCCTGGTG GATAAGATTT TTTGTTCAAA
841 CAAGCTTAGA AGAGAATGAA TCAGCCTCGA AGAAGTTTGA
881 ACAGGCTGCA TTAAAGAGAT CTTATAAGCC CGAATGTCAG
921 GTATTCCACC TTAAGTCATA CCATTGAGAA TCACATCATT
961 GTATCTTTCA TTGTATCAGT TATACCATTG CACAAAAGGT
1001 AACTATATAT TTTGTGAAAT ACGGAACCTC ATTATGTGCT
1041 CCTTTATGAG ACGAGATTTC TGATAGATGT GTACTAAGGA
1081 ATGATTTCCC AAGAATTGGG TACTGTCATC ACTTTGTATT
1121 CTTTTATACG ATGTATTTGC CGCCCACATT GCTGGTTCTT
1161 GTTGTTGCAA TGATAGATTT GTTAGAATGT TCAGATATAC
1201 ATTTGTTGAT TATATTGATA AGACAGTCGT ATATCGTTTT
1241 AGTGATGCAA TCAATTCTAT CTTTTGATGC ATGCCCTCAG
```

```
1281 TGGAGAAGTC AATTTCCACT AAAATTAAAA CTTATTTTAC

1321 CACGTTGAGG ACCTTATTTA CGCCATGACT GGAGGCTGTA

1361 CCTGACGCCA TGGCCGGAGG CTTTACCTTA ATGTGTCATA

1401 GATCCACATA GTATTGAAAA GGGAAT
```

The SEQ ID NO:10 nucleic acid from encodes a *Fragaria vesca* polypeptide reported to have no known function, but with 73% sequence identity to SEQ ID NO:2. The polypeptide encoded by the SEQ ID NO:10 nucleic acid has accession number XP_004289724.1 (GI:470106752) in the NCBI database, and the following sequence (SEQ ID NO:11).

```
  1 MSRRPVNPAR RIGDGGSIPF VGAVQAKASS SPVLSVALVL

41 LGTILLVCYA FSGSGGVSSK EAVIKLEGGV SCTLEVQRAI

81 PILKKAYGDS MHKVLHVGPE TCSVVSKLLK EEETEAWGVE

121 PYDLEDVDGN CKSLVNKGIV RAADIKFPLP YRAKSFSLVI

161 VSDALDYLSP KYLNRTLPEL ARVSADGVII FSGYPGQQRA

201 KVAELSKFGR PAKLRSSSWW IRFFVQTSLE ENESASKKFE

241 QAALKRSYKP ECQVFHLKSY H
```

*Populus trichocarpa* also has a nucleic acid with sequence homology to SEQ ID NO:1. This *Populus trichocarpa* sequence has accession no. XM_002313903.1 (GI: 224105810) in the NCBI database and is provided below as SEQ ID NO:12.

```
  1 GGATCAAGCA ATCAATCTCT GGGTCTCTCG CTCGCTCTCC

41 CAACTAGCTT ACCATCAAAA CAGATAGATC CAGATCGCGC

81 TTTAAAAGAT CTCCAACCCC TAACCCTTTC CACTCGATCT

121 CTCAGTTTGA TTGTAGGCAG GCCTCTTTTG TTTTAGGTTA

161 AATAACGAAA AATGTCGAGG AGGCCAGGGA ATCCTGCCAG

201 ACGTTTGGCT GATGGAGGAA GTCTTCCTTT TGCTGGGTCG

241 ATGCATTCTA AATCGCGTTC GTCGCCGTTA CTATCCATTG

281 GCCTTGTTGT CGTGGGCGCG ATTCTTCTTA TTGGATACTG

321 TTACAGTGGC TCAGGTGGGC ATATCACCAA TAGAGAAGCT

361 TTAAGTAAGA CAGAAGGTGG TGTTTCTTGC ACACTAGAAG

401 TCCAAAGAGC GATACCTTTT CTGAAGAAGG CTTATGGTGA

441 CAGCATGCGT AAAGTACTGC ATGTAGGCCC GGACACTTGT

481 TCTGCAGTAT CAAGCTTATT AAAAGAAGAG GATACCGAGG

521 CCTGGGGTGT GGAGCCATAT GACTTAGATG ATGTGAGTGC

561 CAACTGCAAG AGTCTTGTGC GCAAAGGCCT TGTGCGTGTA

601 GCTGATATCA AATTTCCTCT GCCCTACCGG CCAAAATCAT

641 TCTCTCTTGT TATAGTGTCA GATGCGTTGG ATTACTTGTC

681 TCCAAAATAT CTCAACAAAA CACTTCCAGA ATTGGCAAGG

721 GTGTCTGCTG ATGGCCTAGT TGTATTTTCT GGCGCTCCAG

761 GTCAGCAAAG AGTTAAAGTT GCAGAGTTGT CTAAGTTTGG

801 TCGTCCGGCC AAATTCCGGA CCTCAACATG GTGGATAAGG

841 TACTTTGTTC AGACTGGTTT ACAAGAGAAT GAATCTGCCT

881 TAAAGAAGTT TGAGCAGGCG GCATTGAAGA AGTCATATAA

921 GCCAGCCTGC CAAGTTTTCC ACCTCCAGTC ATATGATTGA

961 AAGTTTTGGT GTCATAACAT TTTCCATTGC TCTGTCTGCA

1001 AACTGGCAAC AAACCATGCC AATGTAAGCT ATTTTGTGGA

1041 ATTACGTTCA TGTTGGTTCT TATCTTGATA CAGTAAATCT

1081 CTTGATCATT ATTTATTGAG GAAAGTAAGC ATGTATGAAT

1121 TCACTTCCAC TATTCTTTAT AAGATAAGTT TTTGCACTCT

1161 ATC
```

The SEQ ID NO:12 nucleic acid from encodes a *Populus trichocarpa* polypeptide reported to have no known function, but with 74% sequence identity to SEQ ID NO:2. The polypeptide encoded by the SEQ ID NO:12 nucleic acid has accession number XP_002313939.1 (GI:224105811) in the NCBI database, and the following sequence (SEQ ID NO:13).

```
  1 MSRRPGNPAR RLADGGSLPF AGSMHSKSRS SPLLSIGLVV

41 VGAILLIGYC YSGSGGHITN REALSKTEGG VSCTLEVQRA

81 IPFLKKAYGD SMRKVLHVGP DTCSAVSSLL KEEDTEAWGV

121 EPYDLDDVSA NCKSLVRKGL VRVADIKFPL PYRPKSFSLV

161 IVSDALDYLS PKYLNKTLPE LARVSADGLV VFSGAPGQQR

201 VKVAELSKFG RPAKFRTSTW WIRYFVQTGL QENESALKKF

241 EQAALKKSYK PACQVFHLQS YD
```

*Ricinus communis* also has a nucleic acid with sequence homology to SEQ ID NO:1. This *Ricinus communis* sequence has accession no. XM_002530557.1 (GI: 255579520) in the NCBI database and is provided below as SEQ ID NO:14.

```
  1 ATGTCAAGGA GGCAAGTTAG CTCCACTCGT AGATTTGTGG

41 ACACAGGAAA TTTTCCTTTT TCAGGAGCAC TTCAAGCTAA

81 ATCTCGTTCT TCTCCTTTCT TATCTGTTGC CCTTATCCTT

121 CTGGGAGCAA TCCTTCTTAT CGCCTATGCT TATGGTGGTC

161 ATGGTGACTT TCATGTACC CTAGAAGTCC AGAGAACCAT

201 TCCCCTTTTA AAGAAAGCAT ATGGTGACAG TATGCGCAAG

241 GTTTTGCATG TGGGCCCTGA TACTTGTTCA GTCGTCTCTC

281 AATTGTTGAA AGAAGAAGAA ACTGAAGCAT GGGGTGTTGA

321 ACCATATGAT ATAGAGGATG CAGATGCAAA CTGCAAGAAT

361 TCTATCCGTA AAGGCATTGT TCGTGTCGCT GATATTAAGT

401 TCCCTCTGCC TTACAGGACG AAGTCATTCT CTCTTGTTAT

441 TGTGTCAGAT GCACTTGATT ACCTATCCCC AAAATACCTG

481 AACAGGACAC TTCCAGAGTT GGCAAGGGTG GCTGCTGATG

521 GTCTTGTTAT TTATGCAGGT TACCCTGGAC AACAGAGAGC
```

```
561 TAAAGTTGCA GAATTGTCTA AATTTGGACG ACCGGCCAAA

601 ATGAGGAGCT CGTCCTGGTG GGTTCGGTTT TTTGTCCAGA

641 CAAGCATAGA AGAAAATGAA ACTGCTATGA AGAAGTTTGA

681 GCAGGCTATA TCCAAGAAGT CATACAAGCC AACCTGCCAA

721 GTGTTCCACT TGAAGCCATA CCATTAG
```

The SEQ ID NO:14 nucleic acid from encodes a *Ricinus communis* polypeptide reported to have no known function, but with 75% sequence identity to SEQ ID NO:2. The polypeptide encoded by the SEQ ID NO:14 nucleic acid has accession number XP_002530603.1 (GI:255579521) in the NCBI database, and the following sequence (SEQ ID NO:15).

```
  1 MSRRQVSSTR RFVDTGNFPF SGALQAKSRS SPFLSVALIL
 41 LGAILLIAYA YGGHGDFSCT LEVQRTIPLL KKAYGDSMRK
 81 VLHVGPDTCS VVSQLLKEEE TEAWGVEPYD IEDADANCKN
121 SIRKGIVRVA DIKFPLPYRT KSFSLVIVSD ALDYLSPKYL
161 NRTLPELARV AADGLVIYAG YPGQQRAKVA ELSKFGRPAK
201 MRSSSWWVRF FVQTSIEENE TAMKKFEQAI SKKSYKPTCQ
241 VFHLKPYH
```

*Glycine max* also has a nucleic acid with sequence homology to SEQ ID NO:1. This *Glycine max* sequence has accession no. NM_001253246 (XM_003545720) in the NCBI database and is provided below as SEQ ID NO:16.

```
  1 GAGAGTCTGT TTCGGTCACA GCAGAGCAGA GAGTAGTAAG
 41 AAGACACTGC ACAGATCTGA GTGGTGACTG AAGGAATCTA
 81 GCTTCTTTCA TTTCTCATCA CTATTCTTAG GTCTGAGGGC
121 TCATTGCCAT TATCATGTCA AGGAGGCCAG TAAATCCTTC
161 GCGTCGGTTA GGTGATGGTG GAAGTATACC ATTTGCTGCA

201 TCTATCCGGT CTAAATCTCA AAACTCTCCC CTACTATCTA
241 TTGGGCTTGT CATTGTGGGT GCAATCCTTC TGATTGGTTA
281 TTGTTACAGC AATTCAGGTG GAGCTAGCGG TGGTATTAAG
321 GATGTAAGTA AACTTGAAGG TGGTGCATCA TGCTCATCAG
361 AAGTCCTACA AGCATTGCCC GTTTTGAAGA AATCATATGG
401 AGACAGTTTG CACAAGGTTT TGCATGTTGG CCCTGACTCT
441 TGTTCTGTGT TATCTAGTTT GTTAGAAGAA GAGGATACTG
481 AGGCTTGGGG AATAGAACCA TATGAGTTAG ATGATGTTGG
521 TGCAAAGTGT AAAAGTCTTG TACGCAAGGG CATTGTGCGT
561 GTGGCTGATT TGAAGTTTTC TCTACCCTAC CGTGCAAAGT
601 CATTTTCTCT GGTTATTGTG TCAGATGCAT TGGATTACTT
641 ATCTCCAAGA TACCTGAATA AAACCCTGCC AGAGTTGGTG
681 AGGGTGTCTG CTGATGGTGT TGTTATCTTT GCAGGTTATC
```

-continued

```
 721 CAGGTCAACA GAGAACTAGA GGTGAAGAAG TGGCCAAATT
 761 TGGTCGTCCA GCCAAATTGC GCAGCTCATC TTGGTGGATA
 801 AGGTTTTTCG TTCAGTCTAG TTTAGATGAA AATGAAACTG
 841 CTGGAAAGAA GTTTGAACAG GCTTCAGCCA AGAAGGCATA
 881 CAAGCCAGCA TGCCAAATTT TTCACCTCAA ATCATACCCT
 921 TGAAATTTCA CTGTCTTATT TGTATACTCC ACTTAATGGT
 961 TAGAAGCCAT GCTGATGAGA TAGGCATCTT CAGCACCCGA
1001 AGGGTAAAGT TCCATATATG CTGTTGAAAT TATAGTTCGA
1041 TGGTGATGAC ATATTTTATT TAGATTCAAT TATTAAACTA
1081 TTTTTGTCTT GGATAGTGTT CCTCATGTTT TTGTATTCAC
1121 AACTGCTATT TATTATTTAG AAAAATTTCT AATTTGACAC
1161 GAAAAAAAAA AAAAAAAAA
```

The SEQ ID NO:16 nucleic acid from encodes a *Glycine max* polypeptide reported to have no known function, but with 68% sequence identity to SEQ ID NO:2. The polypeptide encoded by the SEQ ID NO:16 nucleic acid has accession number NP_001240175.1 (GI:358248664) in the NCBI database, and the following sequence (SEQ ID NO:17).

```
  1 MSRRPVNPSR RLGDGGSIPF AASIRSKSQN SPLLSIGLVI
 41 VGAILLIGYC YSNSGGASGG IKDVSKLEGG ASCSSEVLQA
 81 LPVLKKSYGD SLHKVLHVGP DSCSVLSSLL EEEDTEAWGI
121 EPYELDDVGA KCKSLVRKGI VRVADLKFSL PYRAKSFSLV
161 IVSDALDYLS PRYLNKTLPE LVRVSADGVV IFAGYPGQQR
201 TRGEEVAKFG RPAKLRSSSW WIRFFVQSSL DENETAGKKF
241 EQASAKKAYK PACQIFHLKS YP
```

Sequences for CGR3 nucleic acids and proteins are available from the arabidopsis.org website. For example, one cDNA sequence for CGR3 from *Arabidopsis thaliana* has accession number At5g65810.1 and is provided below as (SEQ ID NO:18).

```
  1 GCGTTTGAGA GCAGAGCACT CGATAATTAA CACTAGGGAC
 41 GAAGAAGCTC TCGTTTAGTA AATTTTAGCT TAGAACACAG
 81 AAGAAGCATT TTTTCGGATC TGAGATCTTT AGATCCGAAC
121 ATCGTTTATT TCAAATCGTT TATTCAAGGT CTAAAAAAAA
161 GTTTTGAAGA ATCATAGCCA TGTCAAGAAG GCAAGTAAGG
201 CGTGTAGGGG ATAGTGGAAG CTTCCCATTT GTAGGAGCTC
241 TGCATTCAAA ATCACGTTCG TCTCCTCTGT TATCAGTTTG
281 CCTTGTTCTC GTGGGAGCAT GCCTTCTCAT TGGTTATGCT
321 TACAGTGGTC CAGGTATGTT CAAAAGTATC AGAGAAGTCA
361 GCAAGATTAC AGGTGACTAT TCTTGCACAG CAGAAGTTCA
401 AAGAGCCATT CCTATTCTTA AGAGTGCGTA TGGAGATAGC
441 ATGCGCAAAG TCCTGCACGT GGGTCCTGAA ACATGCTCAG
```

```
 481  TGGTCTCGAG TCTGTTGAAT GAAGAAGAGA CAGAAGCATG
 521  GGGTGTTGAA CCATATGATG TGGAGGATGC AGACTCTAAC
 561  TGCAAAAGTC TTTTGCACAA GGGCCTTGTA CGTGTGGCTG
 601  ACATCAAATT CCCTCTTCCT TACCGGTCAA AGTCGTTTTC
 641  TCTTGTGATC GTCTCAGACG CTTTGGATTA CCTCTCACCC
 681  AGGTACCTGA ACAAAACTGT GCCTGAACTT GCTCGCGTCG
 721  CTTCAGATGG TGTCGTTCTT TTAGCAGGTA ACCCTGGTCA
 761  ACAAAGGCT AAAGGTGGGG AATTGTCGAA ATTTGGACGG
 801  CCTGCTAAAA TGCGTAGCTC GTCGTGGTGG ATCCGTTTCT
 841  TCTCACAGAC GAACTTAGAG GAAAACGAAG CAGCAAGCAA
 881  GAAATTCGAA CAAGCAGCTT CCAAGAGTTC ATACAAACCA
 921  GCTTGTCAAG TTTTCCACCT CAAGCCATTA CATTAGTACA
 961  CACTATTATT ACTGGTCTTA AGACATCAAA CCAGATATCT
1001  CTCCTCTCTG TTTAATACCC TTTTTTTCCG CTATAGAAAG
1041  AAACTAAACT CCCACAAATT GTAATTCATT CTCAACGATT
1081  TGATTCATAA TTTAACTATT TAATAAATTT GCCTCTTCTC
1121  TACA
```

The SEQ ID NO:18 nucleic acid encodes a *Arabidopsis thaliana* CGR3 polypeptide with the following amino acid sequence (SEQ ID NO:19).

```
  1  MSRRQVRRVG DSGSFPPFVGA LHSKSRSSPL LSVCLVLVGA
 41  CLLIGYAYSG PGMFKSIREV SKITGDYSCT AEVQRAIPIL
 81  KSAYGDSMRK VLHVGPETCS VVSSLLNEEE TEAWGVEPYD
121  VEDADSNCKS LLHKGLVRVA DIKFPLPYRS KSFSLVIVSD
161  ALDYLSPRYL NKTVPELARV ASDGVVLLAG NPGQQKAKGG
201  ELSKFGRPAK MRSSSWWIRF FSQTNLEENE AASKKFEQAA
241  SKSSYKPACQ VFHLKPLH
```

The CGR3 protein has a methyltransferase domain (PF08241) that includes amino acids 146-188 of SEQ ID NO:19 sequence (underlined and in bold in the SEQ ID NO:19 sequence shown above). In some instances the *Arabidopsis thaliana* CGR3 polypeptide has an alanine at position 200 instead of a glycine.

*Arabidopsis lyrata* (subsp. *lyrata*) has a nucleic acid sequence with sequence homology to SEQ ID NO:18. This *Arabidopsis lyrata* sequence has accession no. XM_002877649.1 (GI:297819623) in the NCBI database and is provided below as SEQ ID NO:20.

```
  1  ATATTAACAC TTCGAAGCTT CTTCTTCATT TTAAGTAAAT
 41  TCAAGTGGAG GTGTTTATTC ATAAAGTGCT CATTTTCTCG
 81  GATCTCAGAT CTTAGATCCA AACCCTCTTC GTTTCATTGA
121  TCCAAGATCT AATAGCTTGA GCTTGTGGGG ATTTTAGTTA
161  TGGCGAGACG GCAAGTAGGT TCAACAAGAC GTGTAGGAGA
201  TGGTGGAAGC TTCCCGTTTG CAGGAGCTTT GCATTCAAAG
241  TCTCGATCTT CTCCACTACT CTCTATTTGC CTTGTTCTTG
281  TGGGGGCTTG CCTTCTCATT GGTTATGCTT ACAGTGGTCC
321  TGGAATCTTT AAAAGTATCA AAGAAGTCAG CAAAGTTACA
361  GGTGACTATT CTTGCACAGC AGAAGTCCAA AGAGCCATTC
401  CTGTTCTTAA GAAGGCTTAT GGAGATGGCA TGCGCAAAGT
441  CTTGCATGTG GGCCCTGACA CATGCTCAGT GGTTTCCAGT
481  CTACTGAAAG AAGAAGAGAC TGAAGCATGG GGTGTTGAAC
521  CATATGACAT CGAGGATGCA GATTCTCACT GCAAGAGTTT
561  TGTGAGCAAA GGCCTTGTAC GTGTGGCTGA TATCAAGTTC
601  CCTCTGCCCT ACCGGGCAAA ATCTTTCTCT CTTGTGATTG
641  TGTCAGATGC TCTGGATTAT CTCTCACCCA AGTACCTGAA
681  CAAGACTGTG CCTGAACTCG CAAGGGTGGC TTCAGACGGT
721  GTTGTTCTTT TTGCAGGTCT CCCTGGTCAG CAGAGAGCTA
761  AAGTTGCTGA ACTGTCTAAA TTTGGCCGAC CCGCTAAAAT
801  GCGTAGTGCA TCGTGGTGGA ACCGCTTTTT CGTCCAGACA
841  AACTTAGAAG AAAACGAAGC ACCAAGCAAG AAGTTCGATC
881  AGGCTGTTTC CAAAGGATTA TACAAACCAG CCTGCCAAGT
921  CTTCCACCTC AAGCCATTAC ATTAACCAGC CACCACCAAG
961  CCTATTGGGT CCACACCAAA GCATATTTAC ACGTAGAGCC
1001  GCACGCAAAA AAAAAAAATA GCGTAATCGA TATTCTCCTT
1041  GTATTTGTA ACAGGTCAGT TTTTATCCTT CAATGTTGTA
1081  TCCGTCAACA CAATTTTTCC TATTCAATTA AATCATAATT
1121  ATTATCACC
```

The SEQ ID NO:20 nucleic acid from encodes a *Arabidopsis lyrata* polypeptide reported to have no known function, but with 87% sequence identity to SEQ ID NO:19. The polypeptide encoded by the SEQ ID NO:20 nucleic acid has accession number XP_002877695.1 (GI:297819624) in the NCBI database, and the following sequence (SEQ ID NO:21).

```
  1  MARRQVGSTR RVGDGGSFPF AGALHSKSRS SPLLSICLVL
 41  VGACLLIGYA YSGPGIFKSI KEVSKVTGDY SCTAEVQRAI
 81  PVLKKAYGDG MRKVLHVGPD TCSVVSSLLK EEETEAWGVE
121  PYDIEDADSH CKSFVSKGLV RVADIKFPLP YRAKSFSLVI
161  VSDALDYLSP KYLNKTVPEL ARVASDGVVL FAGLPGQQRA
201  KVAELSKFGR PAKMRSASWW NRFFVQTNLE ENEAPSKKFD
241  QAVSKGLYKP ACQVFHLKPL H
```

*Solanum lycopersicum* has a nucleic acid sequence with sequence homology to SEQ ID NO:18. This *Solanum lycopersicum* sequence has accession no. XM_004230618.1 (GI:460369641) in the NCBI database and is provided below as SEQ ID NO:22.

```
   1 AATCTATGGC ATAAAGTTGG AGGAGTTATT TTATTTTCCC
  41 TCTACAGATT CCCCAACACA GACGACACAG TTACTACTAG
  81 CAAAACCAAA GGAAGCAGAT CCAGATCCCA CCTTCATCCT
 121 CAAGATCTCG ATCTCACTTC ACACTGATTG TTCAACCCAG
 161 TTATTACTAC TTGTCAATAT GTCAAGAAGG CCAACTCGCC
 201 GCTTTGCAGA TGCTGGTAGT ATTCCATTTG TGGGCTCCTT
 241 GCACCCCAAA TCACGTCCAT CTCCTTTATT GTCCTTAGGA
 281 CTTGTTTTGG GTGCATTGCT GATCATTGGT TACGTATATC
 321 ATAGTTCAGG TGGAAGAAGT GCAGCAGATG CTTTTAGTAG
 361 ACTTGAAGGT GGTACTTCAT GCACAGCGGA GCTTCACAGA
 401 GCATTACCTG TACTGAAGAA AGCATATGGG GATAACATGC
 441 GGAAAGTGTT GCACGTAGGC CCTGACACTT GTTCAGTGGT
 481 CTCTAATCTA TTAAAAGAAG AGGATACTGA AGCTTGGGGC
 521 ATTGAACCAT ATGATTTAGA TGAAACTGAT AGCAACTGCA
 561 AGGCTCTTGT TCACAAAGGG ATTGTTCGAG TAGCCGATGT
 601 TAAATTTCCT CTCCCCTACC GTTCAAAGTC GTTCTCTCTA
 641 GTCATAGTAT CTGATGCAGT GGATTACTTG TCTCCAAGAT
 681 ACCTTAACAA AACTATTCCA GAGTTGGCAA GGGTGGCTGC
 721 TGATGGATTA GTTATTTTAT CTGGTTACCC TGGTCAGCAA
 761 AAGGTTAAAG GAGCGGAGCT GTCAAAATTT GGCCGGCCAG
 801 CCAAATTGCG GAGCTCGTCC TGGTGGATTA GATTTTTCAT
 841 TCAAACCAGC TTAGAAGAGA ATGAACCTGT AACTAAGAAA
 881 TTTGAACAAG CAGCAGCCAA GAGGTCTTAC AAGCCAGCCT
 921 GCCAAGTTTT CCACCTCAAG CCACTTCTTT GATAATAAAA
 961 CACCAACTCT GTTTAAAAGA TGCTTAGCGT CTTCAGCTGT
1001 GTATTAAATG ACATGCTCCA AGTTCTGAAA AGTTGACAAT
1041 TTTTGTTGGA GGAAGTTGTT TCTGTATGAT AGGTTTCACA
1081 AGTAATGTAT AATAGGCTAG GAGCTTGCTG TCAATTGATA
1121 TTGCTCCTTG TAACTGCAAA CATAGCTGGT TTTAGCATGT
1161 CCAGACCAAA AACATTGTTT GAGAATTAGT ACTGTATAAG
1201 CTAAGATCAA TAAGTAATTT ATGATCTTTT TGCTGTCATA
1241 TTGTGTACTC TCTGGTTCAT CTGAAATTAA GTATCTGTTT
```

The SEQ ID NO:22 nucleic acid from encodes a *Solanum lycopersicum* polypeptide reported to have no known function, but with 74% sequence identity to SEQ ID NO:19. The polypeptide encoded by the SEQ ID NO:22 nucleic acid has accession number XP_004230666.1 (GI:460369642) in the NCBI database, and the following sequence (SEQ ID NO:23).

```
   1 MSRRPTRRFA DAGSIPFVGS LHPKSRPSPL LSLGLVLGAL
  41 LIIGYVYHSS GGRSAADAFS RLEGGTSCTA ELHRALPVLK
  81 KAYGDNMRKV LHVGPDTCSV VSNLLKEEDT EAWGIEPYDL
 121 DETDSNCKAL VHKGIVRVAD VKFPLPYRSK SFSLVIVSDA
 161 VDYLSPRYLN KTIPELARVA ADGLVILSGY PGQQKVKGAE
 201 LSKFGRPAKL RSSSWWIRFF IQTSLEENEP VTKKFEQAAA
 241 KRSYKPACQV FHLKPLL
```

*Prunus persica* has a polypeptide sequence with 74% sequence identity to SEQ ID NO:19. This *Prunus persica* sequence has accession no. EMJ01787.1 (GI:462395988) in the NCBI database and is provided below as SEQ ID NO:24.

```
   1 MSRRPVNPAR RIGDGGSIPF VGVVQSKARS SPLLSIGLVL
  41 VGAILLVCYA FSGSGGRSSK EAVIKLEGGA SCTFEVQRAI
  61 PILKKAYGDS MKKVLHVGPD TCSVVSKLLK EEDTEAWGVE
 121 PFDLEDADAN CKSLVSKGIV RAADIKFSLP YRPKSFSLVI
 161 ASDALDYLSP KYLNKTLPEL ARVSADGVVI FTGYPGQHKA
 201 KVAELSKFGR PAKLRSSSWW IRYFVQTSLE ENEVASKKFE
 241 QAALKKSYTP ACQVFHLKSY H
```

The QUA2 gene and protein are discussed herein as being a related methyltransferase. The amino acid sequence for an *Arabidopsis thaliana* QUA2 protein is available from the Arabidopsis.org website with accession number AT1G78240.1. The sequence of this *Arabidopsis thaliana* QUA2 protein is shown below as SEQ ID NO:25.

```
   1 MSMPLQRGIS GVRVSDSSDD LRDSQMKDKT ERARSTENNN
  41 LTLRFPFGFL FSNQSSSKHG GGGENGFSAD PYSARSRHRL
  81 MLLFLKISLV LIVVIALAGS FWWTISISTS SRGHVYHNYR
 121 RLQEQLVSDL WDIGEISLGP NRWKELEYCN IESENFVPCF
 161 NVSENLALGY SNGDENDRFC GPGSKQECLE LPPVKYRVPL
 201 RWPTGKDIIW HSNVKITAQE VVSSGSITKR MMMMEDDQIS
 241 FRSASPMSDE VEDYSHQIAE MIGIKKDNFI EAGVRTILDI
 281 GCGYGSFGAH LLSKQILTMC IANYEASGSQ VQLTLERGLP
 321 AMIGSFISKQ LPYPSLSFDM LHCLRCGIDW DQKDGLLLVE
 361 IDRVLKPGGY FVWTSPLTNP RNKDHLKRWN FVHDFAESIC
 401 WTLLNQQDET VVWKKTINTK CYSSRKPGVG PSVCTKGHDV
 441 ESPYYRPLQM CIGGTRSRRW IPIEGRTRWP SRSNMNKTEL
 481 SLYGLHPEVL GEDAENWKIT VREYWSLLSP LIFSDHPKRP
 501 GDEDPSPPYN MLRNVLDMNA QFGGLNSALL EARKSVWVMN
 551 VVPTAGPNHL PMILDRGFVG VLHNWCEPFP TYPRTYDLVH
 601 ADNLLSLQTS QPRKTCLLID IFTEIDRLLR PEGWVIIRDT
 641 AQLVEKARET ITQLKWEARV IEVESSSEQR LLICQKPFTK
 681 RQSI
```

QUA2 contains a putative methyltransferase domain (DUF248), while CGR2 and CGR3 have a putative methyltransferase domain (PF08241) different from DUF248 domain that is commonly found in QUA2 like proteins.

CGR2 and CGR3 nucleic acids and polypeptides allow identification and isolation of related nucleic acids and their encoded enzymes that provide a means for production of plants with increased homogalacturonan methyl-esterification.

The related nucleic acids can be isolated and identified by mutation of the SEQ ID NO:1, 3, 4, 6, 8, 10, 12, 14, 16, 18, 20 or 22 nucleic acid sequences and/or by hybridization to DNA and/or RNA isolated from other plant species using segments of these nucleic acids as probes. The sequence of the CGR2 and CGR3 enzymes (e.g., SEQ ID NO:2, 5, 7, 9, 11, 13, 15, 17, 19, 21, 23 or 24) can also be examined and used a basis for designing alternative CGR2 or CGR3 nucleic acids that encode related CGR2 or CGR3 methyltransferase polypeptides.

The CGR2 and CGR3 nucleic acids of the invention can include any nucleic acid that can selectively hybridize to any of SEQ ID NO: 1, 3, 4, 6, 8, 10, 12, 14, 16, 18, 20, or 22.

The term "selectively hybridize" includes hybridization, under stringent hybridization conditions, of a nucleic acid sequence to a specified nucleic acid target sequence (e.g., any of the SEQ ID NO:1, 3, 4, 6, 8, 10, 12, 14, 16, 18, 20, or 22) to a detectably greater degree (e.g., at least 2-fold over background) than its hybridization to non-target nucleic acid sequences. Such selective hybridization substantially excludes non-target nucleic acids. Selectively hybridizing sequences can have less than 100% sequence identity to any of the CGR2 and CGR3 nucleic acids described herein.

The CGR2 and CGR3 nucleic acids and the CGR2 and CGR3 polypeptides useful for increasing plant biomass and/or for increasing plant biomass digestibility typically have about at least 40% sequence identity, or at least 50% sequence identity, or at least 60% sequence identity, or at least 70% sequence identity, or at least 80% sequence identity, or at least 85% sequence identity, or at least 90% sequence identity, or at least 95% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with each other. In some embodiments, a selectively hybridizing sequence has about at least about 80% sequence identity or complementarity with SEQ ID NO:1, 3, 4, 6, 8, 10, 12, 14, 16, 18, 20, or 22.

Thus, the nucleic acids of the invention include those with about 500 of the same nucleotides as SEQ ID NO:1, 3, 4, 6, 8, 10, 12, 14, 16, 18, 20, or 22, or about 600 of the same nucleotides, or about 700 of the same nucleotides, or about 800 of the same nucleotides, or about 900 of the same nucleotides, or about 1000 of the same nucleotides, or about 1100 of the same nucleotides, or about 1200 of the same nucleotides as SEQ ID NO:1, 3, 4, 6, 8, 10, 12, 14, 16, 18, 20, or 22. The identical nucleotides or amino acids can be distributed throughout the nucleic acid or the protein, and need not be contiguous.

Note that if a value of a variable that is necessarily an integer, e.g., the number of nucleotides or amino acids in a nucleic acid or protein, is described as a range, e.g., 90-99% sequence identity what is meant is that the value can be any integer between 90 and 99 inclusive, i.e., 90, 91, 92, 93, 94, 95, 96, 97, 98 or 99, or any range between 90 and 99 inclusive, e.g., 91-99%, 91-98%, 92-99%, etc.

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified with up to 100% complementarity to the probe (homologous probing). Alternatively, stringency conditions can be adjusted to allow some mismatching in sequences so that lower degrees of sequence similarity are detected (heterologous probing). The probe can be approximately 20-500 nucleotides in length, but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length.

Typically, stringent conditions will be those where the salt concentration is less than about 1.5 M $Na^+$ ion (or other salts), typically about 0.01 to 1.0 M $Na^+$ ion concentration (or other salts), at pH 7.0 to 8.3 and the temperature is at least about 30° C. for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution. Thus, high stringency conditions can include a wash in 0.1×SSC at 60 to 65° C.

For DNA-DNA hybrids, the $T_m$ can be approximated from the equation of Meinkoth and Wahl (Anal. Biochem. 138: 267-84 (1984)):

$$T_m = 81.5° \text{ C.} + 16.6(\log M) + 0.41(\% \ GC) - 0.61(\% \text{ formamide}) - 500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to any of SEQ ID NO:1, 3, 4, 6, 8, 10, 12, 14, 16, 18, 20, or 22.

Those of skill in the art also understand how to vary the hybridization and/or wash solutions to isolate desirable nucleic acids. For example, if the desired degree of mismatching results in a $T_m$, of less than 45° C. (aqueous solution) or 32° C. (formamide solution), it may be preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

Unless otherwise stated, in the present application high stringency is defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C. However, because specificity is typically a function of post-hybridization washes, where the factors controlling hybridization include the ionic strength and temperature of the final wash solution, the high stringency conditions can more simply be expressed as including a wash in 0.1×SSC at 60 to 65° C.

The following terms are used to describe the sequence relationships between two or more nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. The reference sequence can be a nucleic acid sequence (e.g., any of SEQ ID NO:1, 3, 4, 6, 8, 10, 12, 14, 16, 18, 20, or 22) or an amino acid sequence (e.g., any of SEQ ID NO: 2, 5, 7, 9, 11, 13, 15, 17, 19, 21, 23 or 24). A reference sequence may be a subset or the entirety of a specified sequence. For example, a reference sequence may be a segment of a full-length cDNA or of a genomic DNA sequence, or the complete cDNA or complete genomic DNA sequence, or a domain of a polypeptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 20 contiguous nucleotides in length, and optionally can be 30, 40, 50, 100 or more nucleotides. For amino acid sequences, the comparison window is at least about 10 amino acids, and can optionally be 15, 20, 30, 40, 50, 100 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may permit optimal alignment of compared sequences; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. An example of a good program to use for optimal global alignment of multiple sequences is PileUp (Feng and Doolittle, (1987) J. Mol. Evol., 25:351-60, which is similar to the method described by Higgins and Sharp, (1989) CABIOS 5:151-53 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or more.

GAP presents one member of the family of best alignments. There may be many members of this family. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

For example, sequence identity/similarity values provided herein can refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU ($C_1$-ayerie and States, (1993) Comput. Chem. 17:191-201) low-complexity filters can be employed alone or in combination.

The terms "substantial identity" indicates that a polypeptide or nucleic acid comprises a sequence with between 55-100% sequence identity to a reference sequence, with at least 55% sequence identity, or at least 60%, or at least 70%, or at least 80%, or at least 90% or at least 95% sequence identity, or any percentage value within the range of 55-100% sequence identity relative to the reference sequence over a specified comparison window. Optimal alignment may be ascertained or conducted using the homology alignment algorithm of Needleman and Wunsch, supra.

One indication that two polypeptide sequences are substantially identical is that both polypeptides have methyltransferase activity with homogalacturonan as a substrate. The polypeptide that is substantially identical to a CGR2 or CGR3 with a SEQ ID NO: 2, 5, 7, 9, 11, 13, 15, 17, 19, 21, 23 or 24 sequence may not have exactly the same level of activity as the CGR2 or CGR3 methyltransferase with a SEQ ID NO: 2, 5, 7, 9, 11, 13, 15, 17, 19, 21, 23 or 24. Instead, the substantially identical polypeptide may exhibit greater or lesser levels of methyltransferase activity than the CGR2 or CGR3 with SEQ ID NO: 2, 5, 7, 9, 11, 13, 15, 17, 19, 21, 23 or 24, as measured by assays available in the art or described herein (see, e.g., the Examples). For example, the substantially identical polypeptide can have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the activity of the CGR2 or CGR3 methyltransferase with the SEQ ID NO: 2, 5, 7, 9, 11, 13, 15, 17, 19, 21, 23 or 24 sequence when measured by similar assay procedures.

Alternatively, substantial identity is present when second polypeptide is immunologically reactive with antibodies raised against the first polypeptide (e.g., a polypeptide with SEQ ID NO: 2, 5, 7, 9, 11, 13, 15, 17, 19, 21, 23 or 24). Thus, a polypeptide is substantially identical to a first polypeptide, for example, where the two polypeptides differ only by a conservative substitution. In addition, a polypeptide can be substantially identical to a first polypeptide when they differ by a non-conservative change if the epitope that the antibody recognizes is substantially identical. Polypeptides that are "substantially similar" share sequences as noted above except that some residue positions, which are not identical, may differ by conservative amino acid changes.

The CGR2 or CGR3 polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 N-terminal amino acid residues of a the SEQ ID NO:2, 5, 7, 9, 11, 13, 15, 17, 19, 21, 23 or 24 sequence. Alternatively, the CGR2 or CGR3 polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 C-terminal amino acid residues of the SEQ ID NO:2, 5, 7, 9, 11, 13, 15, 17, 19, 21, 23 or 24 sequence.

Plants Modified to Express or Contain CGR2 or CGR3

In order to engineer plants with highly methyl-esterified homogalacturonan one of skill in the art can introduce CGR2 or CGR3, or nucleic acids encoding such CGR2 or CGR3 methyltransferases into the plants. Introduction of CGR2 or CGR3, or expression of increased levels of CGR2 or CGR3, in a plant can increase the plant's biomass by 5% or more. For example, introduction of CGR2 or CGR3, or expression of increased levels of CGR2 or CGR3, in a plant can increase the plant's biomass by at least 10%, or at least 15%, or at least 20%, or at least 25%, or at least 30%, or at least 33%, or at least 50%, or at least 100% compared to a wild type plant of the same species that does not comprise the CGR2 expression cassette or the CGR3 expression cassette. The amount of fermentable sugars that can be obtained from such a plant biomass that heterologously expresses CGR2 or CGR3 can be increased by at least 25%, or at least 30%, or at least 33%, or at least 50%, or at least 100%, or at least 200% compared to a wild type plant of the same species that does not heterologously express CGR2 or CGR3 (e.g., from a CGR2 expression cassette and/or a CGR3 expression cassette).

For example, one of skill in the art can inject CGR2 or CGR3 methyltransferase enzymes into young plants.

Alternatively, one of skill in the art can generate genetically-modified plants that contain nucleic acids encoding CGR2 and/or CGR3 polypeptides within their somatic and/or germ cells. Such genetic modification can be accomplished by procedures available in the art. For example, one of skill in the art can prepare an expression cassette or expression vector that can express one or more encoded CGR2 and/or CGR3 methyltransferase enzymes. Plant cells can be transformed by the expression cassette or expression vector, and whole plants (and their seeds) can be generated from the plant cells that were successfully transformed with the CGR2 and/or CGR3 methyltransferase nucleic acids. Some procedures for making such genetically modified plants and their seeds are described below.

Promoters:

The CGR2 and/or CGR3 nucleic acids described herein can be operably linked to a promoter, which provides for expression of mRNA from the CGR2 or CGR3 methyltransferase nucleic acids. The promoter can be a heterologous promoter. The promoter is typically a promoter functional in plants and/or seeds, and can be a promoter functional during plant growth and development. A CGR2 or CGR3 methyltransferase nucleic acid is operably linked to the promoter when it is located downstream from the promoter, to thereby form an expression cassette.

Most endogenous genes have regions of DNA that are known as promoters, which regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired.

Expression cassettes generally include, but are not limited to, a plant promoter such as the CaMV 35S promoter (Odell et al., *Nature.* 313:810-812 (1985)), or others such as CaMV 19S (Lawton et al., *Plant Molecular Biology.* 9:315-324 (1987)), nos (Ebert et al., *Proc. Natl. Acad. Sci. USA.* 84:5745-5749 (1987)), Adh1 (Walker et al., *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)) or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kDa zein protein, a Z27 promoter from a gene encoding a 27 kDa zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan, *Proc. Natl. Acad. Sci. USA.* 83:3320-3324 (1985). Other promoters useful in the practice of the invention are known to those of skill in the art.

Alternatively, novel tissue specific promoter sequences may be employed in the practice of the present invention. cDNA clones from a particular tissue can be isolated and those clones which are expressed specifically in that tissue are identified, for example, using Northern blotting. Preferably, the gene isolated is not present in a high copy number, but is relatively abundant in specific tissues. The promoter and control elements of corresponding genomic clones can then be localized using techniques well known to those of skill in the art.

A CGR2 or CGR3 nucleic acid can be combined with the promoter by standard methods to yield an expression cassette, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The CGR2 or CGR3 nucleic acids can be subcloned downstream from the promoter using restriction enzymes and positioned to ensure that the DNA is inserted in proper orientation with respect to the promoter so that the DNA can be expressed as sense RNA. Once the CGR2 or CGR3 nucleic acid is operably linked to a promoter, the expression cassette so formed can be subcloned into a plasmid or other vector (e.g., an expression vector).

In some embodiments, a cDNA clone encoding a CGR2 or CGR3 protein is isolated from plant tissue, for example, a root, stem, leaf, seed, or flower tissue. For example, cDNA clones from selected species (that encode a CGR2 or CGR3 methyltransferase protein with homology to any of those described herein) are made from isolated mRNA from selected plant tissues. In another example, a nucleic acid encoding a mutant or modified CGR2 or CGR3 protein can be prepared by available methods or as described herein. For example, the nucleic acid encoding a mutant or modified CGR2 or CGR3 protein can be any nucleic acid with a coding region that hybridizes to a segment of a SEQ ID NO:1, 3, 4, 6, 8, 10, 12, 14, 16, 18, 20, and 22 nucleic acid. Such a nucleic acid can encode an enzyme with methyltransferase activity on a homogalacturonan substrate. Using restriction endonucleases, the entire coding sequence for the modified CGR2 or CGR3 methyltransferase is subcloned downstream of the promoter in a 5' to 3' sense orientation.

Targeting Sequences:

Additionally, expression cassettes can be constructed and employed to target the CGR2 or CGR3 proteins to an intracellular compartment within plant cells, into a membrane, or to direct an encoded protein to the extracellular environment. This can generally be achieved by joining a DNA sequence encoding a transit or signal peptide sequence to the coding sequence of the CGR2 or CGR3 methyltransferase nucleic acid. The resultant transit, or signal, peptide will transport the protein to a particular intracellular, or extracellular destination, respectively, and can then be post-translational removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

3' Sequences:

When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research.* 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology.* 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the CGR2 or CGR3 nucleic acids by standard methods.

Selectable and Screenable Marker Sequences:

In order to improve identification of transformants, a selectable or screenable marker gene can be employed with the expressible CGR2 or CGR3 methyltransferase nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Examples of proteins suitable for modification in this manner include extensin or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich wall proteins (Keller et al., *EMBO J.* 8:1309-1314 (1989)) could be modified by the addition of an antigenic site to create a screenable marker.

Numerous other possible selectable and/or screenable marker genes will be apparent to those of skill in the art in addition to those forth herein below. Therefore, it will be understood that the discussion herein is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Possible selectable markers for use in connection with the present invention include, but are not limited to, a neo gene (Potrykus et al., *Mol. Gen. Genet.* 199:183-188 (1985)) which codes for kanamycin resistance and can be selected for using kanamycin, G418, and the like; a bar gene which codes for bialaphos resistance; a gene which encodes an altered EPSP synthase protein (Hinchee et al., *Bio/Technology.* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death. The success in using this selective system in conjunction with monocots was surprising because of the major difficulties that have been reported in transformation of cereals (Potrykus, *Trends Biotech.* 7:269-273 (1989)).

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* 18th Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al.,

*Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995)).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, Pl. Alternatively any genotype of maize can be utilized if the C1 and R alleles are introduced together.

The R gene regulatory regions may be employed in chimeric constructs in order to provide mechanisms for controlling the expression of chimeric genes. More diversity of phenotypic expression is known at the R locus than at any other locus (Coe et al., in *Corn and Corn Improvement*, eds. Sprague, G. F. & Dudley, J. W. (Am. Soc. Agron., Madison, Wis.), pp. 81-258 (1988)). It is contemplated that regulatory regions obtained from regions 5' to the structural R gene can be useful in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, one that can be used is Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences:

An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, preferably encoding antibiotic or herbicide resistance, unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology.* 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes:

Once the expression cassette is constructed and subcloned into a suitable plasmid, it can be screened for the ability to substantially inhibit the translation of an mRNA coding for a seed storage protein by standard methods such as hybrid arrested translation. For example, for hybrid selection or arrested translation, a preselected antisense DNA sequence is subcloned into an SP6/T7 containing plasmids (as supplied by ProMega Corp.). For transformation of plants cells, suitable vectors include plasmids such as described herein. Typically, hybrid arrest translation is an in vitro assay that measures the inhibition of translation of an mRNA encoding a particular seed storage protein. This screening method can also be used to select and identify preselected antisense DNA sequences that inhibit translation of a family or subfamily of zein protein genes. As a control, the corresponding sense expression cassette is introduced into plants and the phenotype assayed.

DNA Delivery of the DNA Molecules into Host Cells:

The present invention generally includes steps directed to introducing CGR2 or CGR3 nucleic acids, such as a preselected cDNA encoding the CGR2 or CGR3 methyltransferase enzyme, into a recipient cell to create a transformed cell. In some instances, the frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells regenerated into transgenic plants, through the application of the techniques disclosed herein.

Another aspect of the invention is a plant with highly methyl-esterified homogalacturonan, wherein the plant has an introduced CGR2 or CGR3 nucleic acid. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. Suitable examples of plant species include grasses, softwoods, hardwoods, wheat, rice, *Arabidopsis*, tobacco, cucumber, tomato, maize, soybean, and the like. In some embodiments, the plant or cell is a monocotyledon plant or cell. For example, the plant or cell can be a softwood plant or cell, or a maize plant or cell. In some embodiments, the plant or cell is a dicotyledon plant or cell. For example, the plant or cell can be a hardwood plant or cell. The cell(s) may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods known to those of skill in the art. Examples are: Transformation by direct DNA transfer into plant cells by electroporation (U.S. Pat. No. 5,384,253 and U.S. Pat. No. 5,472,869, Dekeyser et al., *The Plant Cell*. 2:591-602 (1990)); direct DNA transfer to plant cells by PEG precipitation (Hayashimoto et al., *Plant Physiol*. 93:857-863 (1990)); direct DNA transfer to plant cells by microprojectile bombardment (McCabe et al., *Bio/Technology*. 6:923-926 (1988); Gordon-Kamm et al., *The Plant Cell*. 2:603-618 (1990); U.S. Pat. No. 5,489,520; U.S. Pat. No. 5,538,877; and U.S. Pat. No. 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227:1229-1231 (1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. No. 5,384,253; and U.S. Pat. No. 5,472,869). For example, embryogenic cell lines derived from immature *Zea mays* embryos can be transformed by accelerated particle treatment as described by Gordon-Kamm et al. (*The Plant Cell*. 2:603-618 (1990) or U.S. Pat. No. 5,489,520; U.S. Pat. No. 5,538,877 and U.S. Pat. No. 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Similar tissues can be transformed for softwood or hardwood species. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the CGR2 or CGR3 methyltransferase nucleic acids for an effective period of time. This may range from a less than one second pulse of electricity for electroporation to a 2-3 day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation:

Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment:

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium tumefaciens* containing plasmids with either the β-glucoronidase or bar gene engineered for expression in maize. Bacteria were inactivated by ethanol dehydration prior to bombardment. A low level of transient expression of the β-glucoronidase gene was observed 24-48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to it being an effective means of reproducibly stably transforming monocots, is that the isolation of protoplasts (Christou et al., *PNAS.* 84:3962-3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell.* 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here-in one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize:

After effecting delivery of a CGR2 or CGR3 nucleic acid to recipient cells by any of the methods discussed above, the transformed cells can be identified for further culturing and plant regeneration. As mentioned above, in order to improve the ability to identify transformants, one may desire to employ a selectable or screenable marker gene as, or in addition to, the expressible CGR2 or CGR3 nucleic acids. In this case, one would then generally assay the potentially transformed cell population by exposing the cells to a selective agent or agents, or one would screen the cells for the desired marker gene trait.

Selection:

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of *Zea mays* L. can be selected with sub-lethal levels of bialaphos. Slowly growing tissue was subsequently screened for expression of the luciferase gene and transformants can be identified.

Regeneration and Seed Production:

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·$m^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the CGR2 or CGR3 methyltransferase nucleic acids into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced CGR2 or CGR3 nucleic acids, the plant is self-pollinated at least once in order to produce a homozygous backcross converted inbred containing the CGR2 or CGR3 nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the CGR2 or CGR3 nucleic acids (or CGR2 or CGR3 enzyme). Transgenic plant and/or seed tissue can be analyzed for CGR2 or CGR3 expression using standard methods such as SDS polyacrylamide gel electrophoresis, liquid chromatography (e.g., HPLC) or other means of detecting a product of CGR2 or CGR3 activity (e.g., methyl-esterified homogalacturonan).

Once a transgenic seed expressing the CGR2 or CGR3 sequence and having an increase in methyl-esterification of homogalacturonan of the plant is identified, the seed can be used to develop true breeding plants. The true breeding plants are used to develop a line of plants with an increase in the percent of methyl-esterification in the homogalacturonan of the plant while still maintaining other desirable functional agronomic traits. Adding the trait of increased methyl-esterification in the homogalacturonan of the plant can be accomplished by back-crossing with this trait and with plants that do not exhibit this trait and studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of an increased percent of methyl-esterification in the homogalacturonan of the plant. The resulting progeny are then crossed back to the parent that expresses the increased CGR2 or CGR3 trait (more methyl-esterification). The progeny from this cross will also segregate so that some of the progeny carry the trait and some do not. This back-crossing is repeated until an inbred line with the desirable functional agronomic traits, and with expression of the trait involving an increase in methyl-esterification of the homogalacturonan of the plant. Such expression of the increased percentage of methyl-esterification in plant homogalacturonan can be expressed in a dominant fashion.

Subsequent to back-crossing, the new transgenic plants can be evaluated for an increase in the weight percent of methyl-esterification incorporated into the homogalacturonan of the plant. This can be done, for example, by immunofluorescence analysis of whole plant cell walls (e.g., by microscopy), methyltransferase activity assays, pectin analysis, and any of the assays described herein or available to those of skill in the art.

The new transgenic plants can also be evaluated for a battery of functional agronomic characteristics such as lodging, kernel hardness, yield, resistance to disease, resistance to insect pests, drought resistance, and/or herbicide resistance.

Plants that may be improved by these methods include but are not limited to oil and/or starch plants (e.g., canola, potatoes, lupins, sunflower and cottonseed), forage plants (e.g., alfalfa, clover and fescue), vegetable plants (e.g., cucumber, tomato), grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and *eucalyptus*). In some embodiments the plant is a gymnosperm. Examples of plants useful for pulp and paper production include most pine species such as loblolly pine, Jack pine, Southern pine, *Radiata* pine, spruce, Douglas fir and others. Hardwoods that can be modified as described herein include aspen, poplar, *eucalyptus*, and others. Plants useful for making biofuels and ethanol include corn, grasses (e.g., *miscanthus*, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues:

To confirm the presence of the CGR2 or CGR3 nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced CGR2 or CGR3 nucleic acids. PCR also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting and PCR may be used to detect the CGR2 or CGR3 nucleic acid in question, they do not provide information as to whether the preselected DNA segment is being expressed. Expression may be evaluated by specifically identifying the protein products of the introduced CGR2 or CGR3 nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the CGR2 or CGR3 such as evaluation by amino acid sequencing following purification. The Examples of this application also provide assay procedures for detecting and quantifying CGR2 or CGR3 transferase activity. Other procedures may be additionally used.

The expression of a gene product can also be determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

Release of Fermentable Sugars from Plant Biomass

Plant parts, components and biomass from plants expressing CGR2 and/or CGR3 can be converted into fermentable sugars using procedures available in the art. For example, the plant parts, components and biomass from plants expressing CGR2 and/or CGR3 can be dried and/or ground up so that the polysaccharides become accessible to enzymatic cleavage.

Effective enzyme mixtures for biomass deconstruction can have combined catalytic activities so that the enzymes can cleave substantially all saccharide linkages found in plant cell walls to release free, fermentable sugar residues. Such enzyme mixtures can often be derived from microorganisms. Many microorganisms that live in lignocellulose-rich environments secrete large numbers and broad ranges of cell wall-active enzymes, including, but not limited to, cellulases, hemicellulases, pectinases, and/or proteases. Most commercially available deconstruction enzyme mixtures contain between approximately twenty-five to one hundred and fifty (25-150) enzymes. Nagendran et al., *Fung. Genet. Biol.* 46: 427-435 (2009); Banerjee et al., *Bioresour. Technol.* 101: 9097-9105 (2010); and Scott-Craig et al., *J Biol Chem* 286:42848-42854 (2011). For example, commercial enzyme mixtures can be used that include hemicellulose degrading enzymes such as β-1,4-xylanase, β-xylosidase, α-arabinosidase, mixed-linked glucanase, α-glucuronidase, etc. Examples of commercial enzyme mixtures that can be employed to release fermentable sugars from plant biomass include Spezyme CP, Accellerase®1000, Multifect Xylanase, Cellic® CTec, CTec2, CTec3, Htec, HTec2, and HTec3, and AlternaFuel® CMAX.

Incubation of the plant biomass with the enzyme mixture can be performed at a temperature ranging from approximately 40° to approximately 60° C. In one embodiment, the incubation is performed at a pH ranging from approximately 4 to approximately 6.

Definitions

As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth.

In this document, the term "or" is used to refer to a nonexclusive or, such that "A or B" includes "A but not B," "B but not A," and "A and B," unless otherwise indicated.

In this document, the terms "including" and "in which" are used as the plain-English equivalents of the respective terms "comprising" and "wherein."

As used herein, the term "plant" is used in its broadest sense. It includes, but is not limited to, any species of grass (e.g. turf grass), ornamental or decorative, crop or cereal, fodder or forage, fruit or vegetable, fruit plant or vegetable plant, herb plant, woody plant, flower plant or tree. It is not meant to limit a plant to any particular structure. It also refers to a unicellular plant (e.g. microalga) and a plurality of plant cells that are largely differentiated into a colony (e.g. volvox) or a structure that is present at any stage of a plant's development. Such structures include, but are not limited to, a seed, a tiller, a sprig, a stolen, a plug, a rhizome, a shoot, a stem, a leaf, a flower petal, a fruit, et cetera.

As used herein, "isolated" means a nucleic acid or polypeptide has been removed from its natural or native cell. Thus, the nucleic acid or polypeptide can be physically isolated from the cell or the nucleic acid or polypeptide can be present or maintained in another cell where it is not naturally present or synthesized.

The term "transgenic" when used in reference to a plant or leaf or fruit or seed or plant biomass, for example a "transgenic plant," "transgenic leaf," "transgenic fruit," "transgenic fruit," "transgenic seed," "transgenic biomass," or a "transgenic host cell" refers to a plant or leaf or fruit or seed or biomass that contains at least one heterologous or foreign gene (such as an expression cassette) in one or more of its cells. The term "transgenic plant material" refers broadly to a plant, a plant structure, a plant tissue, a plant seed or a plant cell that contains at least one heterologous gene in one or more of its cells.

The term "transgene" refers to a foreign gene that is placed into an organism (e.g. a plant) or host cell by the process of transfection. The term "foreign gene" or heterologous gene refers to any nucleic acid (e.g., gene sequence) that is introduced into the genome of an organism or tissue of an organism or a host cell by experimental manipulations, such as those described herein, and may include gene sequences found in that organism so long as the introduced gene does not reside in the same location, as does the naturally occurring gene.

As used herein, a "native" nucleic acid or polypeptide means a DNA, RNA or amino acid sequence or segment that has not been manipulated in vitro, i.e., has not been isolated, purified, and/or amplified.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene. As used herein, the term "wild-type" when made in reference to a plant refers to the plant type common throughout an outbred population that has not been genetically manipulated to contain an expression cassette, e.g., an expression cassettes described herein.

The following non-limiting Examples illustrate how aspects of the invention have been developed and can be made and used.

Example 1: Materials and Methods

This Example describes some of the materials and methods used in developing the invention.

Cloning and Plant Transformation

The coding sequence of CGR2 was amplified using Pfu Ultra II HS fusion PCR (Stratagene) with the following primers:

```
CGR2-cCFP_FP (SEQ ID NO: 52):
5'-CAGGACGTCTAGATGGCGAGACGGCAAGTAGGTTC-AAC-3'
and CGR2-cCFP_RP (SEQ ID NO: 53):
5'-CATGACCGTCGACTTATGTAATGGCTTGAGGTGGAA-GAC-
3'.
```

The resulting PCR product was cloned into the pVKH18En6 vector containing a CaMV35S promoter and cCFP for the C-terminal fusion. The construct was introduced into GV3101 (*A. tumefaciens*), and transformations into *Arabidopsis* were performed by the Great Lakes Bioenergy Research Center Plant Transformation Facility (East Lansing, Mich.). The resulting transgenic plants were screened on MS medium supplemented with Gamborg's B5 vitamins (PhytoTechnology Laboratories) and hygromycin (20 μg mL$^{-1}$; Wisent).

The CGR3 protein coding sequence was amplified using the Cgr3-F and Cgr3-R primers by Pfu Ultra II HS fusion PCR (Stratagene) from cDNA prepared from wild-type Col-0 *Arabidopsis* seedlings. The sequences of the Cgr3-F and Cgr3-R primers are shown below.

```
Cgr3-F (SEQ ID NO: 54):
CAGGACGTCTAGATGTCAAGAAGGCAAGTAAGGCG

Cgr3-R (SEQ ID NO: 55):
CATGACCGTCGACTTATGTAATGGCTTGAGGTGGAAAAC
```

The purified PCR product was subcloned into the pVKH18En6 binary vector (Batoko et al., 2000) behind a CAMV 35S promoter for overexpression as a C-terminal cCFP fusion (Rizzo et al., 2004). DNA sequencing was performed to confirm in-frame ligation. *Agrobacterium tumefaciens* GV3101 was transformed with the resulting plasmid using the freeze-thaw method (An et al., 1988).

Confocal Analyses

Confocal laser scanning microscopy was performed on an inverted LSM 510 ZEISS META microscope. cCFP and YFP were excited with 458 nm and 514 nm argon laser respectively, and fluorescence emission was detected with 465~510 nm and 520~555 nm band pass emission filter, respectively. Image acquisition was performed with line switching mode. For immune-labeling analyses, fluorescent signal was recorded using a 488 nm argon laser lines for excitation and a 505 nm long-pass filter for emission. Propidium iodide stained samples were excited with a 594 nm HeNe laser line and the emitted fluorescence was detected with a 604~690 nm band pass emission filter.

Transient Expression in *Nicotiana tabacum*

Transient expression of CGR2-cCFP, CGR3-cCFP, and ManI-YFP in *N. tabacum* lower leaf epidermal cells was performed as described previously with slight modifications (Batoko et al., 2000). *Agrobacterium* culture was incubated for 18 hr at 28° C. with agitation, followed by centrifugation at 2,200×g to pellet cells. Cells were resuspended in the infiltration buffer (100 μM acetosyringone in 50 mM MES pH 5.7, 10 mM MgCl$_2$ and 5 mM Na$_3$PO$_4$). Plants grown under short-day (8 hours light) condition were infiltrated with *Agrobacterium* at OD$_{600}$=0.025, and images were obtained after 3 days post infiltration using confocal microscopy.

Topology Analysis

CGR2-cCFP and CGR3-cCFP expressing plants (CGR2OX and CGR3OX, respectively) were grown in liquid MS medium supplemented with Gamborg's B5 vitamins and 1% w/v sucrose for 4 weeks. Plants were homogenized as described previously (Held et al., 2011). The homogenates were centrifuged sequentially at 16K×g and 100K×g at 4° C. for 20 min. Pellets after the centrifugation at 100K×g were resuspended in 100 μL of 1×PBS and treated with 0.3 mg/ml of proteinase K in the absence or presence of 1% triton x-100. The treated samples and non-treated controls were separated by SDS-PAGE and analyzed by immuno-blotting using anti-GFP antibody (1:3000; Ab-cam)

Immuno-Fluorescence Microscopy

Four-week-old leaves from wild type, cgr2/3, CGR2OX and CGR3OX were fixed in a fixative [1×PBS pH 7.4, 4%

(v/v) paraformaldehyde, and 0.5% (v/v) glutaraldehyde]. Fixed samples were dehydrated using a series of ethanol (25%, 50%, 75%, and 100%) and embedded in LR white resin (EMS#14381). The traverse sections (0.5 µm) of the central region of leaf were produced using an ultramicrotome, and immuno-labeling of the traverse sections using antibodies were performed as described (Held et al., 2011). Confocal laser scanning microscope (LSM510 Meta microscope from Zeiss) was used to record fluorescent signal using a 488 nm argon laser for excitation and a 505 nm long-pass emission filter. Primary antibodies used for immuno-fluorescence were JIM5 (1:30) and JIM7 (1:30) from CarboSource Services (Athens, Ga.), and LM19 (1:30) and LM20 (1:30) from PlantProbes (Leeds, UK). The goat anti-rat FITC-conjugated antibody (1:100; Sigma) was used as a secondary antibody. Some samples were treated with only secondary antibody to check the background fluorescence and optimization of the settings.

In-Vitro Pollen Germination

Plants were grown in soil for 5~6 weeks under 16 h light/8 h dark cycles. Just opened flowers were collected and gently dabbed onto solid pollen germination medium (5 mM MES pH 6.1 adjusted with 1 M Tris pH 8.0, 1 mM KCl, 10 mM $CaCl_2$, 0.8 mM $MgSO_4$, 1.5 mM Boric acid, 16.6% (w/v) sucrose, 3.65% (w/v) sorbitol, 10 µg/ml Myo-inositol and 1% (w/v) agar) solidified on glass slides. The slides were placed in a humid container and incubated for 24 hr at 25° C. Images of germinated pollen were recorded using a Zeiss Axio Imager M2 microscope. The length of pollen tubes (n=40) was measured with Image-J software.

Propidium Iodide Staining

Six-day-old etiolated hypocotyls grown 0.5×MS medium were stained in the water containing 10 µg mL$^{-1}$ propidium iodide (Sigma) for 30 min. The stained hypocotyls were washed with water and mounted onto the slide. The stained samples were excited at 594 nm and the emitted fluorescence was detected at 604~690 nm using a confocal microscope. The cell length was measured with Image-J software.

Cell Wall Analyses 5 week old aerial tissue of wild type, cgr2-1, cgr3-1, cgr2-1 cgr3-1, CGR2OX, CGR3OX, complemented lines of cgr2-1 cgr3-1 were harvested in liquid nitrogen, and lyophilized immediately. Generation of the alcohol insoluble residues (AIR), neutral sugar composition assay, uronic acid assays and methyl ester assays were performed as described (Foster et al.; Wood and Siddiqui, 1971; Filisetti-Cozzi and Carpita, 1991) with slight modification. Lyophilized leaf was ground using ball-mill and washed three times with 70% ethanol, followed by washing sequentially using chloroform/methanol (1:1), 100% acetone and water. And then, the AIR was lyophilized again. The dried AIR was de-starched using amylase (Sigma) for 2 hr at 37° C. The de-starched AIR was washed in 70% ethanol and dried by vacuum centrifugation. The de-starched AIR was used for cell wall analysis. For neutral sugar composition assay, 1 mg of AIR was analyzed by the GLBRC Cell Wall Analytical Platform (East Lansing, Mich.) as alditol acetate derivatives (York et al., 1985). Uronic acids were quantified using the sulfamate-carbazole method with 0.4 mg AIR for each sample (Filisetti-Cozzi and Carpita, 1991). Methyl ester assays were performed with 4 mg of AIR for each sample as described previously (Wood and Siddiqui, 1971).

Microsome Isolation

Microsome isolation was performed as described by Liepman et al. (2005) with some modification. Stems of six-week-old plants in soil under 16 h light/8 h dark cycles were homogenized in HM buffer (50 mM HEPES pH 7.5, 10 mM $MgCl_2$) with 13.7% (w/v) sucrose. The homogenates were centrifuged at 3,000×g for 5 min at 4° C. The supernatant was centrifuged at 17,000×g for 20 min at 4° C. The resulting supernatant was further centrifuged at 100,000×g for 60 min at 4° C. to pellet microsomes. The microsomes were resuspended in assay buffer (0.25 M sucrose, 50 mM HEPES, pH 7.5, 1 mM $MgCl_2$) for methyltransferase activity assay.

Protein Expression and Purification

CGR2, CGR3, QUA2 coding sequences without transmembrane domains (CGR2ΔTM, CGR3ΔTM, QUA2ΔTM and QUA3ΔTM), include:

for an *Arabidopsis thaliana* CGR2, the encoded amino acid sequence from about 54P to the stop codon is, for example, SEQ ID NO:26:

```
 53          PGIFKSIK EVSKVTGDYSC TAEVQRAIPV
 81 LKKAYGDGMR KVLHVGPDTC SVVSSLLKEEE TEAWGVEPYD
121 IEDADSHCKS FVSKGLVRVA DIKFPLPYRA KSFSLVIVSD
161 ALDYLSPKYL NKTVPELARV ASDGVVLFAG LPGQQRAKVA
201 ELSKFGRPAK MRSASWWNRF FVQTNLEEND APSKKFEQAV
241 SKGLYKPACQ VFHLKPLH
``` for an *Arabidopsis thaliana* CGR3, the encoded amino acid sequence from 54M to the stop codon is, for example, SEQ ID NO:27:

```
 53          MFKSIREV SKITGDYSCT AEVQRAIPIL
 81 KSAYGDSMRK VLHVGPETCS VVSSLLNEEE TEAWGVEPYD
121 VEDADSNCKS LLHKGLVRVA DIKFPLPYRS KSFSLVIVSD
161 ALDYLSPRYL NKTVPELARV ASDGVVLLAG NPGQQKAKGG
201 ELSKFGRPAK MRSSSWWIRF FSQTNLEENE AASKKFEQAA
241 SKSSYKPACQ VFHLKPLH
``` for an *Arabidopsis thaliana* QUA2, the encoded amino acid sequence from 1051 to the stop codon is, for example, (SEQ ID NO:28:

```
105                      ISISTS SRGHVYHNYR
121 RLQEQLVSDL WDIGEISLGP NRWKELEYCN IESENFVPCF
161 NVSENLALGY SNGDENDRFC GPGSKQECLE LPPVKYRVPL
201 RWPTGKDIIW HSNVKITAQE VVSSGSITKR MMMMEDDQIS
241 FRSASPMSDE VEDYSHQIAE MIGIKKDNFI EAGVRTILDI
281 GCGYGSFGAH LLSKQILTMC IANYEASGSQ VQLTLERGLP
321 AMIGSFISKQ LPYPSLSFDM LHCLRCGIDW DQKDGLLLVE
361 IDRVLKPGGY FVWTSPLTNP RNKDHLKRWN FVHDFAESIC
401 WTLLNQQDET VVWKKTINTK CYSSRKPGVG PSVCTKGHDV
441 ESPYYRPLQM CIGGTRSRRW IPIEGRTRWP SRSNMNKTEL
481 SLYGLHPEVL GEDAENWKIT VREYWSLLSP LIFSDHPKRP
501 GDEDPSPPYN MLRNVLDMNA QFGGLNSALL EARKSVWVMN
551 VVPTAGPNHL PMILDRGFVG VLHNWCEPFP TYPRTYDLVH
```

```
601  ADNLLSLQTS QPRKTCLLID IFTEIDRLLR PEGWVIIRDT
641  AQLVEKARET ITQLKWEARV IEVESSSEQR LLICQKPFTK
681  RQSI
```

The coding sequences for these polypeptides, without their transmembrane domains, were amplified from the cDNA of WT seedlings using the following primers.

```
CGR2ΔTM FP (SEQ ID NO: 29):
5'-GAGAACCTGTACTTCCAGGGTATGGCGAGAC
GGCAAGTAGG TTCAA-3'

CGR2ΔTM RP (SEQ ID NO: 30):
5'-CATGACCCCTGCAGGCTAATGTAATGGCTTGAGGTGGA-3'

CGR3ΔTM FP (SEQ ID NO: 31):
5'-GAGAACCTGTACTTCCAGGGTATGTTCAAAAGTATC
AGAGAAGTCAGCAAG-3'

CGR3ΔTM RP (SEQ ID NO: 32):
5'-CATGACCCCTGCAGGCTAATGTAATGGCTTGAGGTGGA-3'

QUA2ΔTM FP (SEQ ID NO: 33):
5'-GAGAACCTGTACTTCCAGGGTATGATTTCCATTTC
GACTTCTTCCAGAGG-3'

QUA2ΔTM RP (SEQ ID NO: 34):
5'-CATGACCCCTGCAGGTCAGATTGATTGTCGCTTGGTGAAT-
3'.
```

The amplified products were digested by SbfI restriction enzyme and cloned into the pMALC5X vector (Biolabs), which was previously digested by XmnI and SbfI. Such insertion generated a fusion protein between the encoded polypeptides of the amplified nucleic acids and maltose-binding protein (MBP). The resulting MBP fused constructs were transformed into *E. coli* (BL21 DE3) cells. The transformed cells were grown in 200 mL LB medium at 37° C. until $OD_{600}$ reached 0.5, and then final 0.1 mM of IPTG was added to induce protein expression at 25° C. for 3 hrs. The cells were harvest after centrifugation at 4,500×g for 10 min at 4° C. and the pellets were stored in −80° C. The cells were resuspended in 10 ml of 1× binding buffer (50 mM HEPES pH 7.4, 200 mM NaCl, and 0.5 mM β-mercaptoethanol) and lysed using a french press. The lysed cells were centrifuged at 50,000×g for 30 min at 4° C., and the resulting supernatants were separated on a MBP column to purify the fusion protein. The fusion proteins were eluted in 10 mM Maltose in 1× binding buffer, and the buffer of purified proteins was exchanged to an assay buffer (50 mM HEPES pH 7.5, 0.5 mM β-mercaptoethanol and 7% glycerol) using a desalting filter (Amicon Ultra-10K; Millipore).

Methyltransferase Activity Assay

The methyltransferase activity assay was performed as described previously (Ibar and Orellana, 2007) with slight modification. Microsomes (50 μg of protein) were incubated in a final volume of 50 μL containing 6 μM [methyl-$^{14}$C] SAM (PerkinElmer) and 24 μM unlabeled SAM in the reaction buffer (50 mM HEPES pH 7.5, 1 mM $MgCl_2$, 1 mM $MnCl_2$, 1 mM $CoCl_2$, 0.25M sucrose and 0.05% Triton x-100) at 25° C. for 1 hr.

Purified enzymes were incubated in a final volume of 50 μL containing 6 μM [methyl-$^{14}$C]SAM (PerkinElmer) and 24 μM unlabeled SAM in the reaction buffer (50 mM HEPES pH 7.5, 1 mM $CoCl_2$, 7% glycerol and 0.5 mM β-mercaptoethanol) at 25° C. As the substrate of the methyltransferase activity assay, oligogalacturonic acid was generated as described previously (Suzuki et al., 2002), and 50 μg of oligogalacturonic acids were used for each reaction. The methylated products were precipitated and washed as described by Goubet et al. (1998). The radioactivity of the precipitated methylated products was measured by liquid scintillation counter.

Enzymatic Treatment

Purified CGR3 protein (112.5 μg) was incubated in a final volume of 450 μL containing 6 μM [methyl-$^{14}$C]SAM (PerkinElmer) and 24 μM unlabeled SAM in the reaction buffer (50 mM HEPES pH 7.5, 1 mM $CoCl_2$, 7% glycerol and 0.5 mM β-mercaptoethanol) at 25° C. for 2 hr. The methylated products were precipitated using 45 μL of 10% BSA and 450 μL of 20% TCA. After washing twice using 2% TCA, the pellet was resuspended in 900 μL of 0.1 M Tris-HCl pH 7.5 and then 100 μL of resuspended pellet was incubated with or without 0.3 U PME (EC3.1.1.11, Prozomix). After 5 hr incubation at 25° C., the reaction was stopped using 100 μL of 20% TCA. After centrifugation at 8,000×g for 5 min, radioactivity of pellet and supernatant were measured using liquid scintillation counter.

Identification of a cgr2-1 Mutant

The cgr2-1 (GK518A09) line with T-DNA insertion in the fifth exon was obtained from the GABI-KAT. Genomic DNA of wild type and cgr2-1 mutant grown on half-strength MS medium plus Gamborg's B5 vitamins and 1% (w/v) sucrose containing 0.8% (w/v) agar was isolated from 14-day-old leaves. A homozygous cgr2-1 mutant was identified by genotyping using the primers CGR2-LP, CGR2-RP, and o8049 primers.

```
CGR2-LP
                                  (SEQ ID NO: 35)
5'-TTTCATTGCTTCAAAGATGGC-3'

CGR2-RP
                                  (SEQ ID NO: 36)
5'-GAGGATGCAGATTCTCACTGC-3' o8049
                                  (SEQ ID NO: 37)
5'-ATATTGACCATCATACTCATTGC-3'.
```

RT-PCR Analysis

Total RNA was isolated from 2-week-old wild-type and cgr2-1 cgr3-1 seedlings grown on half-strength MS medium plus Gamborg's B5 vitamins and 1% (w/v) sucrose using Trizol reagent (Invitrogen, Carlsbad, Calif.). After treating with DNase, cDNA was generated using iScript (Biorad, Hercules, Calif.) with oligo(dT) and random hexamer primers. cDNA was amplified for 25 cycles using following primers to check the presence of CGR2 and CGR3 in the cgr2-1 cgr3-1 mutant. Primers used for RT-PCR included the following.

```
CGR2 FP (SEQ ID NO: 38):
5'-AGGACGTCTAGATGGCGAGACGGCAAGTAGGTTCAAC-3'

CGR2 RP (SEQ ID NO: 39):
5'-CATGACCGTCGACTTATGTAATGGCTTGAGGTGGAAGAC-3'

CGR3 FP (SEQ ID NO: 40):
5'-CAGGACGTCTAGATGTCAAGAAGGCAAGTAAGGCG-3'
```

-continued

```
CGR3 RP (SEQ ID NO: 41):
5'-CATGACCGTCGACTTATGTAATGGCTTGAGGTGGAAAAC-3'

Ubi10 FP (SEQ ID NO: 42):
5'-TCAATTCTCTCTACCGTGATCAAGATGCA-3'

Ubi10 RP (SEQ ID NO: 43):
5'-GGTGTCAGAACTCTCCACCTCAAGAGTA-3'
```

RNA Extraction and Quantitative RT-PCR Analysis

Total RNA was extracted from 2-week old wild type, CGR2OX, CGR3OX and cgr2-1 cgr3-1 seedlings using an RNeasy plant mini kit (Qiagen), followed by DNase I (Qiagen) treatment. cDNA from all samples were reverse-transcribed at the same time using superscript III reverse transcriptase (Invitrogen) with 400 ng of total RNA. Real-time quantitative real-time RT-PCR with SYBR Green detection was performed using the Applied Biosystems 7500 fast real-time PCR system. Data were analyzed by the ÄÄCT method, and the transcript level was normalized to that of the ubiquitin 10 gene for each sample. The changes in the expression level of CGR2, CGR3 and QUA2 in CGR2OX, CGR3OX and cgr2-1 cgr3-1 were compared with the expression level of wild type. Primers used for qRT-PCR included the following.

```
CGR2 FP (SEQ ID NO: 44):
5'-CAAACCAGCCTGCCAAGTCT-3'

CGR2 RP (SEQ ID NO: 45):
5'-TGGTGTGGAACCAGTAGGCTTT-3'

CGR3 FP (SEQ ID NO: 46):
5'-CAAAGTCGTTTTCTCTTGTGATCGT-3'

CGR3 RP (SEQ ID NO: 47):
5'-TCAGGCACAGTTTTGTTCAGGTA-3'

QUA2 FP (SEQ ID NO: 48):
5'-TGTCGGAGTTTTGCACAACTG-3'

QUA2 RP (SEQ ID NO: 49):
5'-TGTCTGCATGTACCAGGTCATATG-3'

Ubi10 FP (SEQ ID NO: 50):
5'-CGCTTCGTTTTTATTATCTGTGCTT-3'

Ubi10 RP (SEQ ID NO: 51):
5'-TCGCAGAACTGCACTAAACAGAGT-3'.
```

Methyltransferase Activity Assay with Diverse Cations

Methyltransferase activity assays were performed as described in the main text. Purified enzymes were incubated in a final volume of 50 µL containing 6 µM [methyl-$^{14}$C] SAM (PerkinElmer) and 24 µM unlabeled SAM in the reaction buffer (50 mM HEPES pH 7.5, 7% glycerol and 0.5 mM β-mercaptoethanol) with either 1 mM of $MgCl_2$, $MnCl_2$, $CoCl_2$, $CaCl_2$, $CuCl_2$ or $ZnCl_2$ at 25° C. for 1 hr. The methylated products were precipitated and washed as described in the main text. The radioactivity of the precipitated methylated products was measured by liquid scintillation counter.

Example 2: CGR2 and CGR3 Constitute a Plant-Specific Gene Family and do not Encode a QUA2-Like Methyltransferase Domain The inventors have identified a homolog of CGR3 in the Arabidopsis genome and named the homolog CGR2. CGR2 (encoded by a nucleic acid with NCBI accession no. At3g49720) has 87% amino acid identity with CGR3 (encoded by a nucleic acid with NCBI accession no. At5g65810) (FIG. 1A). Based on in-silico expression profile analyses (Winter et al., 2007), CGR2 and CGR3 are ubiquitously expressed in Arabidopsis, although the overall expression of CGR2 is higher than that of CGR3. The strongest expression levels of CGR3 were found in the stamen and mature pollen, suggesting CGR3 may have a predominant role in pollen.

The inventors have previously discovered that CGR3 is co-expressed with genes involved in the biosynthesis and modification of cell wall polysaccharides by analysis of the ATTED-II database of co-expressed genes (Held et al., 2011). Investigations were undertaken to determine whether genes co-expressed with CGR2 were involved in cell wall synthesis or modification also using the ATTED-II database. CGR2 was identified to be highly co-expressed with two putative methyltransferases in QUA2 family (Mouille et al., 2007), GAUT9 (galacturonosyltransferase 9) putatively involved in homogalacturonan synthesis (Sterling et al., 2006) and AtPME1 (pectin methylesterase 1) in de-esterifying pectin (Richard et al., 1996; Sterling et al., 2006; Mouille et al., 2007) (Table 1), indicating that CGR2 can be involved in pectin biosynthesis or modification.

Table 1 shows genes co-expressed with CGR2 (At4g49720) listed according to the MR value (mutual ranking). Pearson correlation values (COR) and predicted function of the genes are also included in the table.

TABLE 1

| Genes Co-Expressed with CGR2 | | | |
|---|---|---|---|
| MR | COR | Locus | Annotation |
| 1 | 0.81 | At1g04430 | Putative methyltransferase (DUF 248) |
| 1.4 | 0.8 | At4g27720 | Unknown protein |
| 1.7 | 0.79 | At4g18030 | Putative methyltransferase (DUF 248) |
| 2 | 0.74 | At4g30996 | NKS1 (Na- and K-sensitive 1) |
| 2.5 | 0.73 | At3g17390 | MTO3 (METHIONINE OVER-ACCUMULATOR 3) |
| 4.1 | 0.68 | At3g02350 | GAUT9 (Galacturonosyltransferase 9) |
| 5.4 | 0.65 | At5g05820 | Phosphate translocator-related |
| 6.7 | 0.73 | At3g52940 | FK (FACKEL) |
| 7.3 | 0.62 | At4g09640 | Putative metabolite transporter |
| 10.1 | 0.64 | At1g53840 | ATPME1 |
| 10.2 | 0.64 | At1g67950 | RNA recognition motif (RRM)-containing protein |
| 13.9 | 0.55 | At1g76340 | Integral membrane family protein |

Domain analyses of CGR2 and CGR3 by amino acid sequence comparison identified possible methyltransferase domains in CGR2 and CGR3, but those domains did not have extensive homology to QUA2 (DUF 248) (FIGS. 1A and 1B). Rather, CGR2 and CGR3 were found to contain a SAM-dependent methyltransferase (PF08241) domain that partially overlaps with a SAM binding domain of QUA2, but QUA2 had only a few conserved residues relative to CGR2 and CGR3 (FIGS. 1A and 1B). These analyses indicate that if CGR2 and CGR3 are methyltransferases, their function depends on a methyltransferase domain that is different from that of the QUA methyltransferases.

Example 3: CGR2 and CGR3 are Golgi-Localized Type-II Membrane Proteins

Figure 1C:
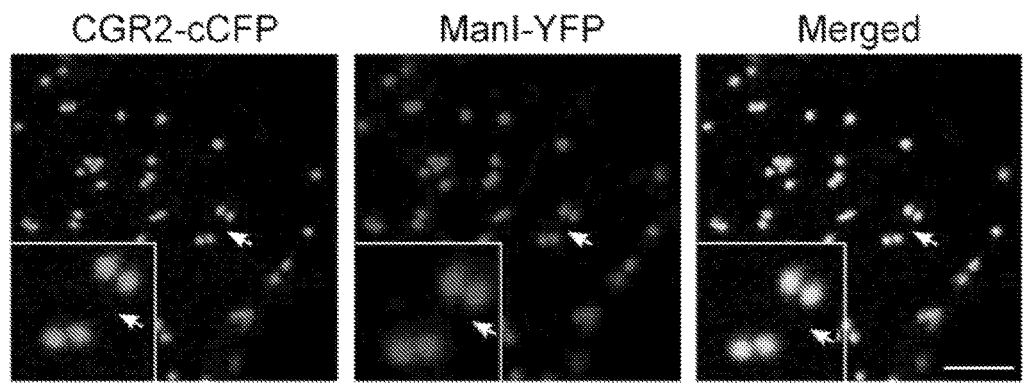
Figure 1D:
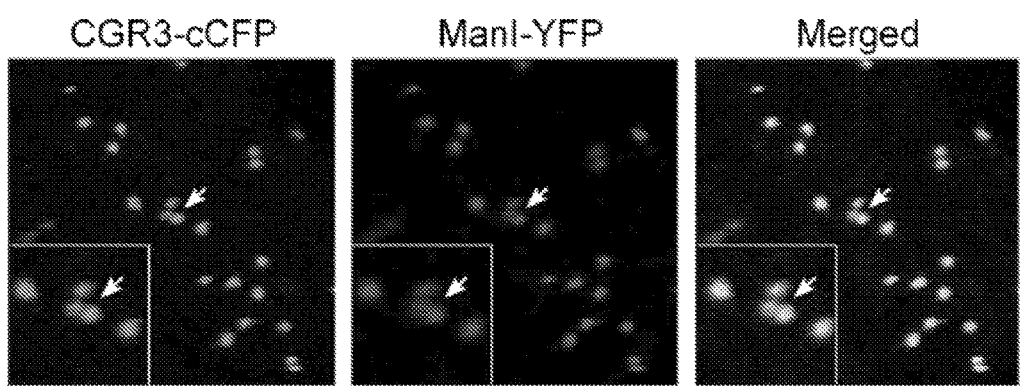

Pectin biosynthesis and methyl-esterification are believed to occur in the cis-Golgi, and medial- and trans-Golgi, respectively (Zhang and Staehelin, 1992). In view of a putative methyltransferase domain in CGR2 tests were designed to ascertain whether CGR2 is localized to the Golgi. A cerulean fluorescent protein (cCFP) fused to the C-terminus of CGR2 (CGR2-cCFP) was made and expressed with a Golgi marker (ManI-YFP) in tobacco leaves. Confocal analyses of CGR2-cCFP with ManI-YFP showed extensive colocalization of the fluorescent signals (FIG. 1C), demonstrating Golgi localization of CGR2 similar to CGR3-cCFP (FIG. 1D) (Held et al., 2011).

Figure 1E:
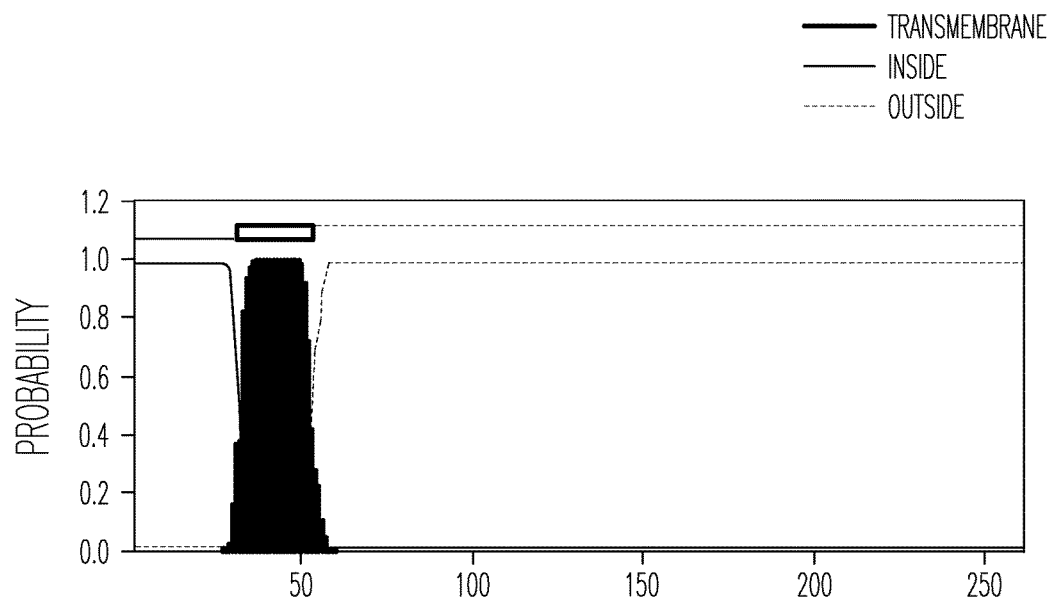
Figure 1F:
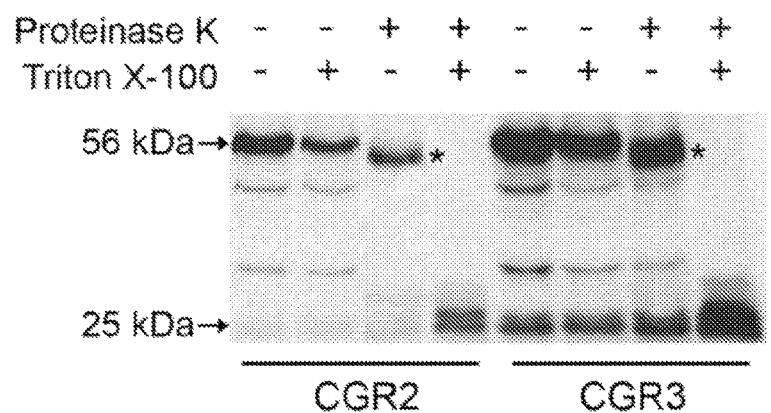
Figure 1G:
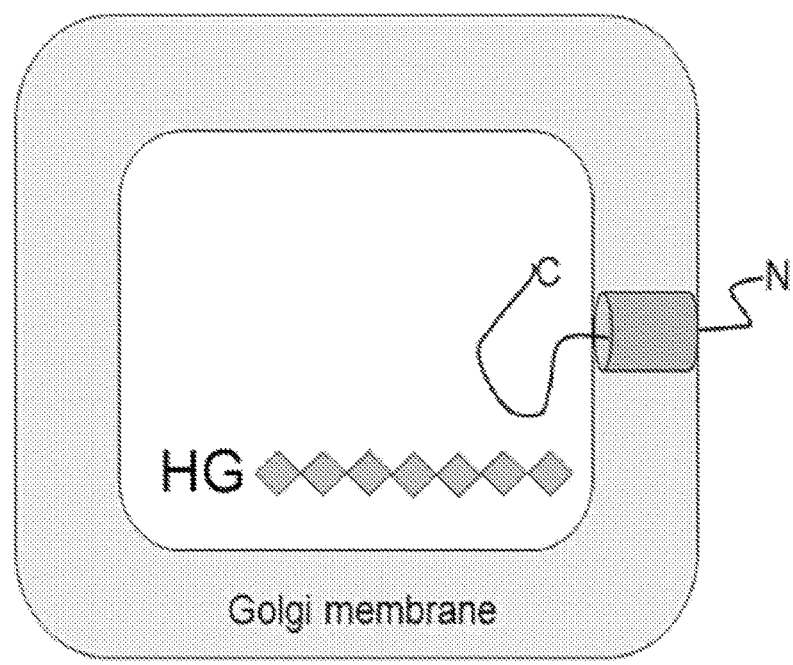

The topology of CGR2 and CGR3 was then investigated. Because methyl-esterification of homogalacturonan has been reported to occur inside the Golgi (Ibar and Orellana, 2007), the majority of the CGR2 and CGR3 proteins would be expected to be inside the Golgi lumen. Topology analyses (see website at cbs.dtu.dk/services/TMHMM-2.0/) predict that CGR2 has one transmembrane domain with short cytosolic N-terminal domain (FIG. 1E). To establish the topology of CGR2 with respect to Golgi membranes, limited proteolysis experiments were performed. Microsomal fractions of *Arabidopsis* plants expressing either CGR2 or CGR3 fused to cCFP at the C-terminus were treated with proteinase K in the absence or presence of membrane detergent (Triton X-100), followed by immuno-blotting with anti-GFP serum, which recognizes also cCFP. Full-length CGR2-cCFP (56 kDa) was detected in the control and in the samples treated with Triton X-100 only (FIG. 1F). In the presence of proteinase K, a truncated version of the fusion protein of the apparent MW 52 kDa was identified (FIG. 1F, asterisk), suggesting that the N-terminus of the protein is exposed to the cytosol and that the C-terminus of CGR2 is contained within the Golgi. For confirmation, samples treated with both proteinase K and Triton X-100 lead to disappearance of the full-length CGR2-cCFP (FIG. 1F). These results indicate that CGR2 is a type-II Golgi membrane protein (FIG. 1G).

Example 4: CGR2 and CGR3 have Overlapping Functions in Plant Growth

Impairment of homogalacturonan synthesis or homogalacturonan modification can cause severe plant phenotypes including dwarfism, defects in hypocotyl elongation, and cell-cell adhesion (Bouton et al., 2002; Bosch et al., 2005b; Francis et al., 2006; Krupkova et al., 2007; Mouille et al., 2007). While the inventors have hypothesized that CGR3 may be a putative methyltransferase, a cgr3-1 knockout mutant did not exhibit changes in plant phenotype (Held et al., 2011). Because of the amino acid sequence identity shared between CGR2 and CGR3 (FIG. 1A) and their co-localization at the Golgi (FIGS. 1C and 1D), the inventors hypothesized that the two proteins share overlapping functions, and one may compensate for the loss of the other.

Figure 2A:
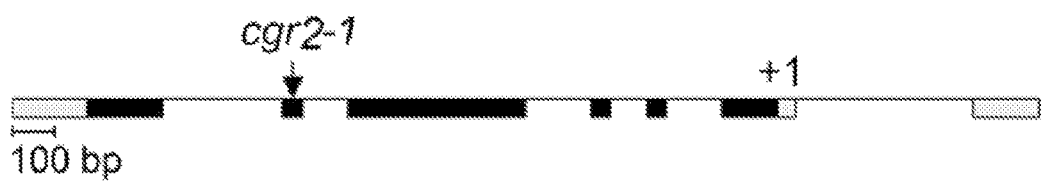
FIGS. 2A-2P show that CGR2 and CGR3 share overlapping functions in plant growth.
Figure 2B:
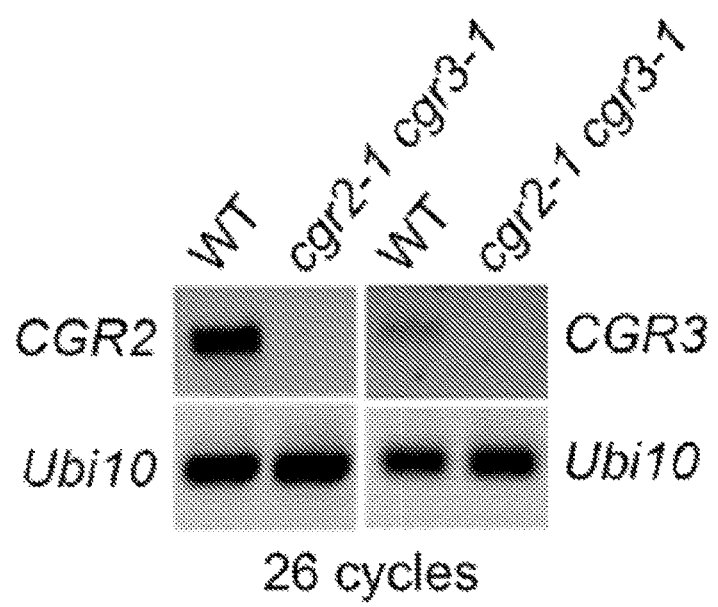
FIG. 2B illustrates that CGR2 and CGR3 transcripts are absent in the cgr2-1 cgr3-1 mutant as confirmed by RT-PCR. Ubi10 was used for control for equal loading.
Figure 2C:
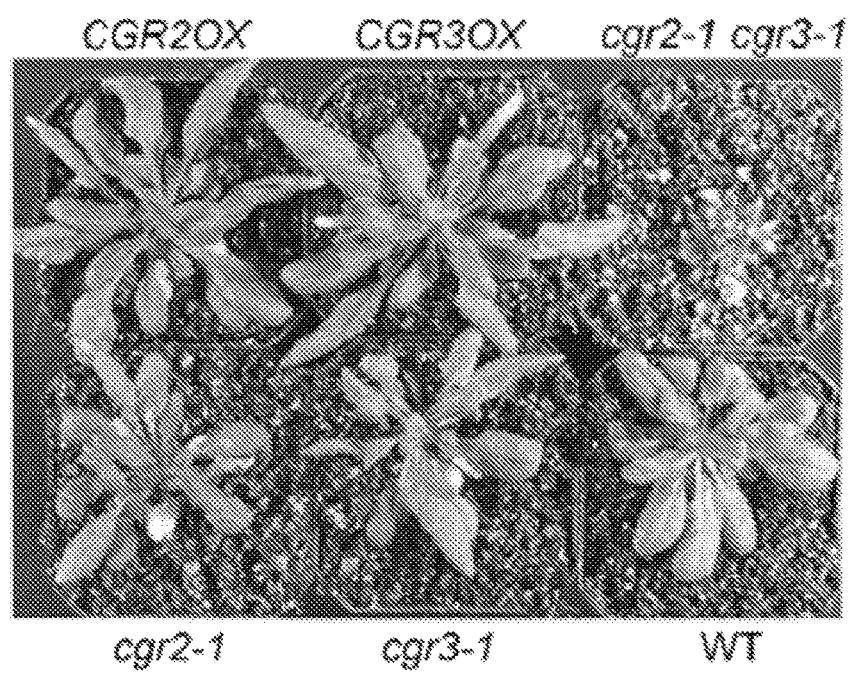
FIG. 2C is an image of 5-week-old plants grown under 12 h (light)/12 h (dark) light conditions. The cgr2-1 cgr3-1 mutant plants exhibited a dwarf phenotype. Two overexpression lines (CGR2OX and CGR3OX) exhibited enhanced growth compared to wild type.
Figure 2D:
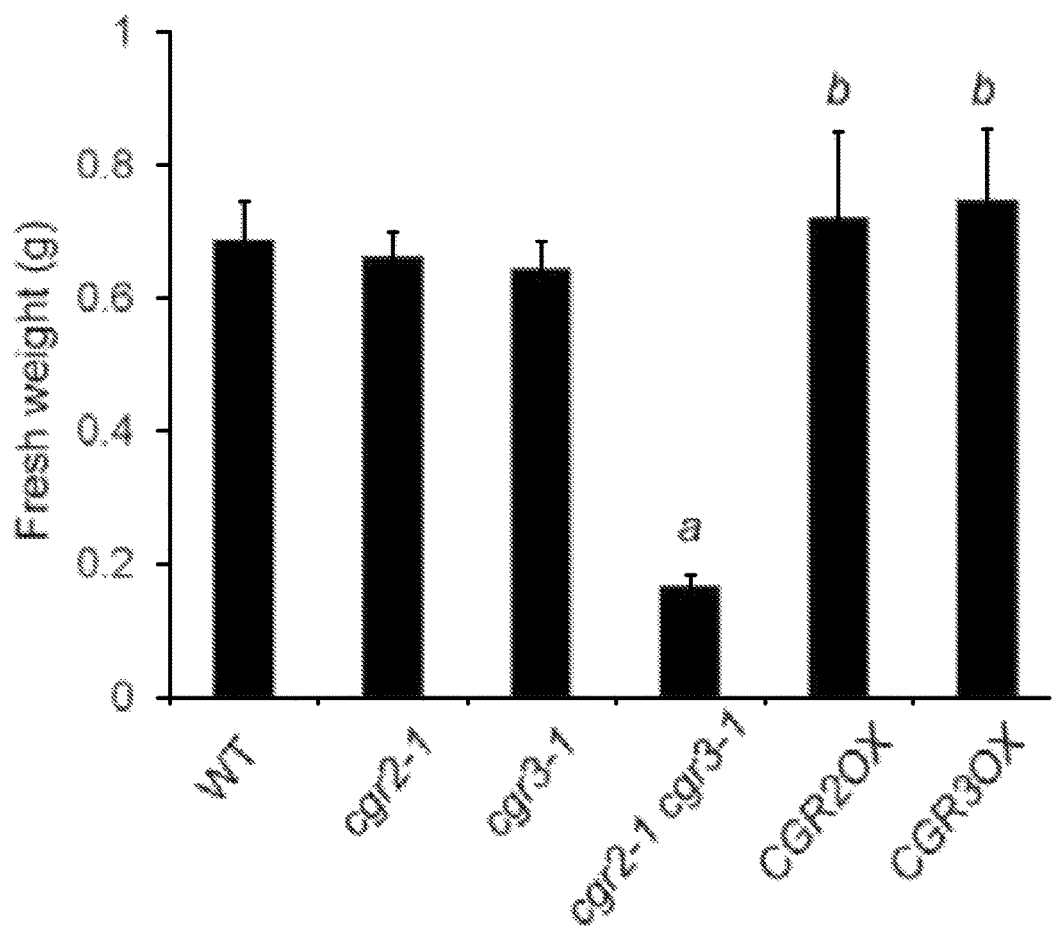
FIG. 2D graphically illustrates the quantity of fresh plant tissue weight from various plant types. Aerial tissues from five week-old wild type, cgr2-1, cgr3-1, cgr2-1 cgr3-1 mutants, CGR2OX and CGR3OX were measured. Error bars represent SD; n=10 for each genotype. a, P<0.0001; b, P<0.05 by Student's t-test.
Figure 2E:
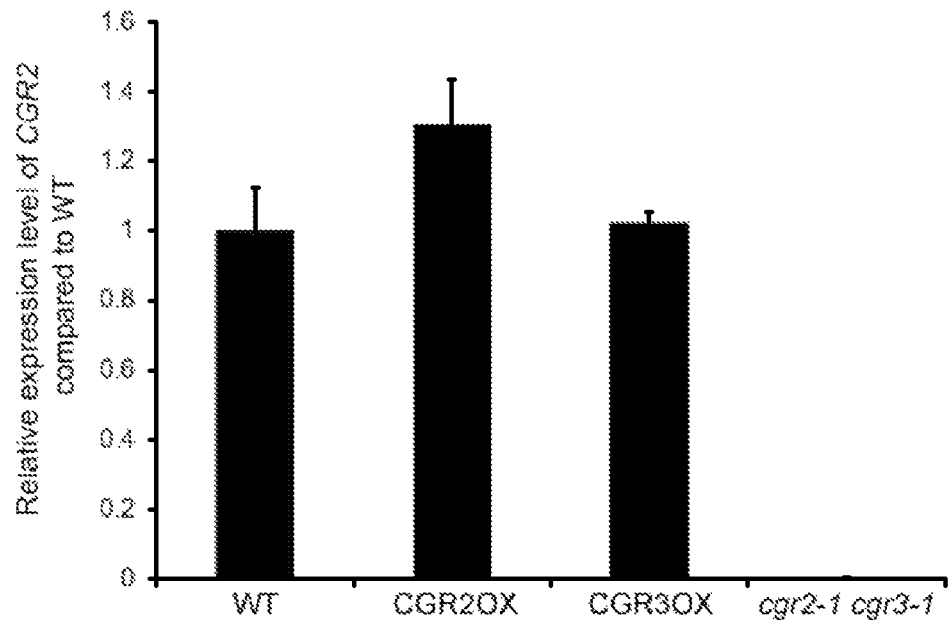
FIG. 2E graphically illustrates the relative expression levels of CGR2 after normalization to the expression level of UBI10 for plant tissues from wild type and transgenic plants. The expression levels of CGR2 in wild type were set to 1.
Figure 2F:
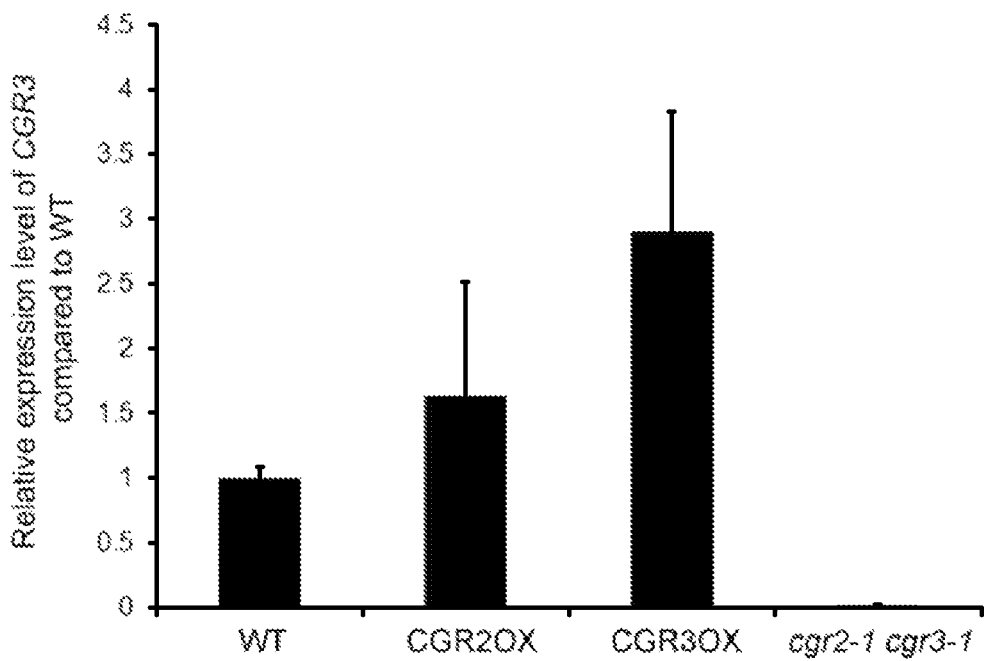
FIG. 2F graphically illustrates the relative expression levels of CGR3 after normalization to the expression level of UBI10 from wild type and transgenic plants. The expression level of CGR3 in wild type was set to 1. Error bars represent the SE (n=3).
Figure 2G:
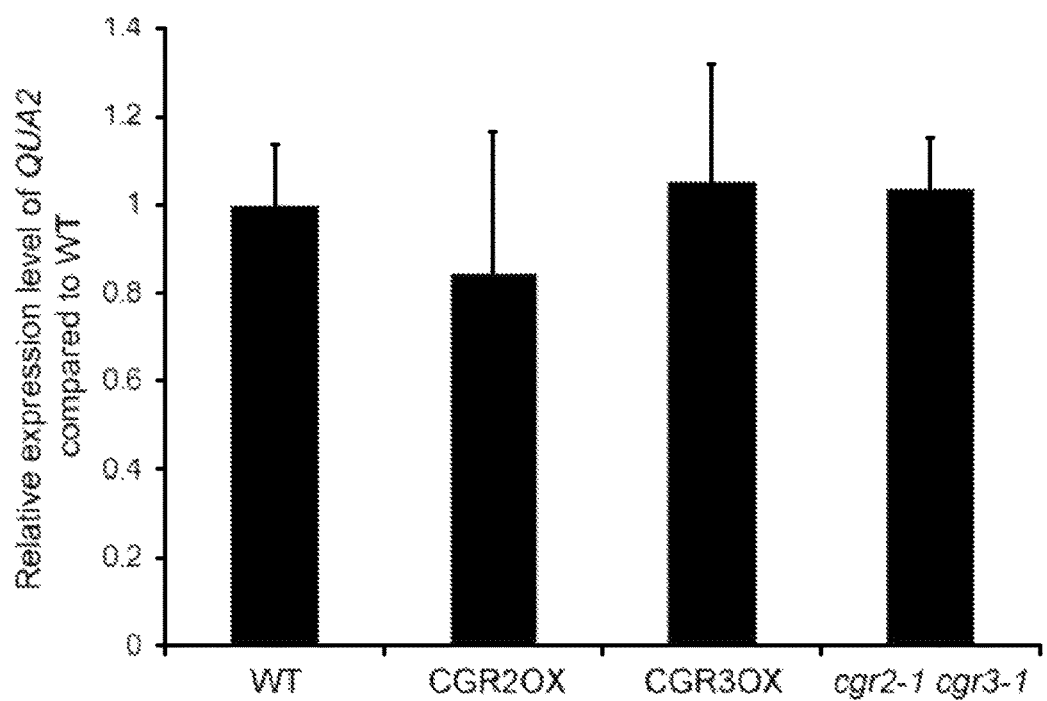
FIG. 2G graphically illustrates the relative expression levels of QUA2 after normalization to the expression level of UBI10. The expression level of QUA2 in wild type was set to 1. Error bars represent the SE (n=3).
Figure 2H:
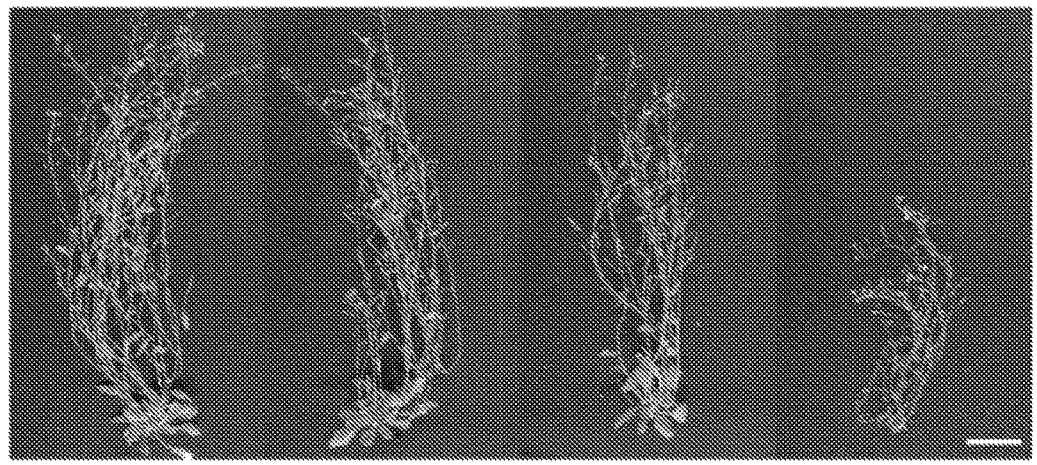
FIGS. 2H and 2I show images of transgenic plants. CGR2-cCFP and CGR3-cCFP were transformed into the cgr2-1 cgr3-1 mutant to test for complementation. CGR2com=CGR2-cCFP into cgr2-1 cgr3-1 cells or plants; CGR3com=CGR3-cCFP in cgr2-1 cgr3-1 cells or plants. Transformation with these constructs recovered the dwarf phenotype of cgr2-1 cgr3-1 mutant. Scale bar=5 cm.
Figure 2I:
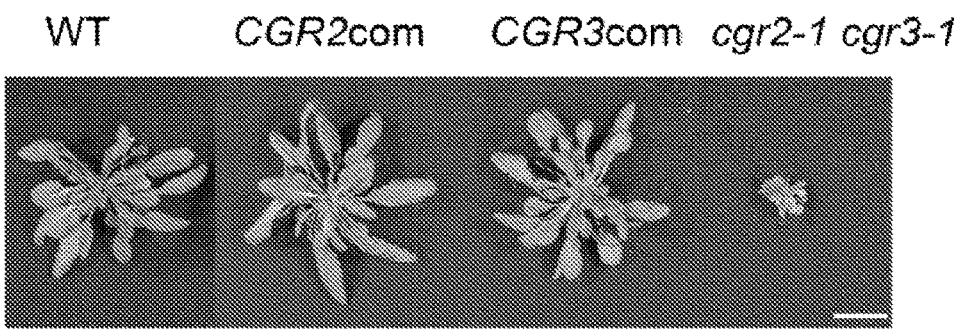

To test this hypothesis and gain insights into the functions of the two proteins, a cgr2-1 cgr3-1 double mutant was generated by isolation of a CGR2 mutant (cgr2-1) bearing a T-DNA insertion in the fifth exon that corresponds to a null allele (FIGS. 2A-2B). Like the CGR3 knockout (cgr3-1) mutant, no obvious phenotype was observed in the cgr2-1 mutant (FIG. 2C). However, the cgr2-1 cgr3-1 double mutation caused a marked reduction on overall rosette growth and fresh weight (FIGS. 2C and 2D). Conversely, overexpression of CGR2 (CGR2OX) lead to an overall increase in rosette size and fresh weight (FIGS. 2C and 2D), indicating that both CGR2 and CGR3 expression can influence plant growth. Compared to wild type, expression of CGR2 and CGR3 was higher in the CGR2OX and CGR3OX transgenic plants, respectively (FIG. 2E-2G). Complementation of the cgr2-1 cgr3-1 mutant with either CGR2-cCFP or CGR3-cCFP completely restored the phenotype (FIGS. 2H and 2I), indicating that the fusions are functional and that the observed phenotypes are linked specifically to the respective loss-of-function mutations.

Figure 2J:
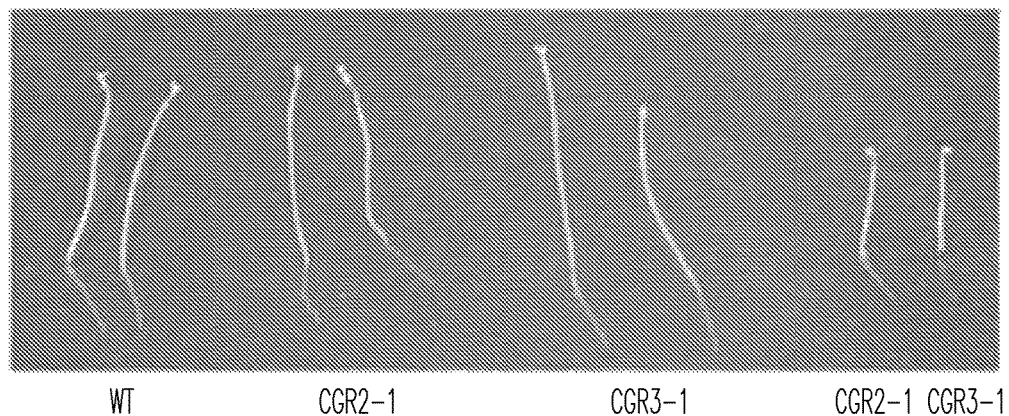
FIG. 2J shows images of 6 day-old etiolated hypocotyls. Shorter hypocotyl and root were observed for cgr2-1 cgr3-1 mutant compared to wild type and single mutants.
Figure 2K:
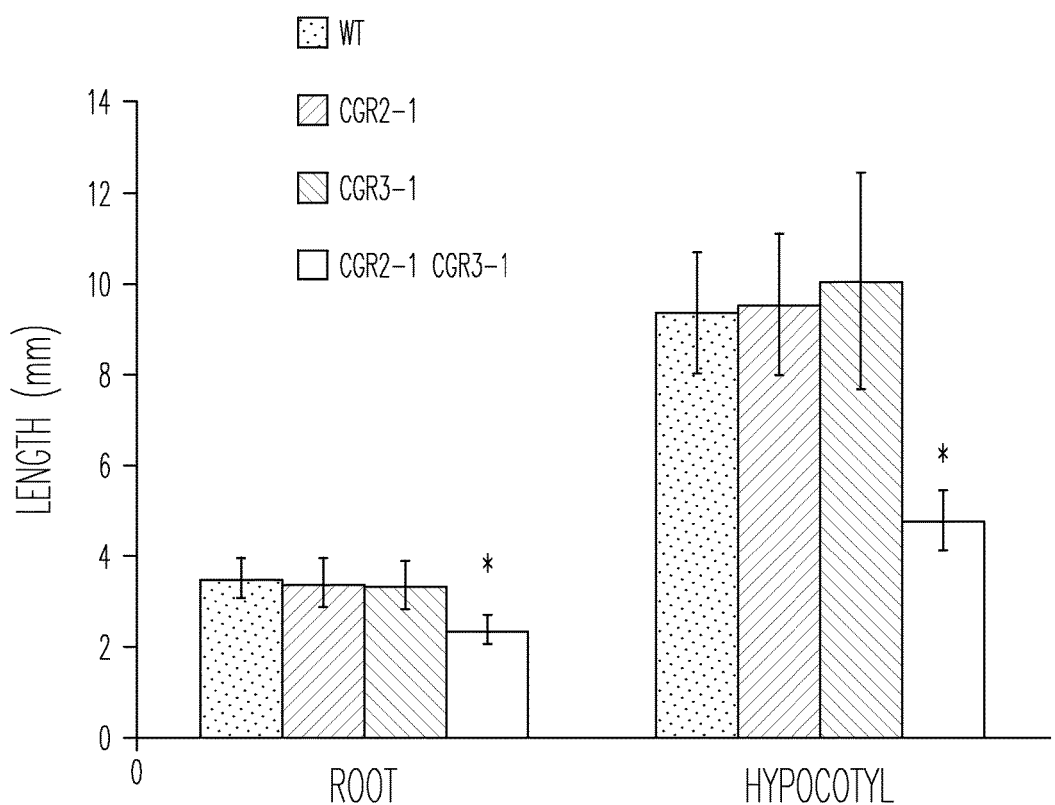
FIG. 2K graphically illustrates the root and hypocotyl length of wild type and mutant plants. Six day-old hypocotyls and roots of etiolated hypocotyls from wild type, cgr2-1, cgr3-1, cgr2-1 cgr3-1 mutants were measured. Error bars represent SD; n=20 for each genotype. The asterisks indicate P<0.0001 by Student's t-test.
Figure 2L:
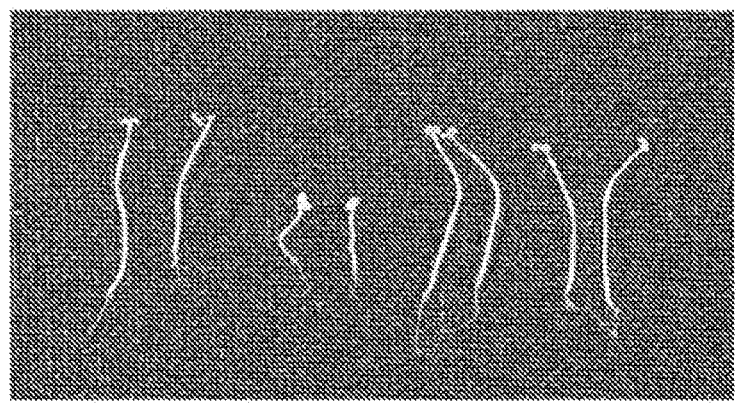
FIG. 2L shows image of 6 day-old hypocotyl of WT, cgr2-1 cgr3-1, CGR2com and CGR3com.
Figure 2M:
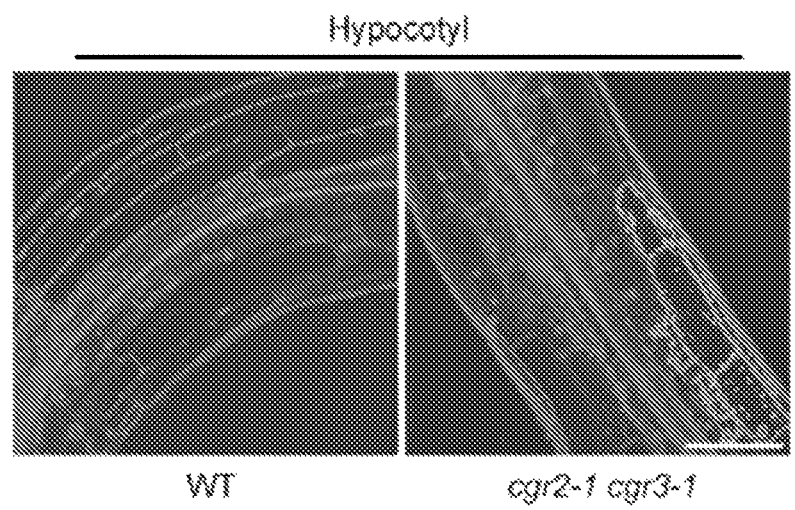
FIG. 2M shows images of the hypocotyls of 5 day-old wild type and cgr2-1 cgr3-1 mutant plants. The cgr2-1 cgr3-1 mutant exhibited reduced elongation.
Figure 2N:
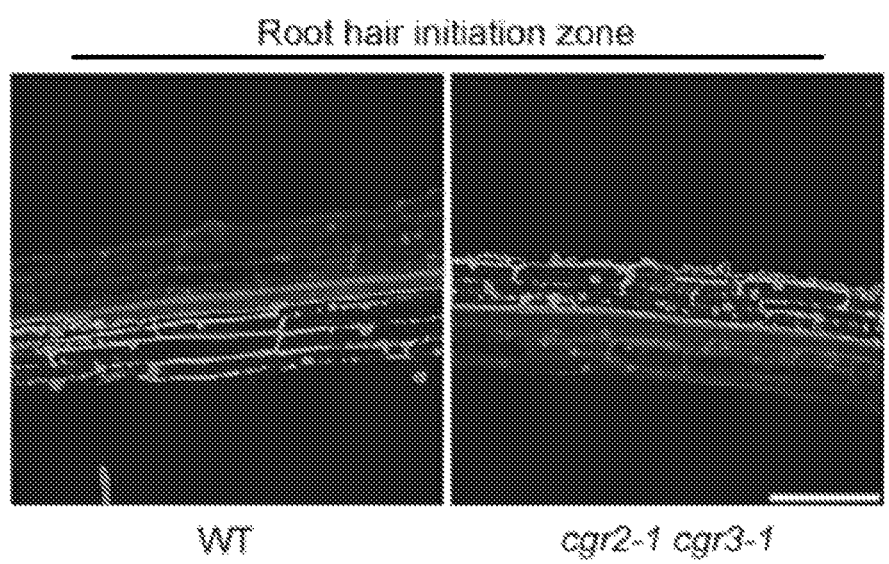
FIG. 2N shows images of root hair initiation zones stained with propidium iodide, exhibiting the reduced elongation of the double mutant compared to wild type. Lighter boundaries of cells were drawn to help identification of single cell. Scale=100 μm.
Figure 2O:
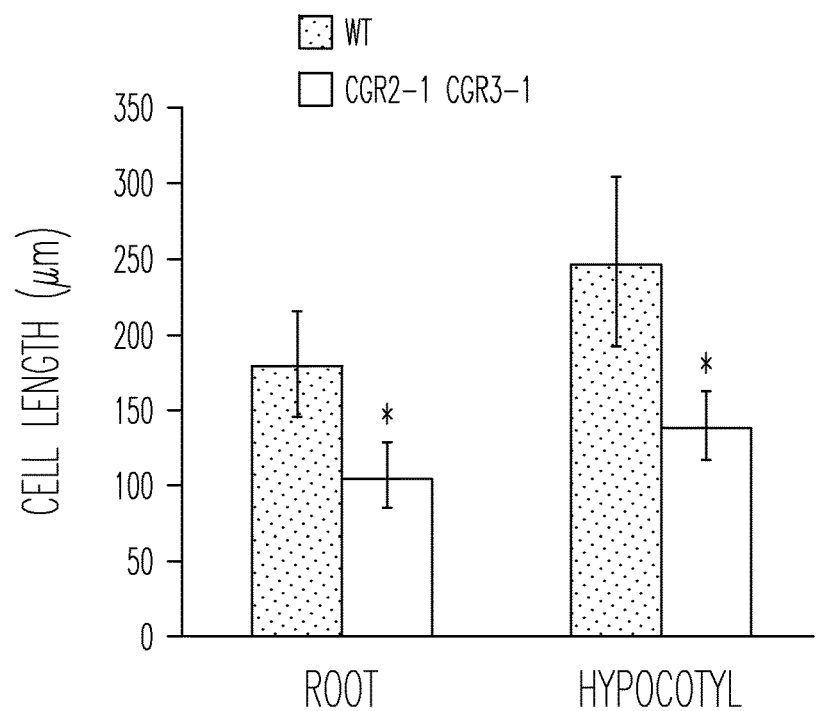
FIG. 2O graphically illustrates cell length in hypocotyls and root hair initiation zones of wild type and cgr2-1 cgr3-1 mutant plants. Six-day-old hypocotyls and roots were measured from etiolated hypocotyls from wild type, cgr2-1, cgr3-1, cgr2-1 cgr3-1 mutants. Error bars represent SD; n=20 for each genotype.

To explore the causes of the plant phenotype at a cellular level, the growth of etiolated hypocotyls was examined, because hypocotyls are the tissue that contains highly methyl-esterified pectin (Derbyshire et al., 2007). As shown in FIGS. 2J-2L, the hypocotyl length of cgr2-1 and cgr3-1 single mutants was similar to wild type. However, the hypocotyl length of the double mutant cgr2-1 cgr3-1 was about half of that observed for wild type. When complemented with the CGR2OX and CGR3OX transgenes, the cgr2-1 cgr3-1 mutant showed similar hypocotyl length to wild type (FIGS. 2J-2L). Because the base of the hypocotyl contains the oldest and most highly elongated cells in the hypocotyl (Gendreau et al., 1997), the bottom part of hypocotyl of wild type and cgr2-1 cgr3-1 mutant were analyzed by confocal microscopy upon propidium iodide staining of the cell walls to investigate whether the short hypocotyl length of cgr2-1 cgr3-1 mutant was caused by reduced cell elongation. Cells at the base of wild-type hypocotyls were highly elongated (FIG. 2M). However, cells at the base of cgr2-1 cgr3-1 mutant hypocotyl showed shorter length (FIGS. 2M and 2O). Additionally, the primary root length and the cell length at the root hair initiation zone of cgr2-1 cgr3-1 mutant were also much shorter than wild type (FIGS. 2N and 2O). Together, these data indicate that CGR2 and CGR3 share important but overlapping roles in cell elongation.

Example 5: Loss of CGR2 and CGR3 Reduces Methyl-Esterification of Homogalacturonan This Example illustrates that loss of CGR2 and CGR3 reduces methyl-esterification of homogalacturonan.

Analysis by immunofluorescence microscopy was used to ascertain whether the cgr2-1 cgr3-1 phenotype is correlated with the degree of homogalacturonan methyl-esterification. Traverse sections of leaves were stained with JIM5 and LM19 antibodies that recognize homogalacturonan with a low degree of methyl-esterification. Other sections of leaves were stained with JIM7 and LM20 antibodies which recognize homogalacturonan with a higher degree of methyl-esterification (Clausen et al., 2003; Verhertbruggen et al., 2009).

Figure 3:
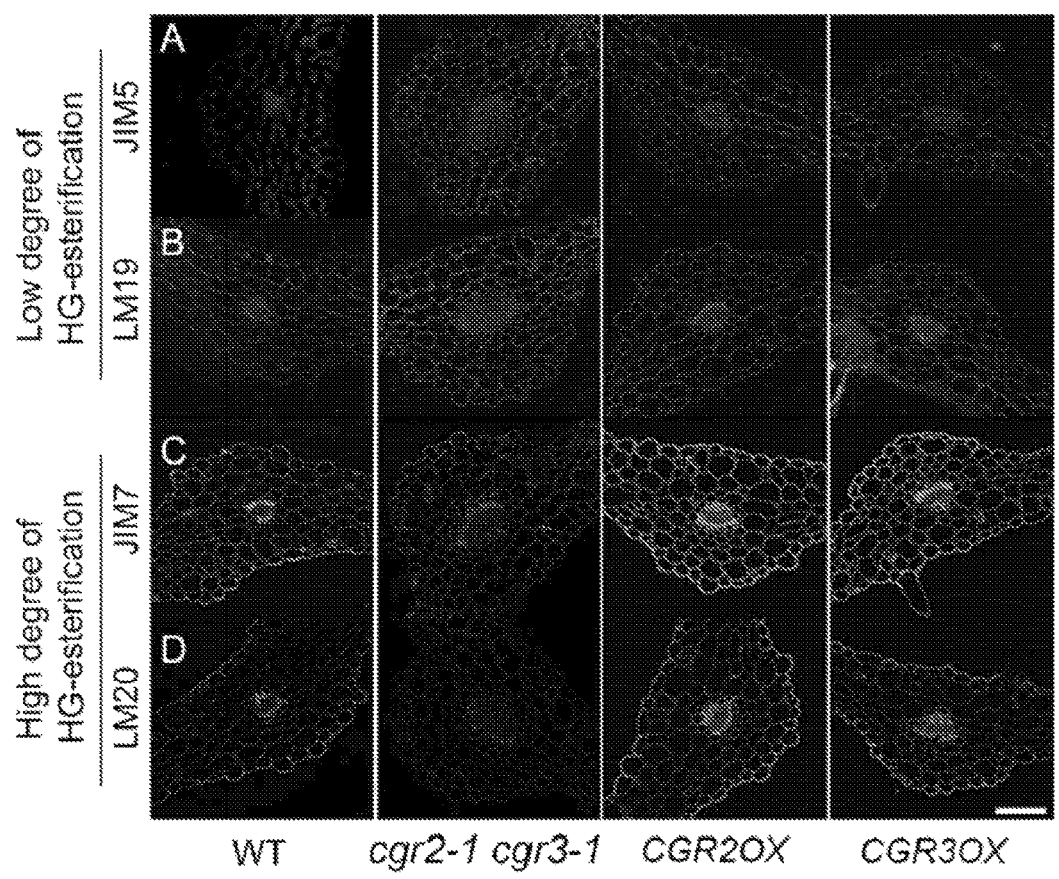
FIG. 3 illustrates that the presence of CGR2 and CGR3 determines accumulation of a high degree of homogalacturonan esterification. Immunofluorescence analyses of traverse section of leaves were performed using antibodies reactive against low (JIM5 (A); and LM19 (B)) and high (JIM7 (C); and LM20 (D)) degree of methyl-esterified homogalacturonan. Scale bar=50 μm.

FIGS. 3A and 3B shows that the levels of low degree methyl-esterified homogalacturonan epitopes recognized by JIM5 and LM19 antibodies seemed largely unaffected regardless of the expression of CGR2 and CGR3 in leaves. This may be a result of the fairly low abundance of these epitopes in the leaf tissues. However, FIGS. 3C and 3D show that compared to wild type, the signal from JIM7 and LM20 antibodies that recognize a higher degree of methyl-esterified homogalacturonan was lower in the cgr2-1 cgr3-1 mutant. Conversely, methyl-esterified homogalacturonan was much higher in CGR2OX and CGR3OX leaves that overexpress CGR2 and CGR3 (FIG. 3, lower images, C and D). These data indicate that the degree of methyl-esterified homogalacturonan in the cell wall depends on the availability of CGR2 and CGR3, and that loss of CGR2 and CGR3 can result in decreased methyl-esterification of homogalacturonan. In addition, as shown herein loss of CGR2 and CGR3 reduces the synthesis of homogalacturonan.

To confirm these findings, the effects of the loss of CGR2 and CGR3 were tested in a different tissue. Pectin is the main cell wall component at the tip of pollen tubes (Bosch and Hepler, 2005) and pectin with a high degree of methylesterification at the tip of the pollen tubes is essential for pollen tube elongation (Tian et al., 2006; Rockel et al., 2008; Zhang et al., 2010).

Figure 2P:
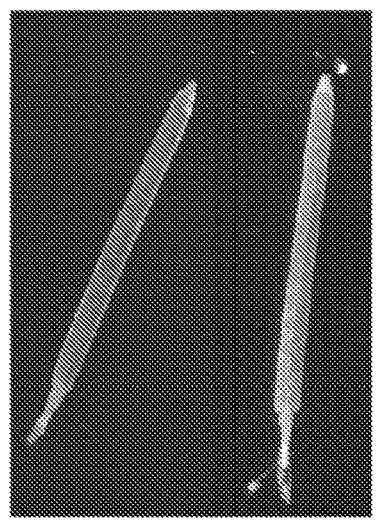
Figure 4A:
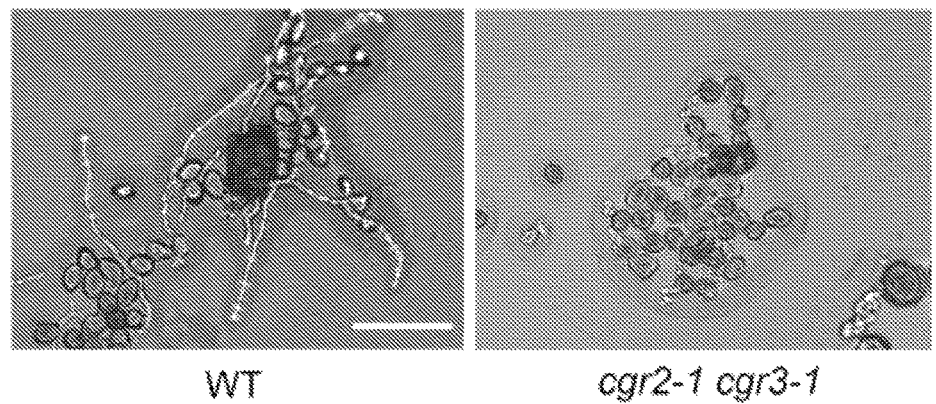
FIGS. 4A-4D illustrate that the cgr2-1 cgr3-1 mutant exhibits defects in pollen germination as well as pollen tube elongation.
Figure 4B:
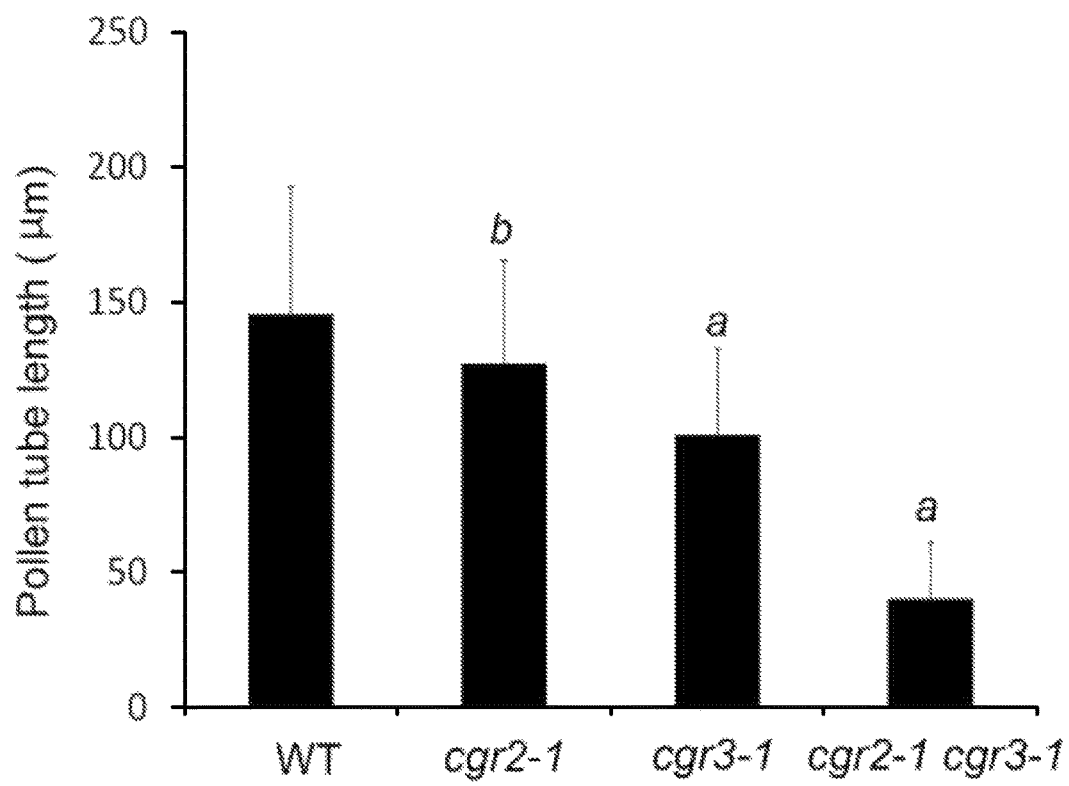
Figure 4C:
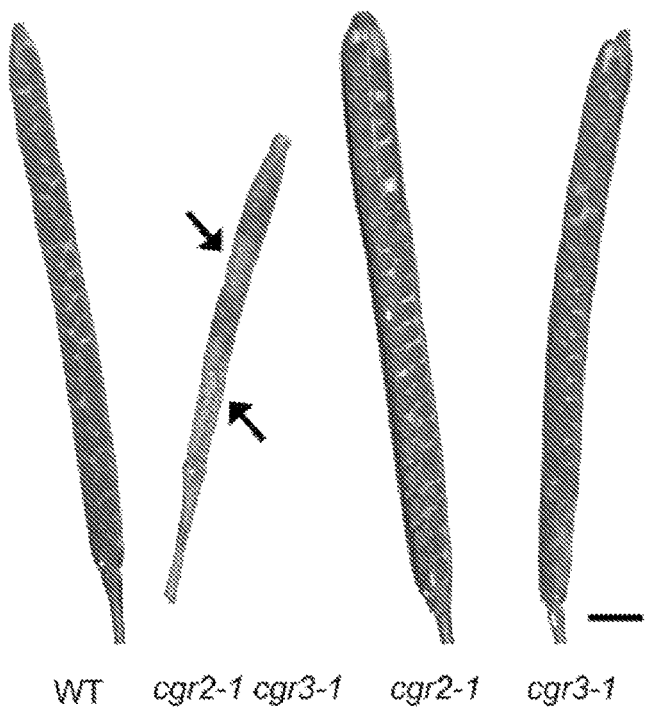
Figure 4D:
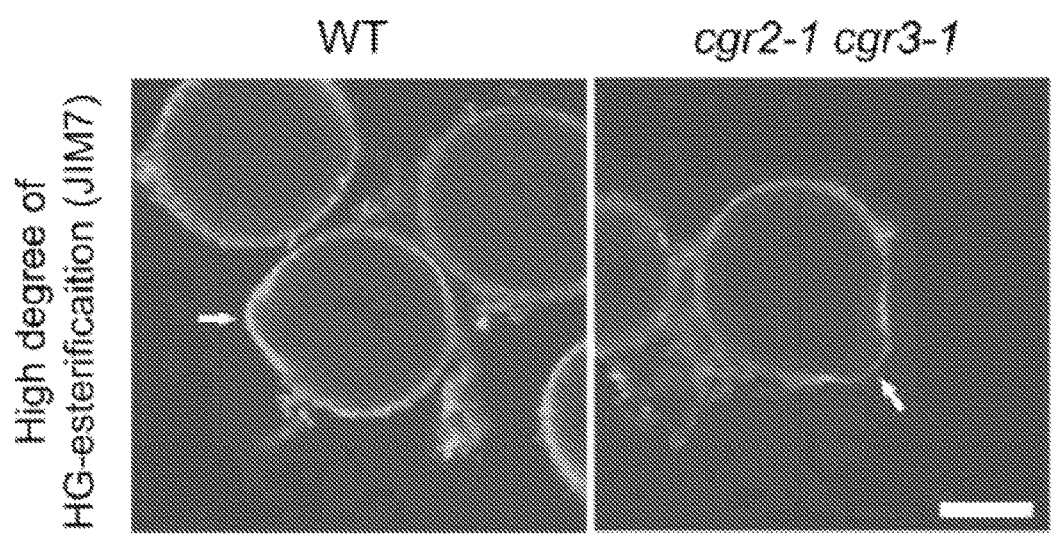

In-vitro pollen germination assays followed by immunofluorescence analyses were performed with the cgr2-1 cgr3-1 mutant to ascertain whether these mutations have defects in pollen tube elongation. Pollen tubes were stained with the JIM7 antibody. As shown in FIG. 4A, the morphology of the cgr2-1 cgr3-1 pollen tube was significantly different from wild type pollen tubes. The pollen tubes of cgr2-1 cgr3-1 showed curved and twisted shapes, and the lengths of the pollen tubes were also strikingly shorter than those of wild type (FIGS. 4A and 4B). Wild type pollen tubes were strongly labeled by the JIM7 antibody, which is reactive with highly methyl-esterified homogalacturonan. However, only weak labeling of highly methyl-esterified homogalacturonan was observed with the JIM7 antibody in the pollen tube tips of cgr2-1 cgr3-1 mutants (FIG. 4D). In addition, shorter silique length and fewer seeds per silique were observed in the cgr2-1 cgr3-1 mutant as compared to wild type (FIG. 4C), probably due to the defects in pollen tube elongation in the cgr2-1 cgr3-1 mutant (FIG. 4A). Such defects were not observed in the siliques of complemented lines (FIG. 2P). These results support a role for CGR2 and CGR3 in homogalacturonan methyl-esterification.

Example 6: Loss of CGR2 and CGR3 Alters Cell Wall Composition that is Specific to Pectin The composition of neutral and acidic monosaccharides and the crystalline cellulose content in the cell wall were of cgr2-1 cgr3-1 mutant plants was investigated. In particular, de-starched alcohol-insoluble residues (AIR) from the leaf tissue of wild type, cgr2-1, cgr3-1 and cgr2-1 cgr3-1 mutants, CGR2OX and CGR3OX plants, and complemented lines of cgr2-1 cgr3-1 were investigated using neutral sugar composition and uronic acid assays to confirm the results from the immunofluorescence assays described above.

Figure 5A:
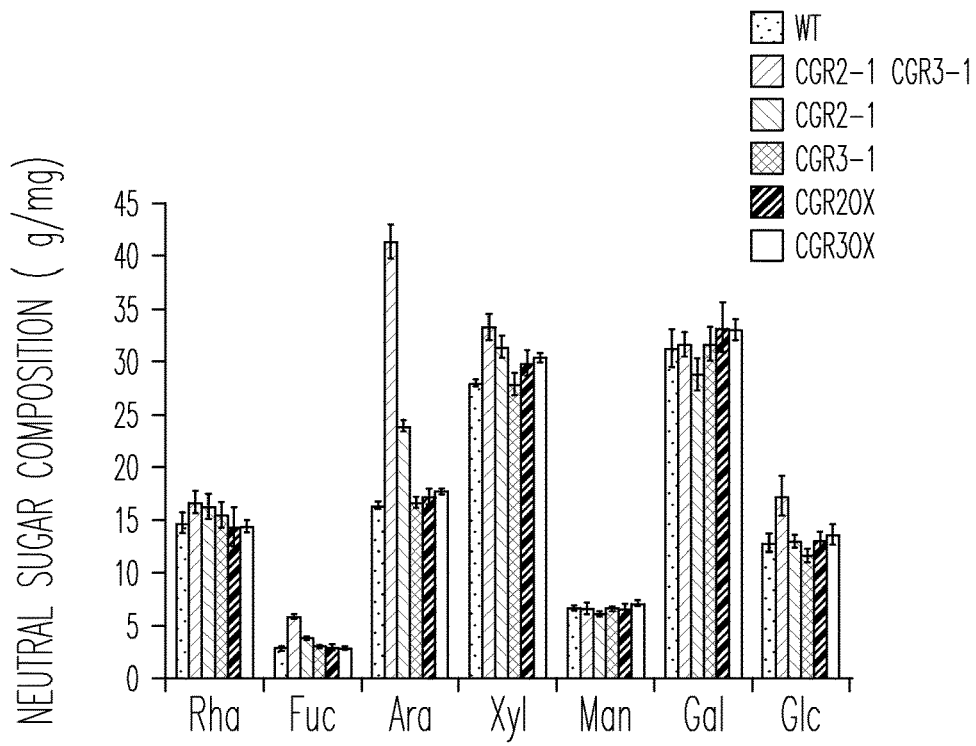
FIGS. 5A-5D illustrate that the leaves of cgr2-1 cgr3-1 mutants exhibit reduced levels of methyl-esterified homogalacturonan.
Figure 5B:
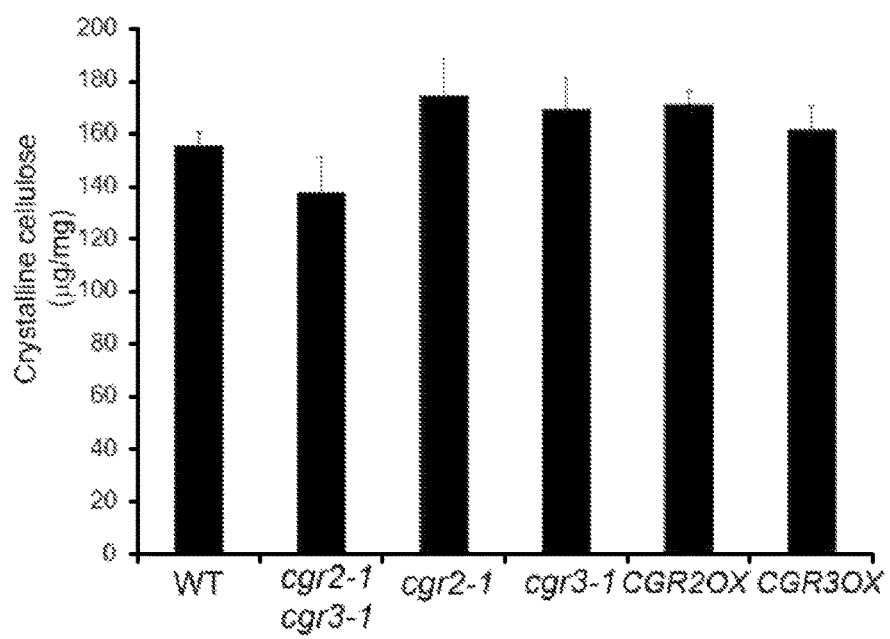
Figure 5C:
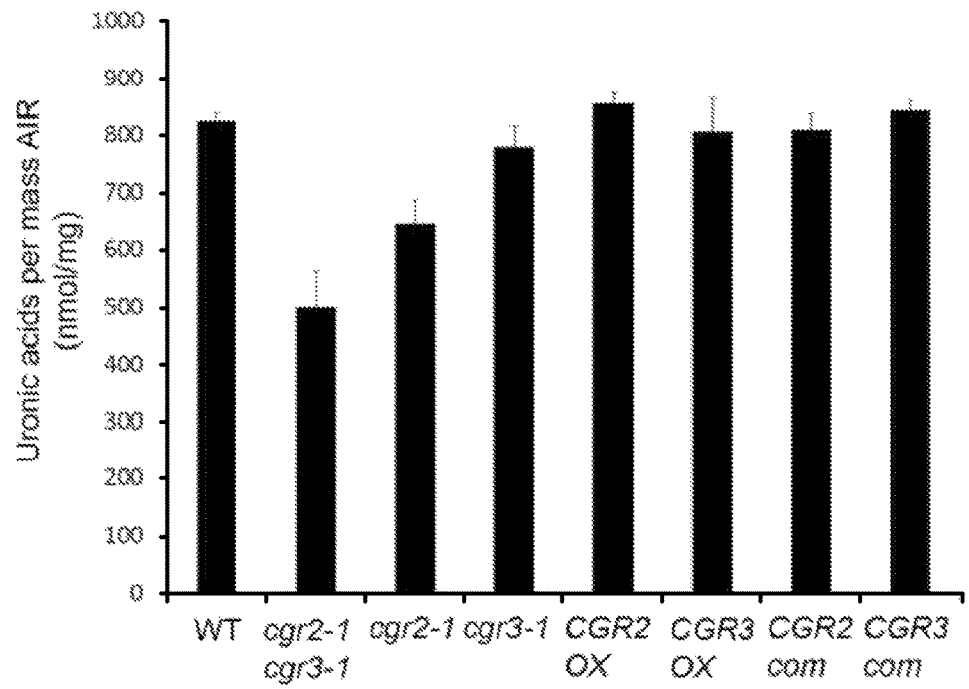

Previously, the neutral sugar composition of the hypocotyls of cgr3-1, the tsd2 mutant, as well as the qua2 mutant have been reported to be similar to wild type (Krupkova et al., 2007; Mouille et al., 2007; Held et al., 2011). Similarly, the neutral sugar composition of the leaf tissue of cgr3-1 mutant and CGR3 overexpressing plant was not different from that of wild type (FIG. 5A). However, investigation of the neutral sugar composition of leaf tissue of cgr2-1 cgr3-1 mutant revealed a large increase in arabinose, which was also observed in the cgr2-1 mutant (FIG. 5A). The analysis of uronic acid and methyl ester further supported the immunofluorescence results. A 40% of reduction in uronic acids was observed in the cgr2-1 cgr3-1 mutant, and cgr2-1 mutant also showed 22% decreased uronic acids compared to wild type. However, cgr3-1 mutant showed only 5% reduction of uronic acids, and CGR2OX and CGR3OX showed similar amounts of uronic acids to wild type (FIG. 5C).

Figure 5D:
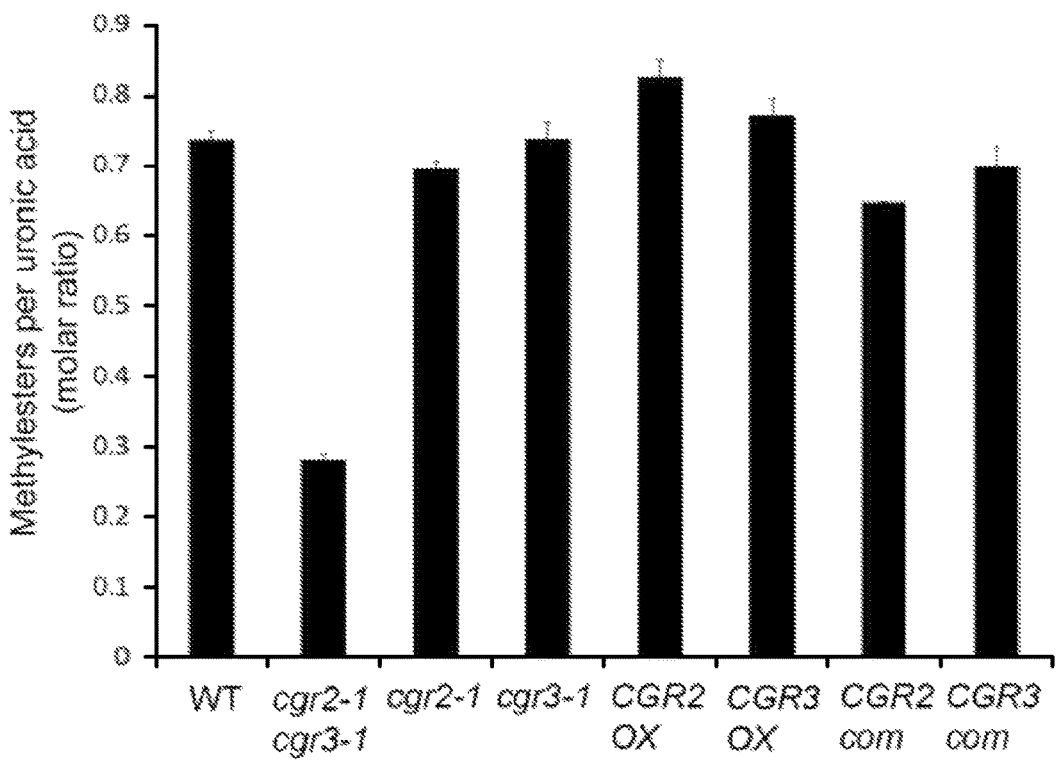

To determine whether a decrease of uronic acids is also closely connected to the degree of methyl-esterification of pectin, methyl ester assays were performed using AIR. Pectins are rich in galacturonic acid. The methyl esters per mole of uronic acid from leaf tissue of wild type were similar to previous results from hypocotyl (Held et al., 2011). Although a reduction of methyl esters in the hypocotyl of cgr3-1 and CGR3OX had been observed previously by the inventors (Held et al., 2011), methyl esters in the leaf tissue of cgr3-1 mutant was not different from that of wild type. Increased methyl esters per mole of uronic acid were also observed from CGR2OX and CGR3OX leaves, which overexpress CGR2 and CGR3. Strong JIM7 labeling was observed in the traverse-sections of CGR2OX and CGR3OX leaf (FIG. 3). Methyl esterification of homogalacturonan in cgr2-1 was only 5% decreased compared to wild type, although cgr2-1 had 22% less uronic acid than wild type. A dramatic difference in methyl ester content per mole of uronic acid was observed in the cgr2-1 cgr3-1 (FIG. 5D). The ratio of methyl esters per mole of uronic acid in wild type was 0.72, while cgr2-1 cgr3-1 was 0.38, suggesting that methyl ester content is greatly reduced in cgr2-1 cgr3-1. These results indicate that loss of highly methyl-esterified homogalacturonan in the cgr2-1 cgr3-1 mutant correlates with reduction in both uronic acids and methyl esters, and such losses also cause of the defects in cell elongation, as well as decreased labeling of JIM7 antibody in the traverse sections of the cgr2-1 cgr3-1 mutant established by immunofluorescence. Quantification of uronic acid and methyl ester in the complemented lines showed similar level to wild type (FIGS. 5C and 5D), supporting that the lack of uronic acid and methyl ester in the cgr2-1 cgr3-1 are specifically due to loss of CGR2 and CGR3.

Example 7: CGR2 and CGR3 are Bona Fide Methyltransferases

This Example provides more evidence that CGR2 and CGR3 are directly involved in homogalacturonan methyl-esterification.

The methyltransferase activity of isolated microsomal fractions was measured from tobacco suspension cells, soybean hypocotyls, and etiolated pea epicotyls using digested homogalacturonan as substrate (Goubet et al., 1998; Ishikawa et al., 2000; Ibar and Orellana, 2007; Miao et al., 2011). Microsomal fractions were isolated from the stems of wild type, cgr2-1 cgr3-1 mutant, CGR2OX and CGR3OX plants grown in soil for 5-6 weeks.

Figure 6:
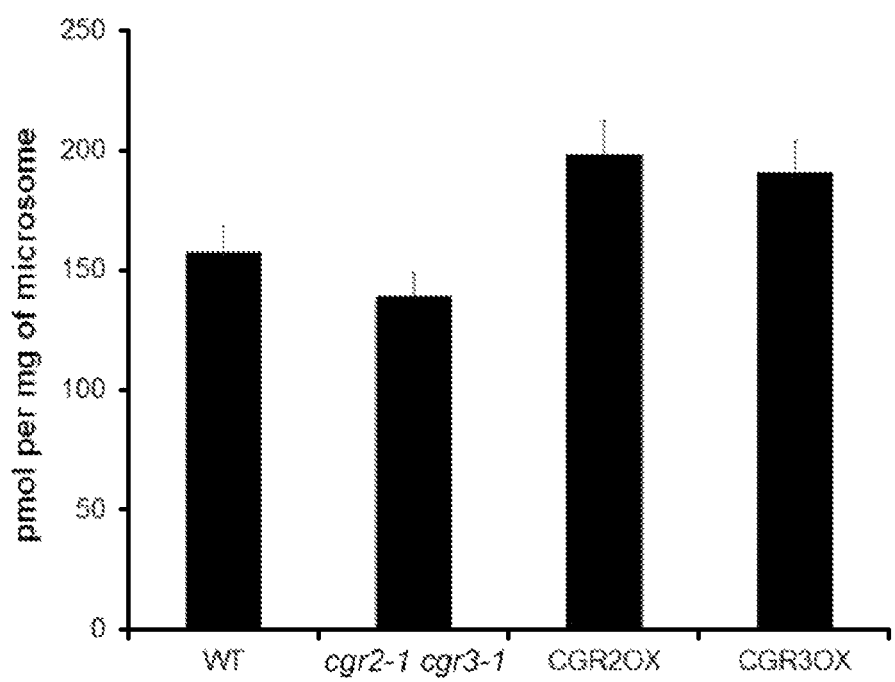
FIG. 6 graphically illustrates the methyltransferase enzyme activity in microsomes from various plant types. Methyltransferase activity was measured in the presence of 50 μg of oligogalacturonic acid (OG) and 6 μM [methyl-$^{14}$C] SAM and 24 μM non-labeled SAM in STM buffer. Oligogalacturonic acid was precipitated in 20% (w/v) TCA and the radioactivity incorporated into the pellet was measured using a liquid scintillation counter. Error bars represent SE from three independent experiments.

FIG. 6 shows that higher methyltransferase activity is present in stems from CGR2OX and CGR3OX transgenic plants while slightly lower methyltransferase activity is present in the stems of cgr2-1 cgr3-1 mutant plants. Contrary to the severe dwarf phenotype of cgr2-1 cgr3-1 mutant plants, the slightly reduced methyltransferase activity of the cgr2-1 cgr3-1 mutant suggests that another gene may compensate for the reduced CGR2 and CGR3 methyltransferase activity, for example, QUA2, even though, the transcript levels of QUA2 in 2-week old cgr2-1 cgr3-1 seedlings were unchanged (FIG. 2G).

Example 8: Increased Glucose Yields from Plant Tissues Expressing High Levels of CGR2 or CGR3

This Example describes experiments demonstrating that digestion of plant tissues that express increased levels of CGR2 or CGR3 increases glucose yields.

Methods

Leaves from five week old wild type, CGR2OX and CGR3OX transgenic plants were harvested and lyophilized, followed by grinding to make a fine powder of raw biomass. The plant biomass materials (3 mg) were resuspended in 200 µl of 50 mM Citrate buffer (pH 5). The commercially available enzyme preparations Cellic Ctec and Htec were mixed at a ratio of 75:25. Varying amounts of Ctec:Htec (75:25)(0, 15, 30 µg) were added to the plant biomass suspensions and water was added so that the total volume of each sample was 500 µl. The assays therefore all contained the same amount of plant (3 mg/sample), with increasing amounts of enzyme (0-30 μg).

The assay plates were incubated for 24 h at 50° C., with constant rotation. After 24 h, the plates were centrifuged and 6 or 12 μl of each well was mixed with 192 μl of GOPOD reagent (glucose oxidase/peroxidase reagent available from Megazyme) to measure the amount of glucose in each assay mixture. The assay plates were incubated at 50° C. for 20 min, to allow color formation (a dark pink color). The absorbance was observed at OD 510 nm and is directly proportional to the amount of glucose released from the plant biomass. A control of pure glucose was used (0-1 mg/ml) to generate a standard curve.

Results

The percentage of pectin that was methylesterified in the different plant biomasses is summarized below.

Figure 7:
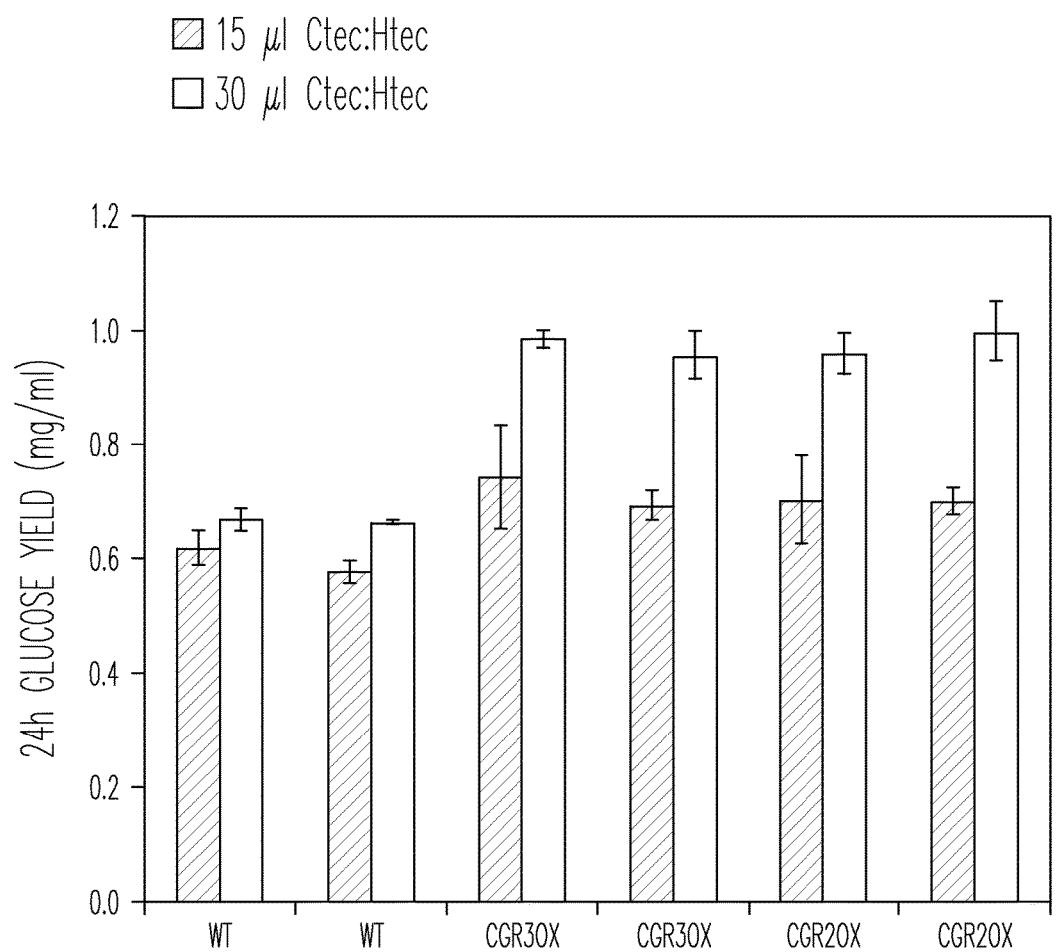
FIG. 7 graphically illustrates glucose yields from enzymatically digested plant biomasses. The commercially available enzyme mixture, Cellic Ctec:Htec, was used for digestion of biomass from various plant types. As shown, wild type plants yield significantly less glucose than plants that overexpress the CGR2 (CGR2OX) and CGR3 (CGR3OX) methyltransferases when the same amount of biomass is digested under the same conditions.

Wild Type: 73% methylesterified pectin
CGR3OX: 77% methylesterified pectin
CGR2OX: 82% methylesterified pectin FIG. 7 and Table 2 show the amounts of glucose released upon enzymatic digestion of the different plant tissues.

TABLE 2

Glucose Released from Plant Biomass

| Digestibility (value from the figure) | 15 μl Ctec:Htec (glucose yield mg/ml) | 30 μl Ctec:Htec (glucose yield mg/ml) |
| --- | --- | --- |
| WT | 0.619181 | 0.668842 |
| WT | 0.578765 | 0.664401 |
| CGR3OX | 0.743694 | 0.984232 |
| CGR3OX | 0.693974 | 0.956109 |
| CGR2OX | 0.702945 | 0.96055 |
| CGR2OX | 0.700468 | 0.998218 |

These data demonstrate that more fermentable sugar can be released upon digestion of plant tissues that express increased levels of CGR2 or CGR3. Accordingly, plant tissues that overexpress CGR2 or CGR3 are more readily digested by enzymes that are commonly used to process plant biomass into fermentable sugars.

Example 9: Digestion of Plant Biomass that Overexpresses CGR2 and CGR3

This Example illustrates digestion of biomass from plants that overexpress CGR2 and CGR3.

Materials and Methods

Biomasses from wild-type, CGR2 and CGR3 overexpression lines (CGR2OX and CGR3OX respectively) were pretreated under different conditions. The conditions involved treatment with EDTA, pectinase or AHP followed by release of glucose with digestion by enzyme mixture (Ctec:Htec). The glucose released was measured using GOPOD method.

Pretreatment of Biomass Using EDTA:

Three mg of biomass from wild-type, CGR2 and CGR3 overexpression lines were pretreated with 100 mM EDTA for 1 hr at 24° C. Pretreated samples were then washed four times with water, to remove EDTA. The resulting samples were resuspended in 25 mM sodium citrate pH 6. Then, Ctec:Htec (75:25) enzymes were added to the mixture and incubated for an additional 24 h at 50° C. Glucose yield was measured using the GOPOD reagent.

Pretreatment of Biomass Using Pectinase:

Three mg of biomass from wild-type, CGR2 and CGR3 overexpression lines were pretreated with 40 U of *Aspergillus niger* pectinase (Sigma) in 25 mM sodium citrate pH 6 at 50° C. for 24 hr. Then, Ctec:Htec (75:25) were added to the mixture and incubated for an additional 24 h at 50° C. Glucose yield was measured using the GOPOD reagent.

Alkaline Hydrogen Peroxide Pretreatment:

A solution of $H_2O_2$ (diluted from a commercial 30% stock, J. T. Baker ACS Reagent Grade) was titrated to pH 11.5 (±0.2) with 5 M NaOH. AHP conditions were 10% biomass loading and an $H_2O_2$ loading of 0.5 g/g biomass. Samples in pretreatment solution were incubated at 24° C. for 24 hr with shaking at 90 rpm. After AHP pretreatment, the biomass suspensions were neutralized to approximately pH 7 with concentrated HCl, treated with catalase to destroy residual $H_2O_2$, heated at 90° C. for 15 min to inactivate the catalase, and lyophilized to dryness. The resulting pretreated samples were resuspended in 25 mM sodium citrate pH 6. Then, Ctec:Htec (75:25) enzymes were added to the mixture and incubated for an additional 24 h at 50° C. Glucose yield was measured using the GOPOD reagent.

Results

Figure 8A:
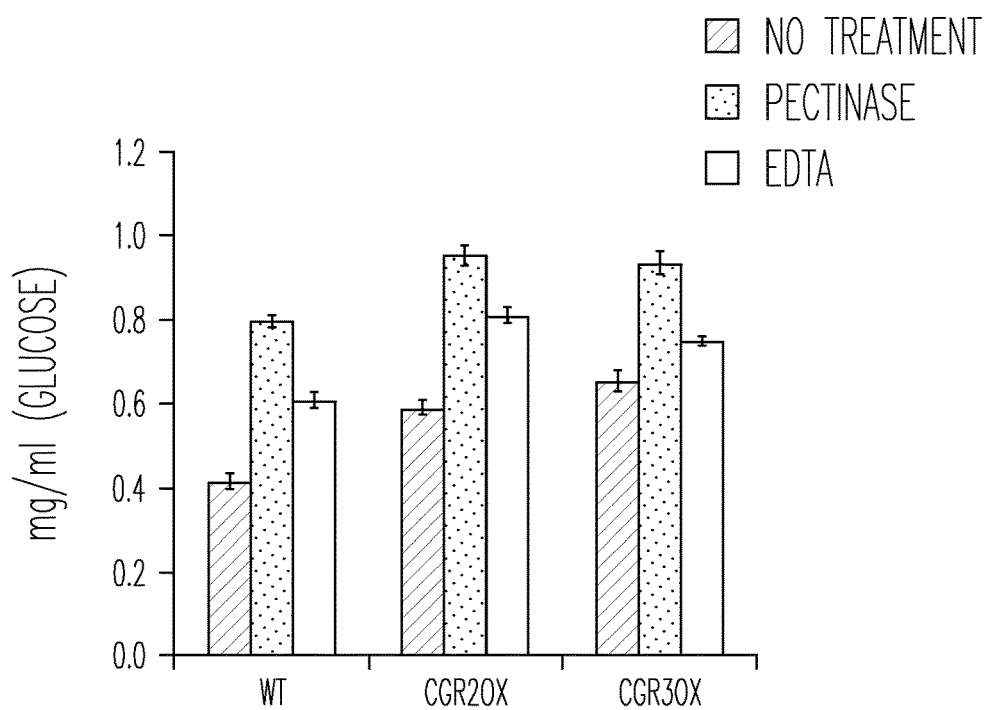
FIG. 8A-8B graphically illustrate that plant biomass from plants that overexpress CGR2OX and CGR3OX exhibit improved digestibility compared to wild-type plant biomass after all types of pretreatment.
Figure 8B:
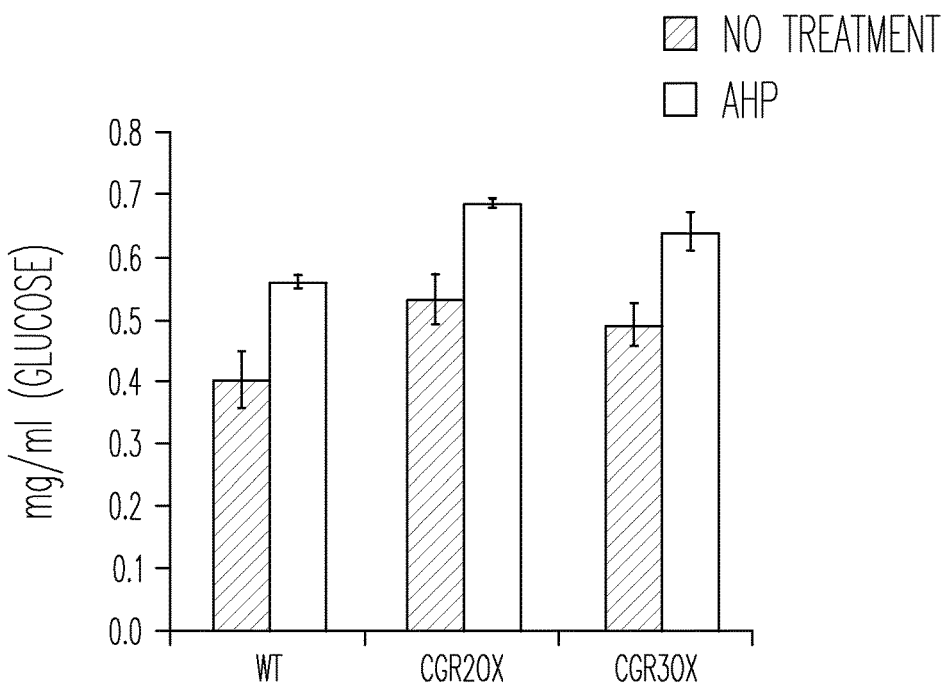

As shown in FIG. 8A-B, plant biomass from plants that overexpress CGR2OX and CGR3OX exhibit improved digestibility compared to wild-type plant biomass after all types of pretreatment.

REFERENCES

Atmodjo, M. A., Sakuragi, Y., Zhu, X., Burrell, A. J., Mohanty, S. S., Atwood, J. A., 3rd, Orlando, R., Scheller, H. V., and Mohnen, D. (2011). Galacturonosyltransferase (GAUT)1 and GAUT7 are the core of a plant cell wall pectin biosynthetic homogalacturonan:galacturonosyltransferase complex. Proc. Natl. Acad. Sci. USA 108, 20225-20230.

Batoko, H., Zheng, H. Q., Hawes, C., and Moore, I. (2000). A rab1 GTPase is required for transport between the endoplasmic reticulum and golgi apparatus and for normal golgi movement in plants. Plant Cell 12, 2201-2218.

Bosch, M., and Hepler, P. K. (2005). Pectin methylesterases and pectin dynamics in pollen tubes. Plant Cell 17, 3219-3226.

Bosch, M., Cheung, A. Y., and Hepler, P. K. (2005b). Pectin methylesterase, a regulator of pollen tube growth. Plant Physiol. 138, 1334-1346.

Bouton, S., Leboeuf, E., Mouille, G., Leydecker, M. T., Talbotec, J., Granier, F., Lahaye, M., Hofte, H., and Truong, H. N. (2002). QUASIMODO1 encodes a putative membrane bound glycosyltransferase required for normal pectin synthesis and cell adhesion in *Arabidopsis*. Plant Cell 14, 2577-2590.

Brandizzi, F., Fricker, M., and Hawes, C. (2002). A greener world: the revolution in plant bioimaging. Nat. Rev. Mol. Cell Biol 3, 520-530.

Carpita, N. C., and Gibeaut, D. M. (1993). Structural models of primary cell walls in flowering plants: consistency of molecular structure with the physical properties of the walls during growth. Plant J. 3, 1-30.

Clausen, M. H., Willats, W. G., and Knox, J. P. (2003). Synthetic methyl hexagalacturonate hapten inhibitors of anti-homogalacturonan monoclonal antibodies LM7, JIM5 and JIM7. Carbohydr. Res. 338, 1797-1800.

Cosgrove, D. J. (2005). Growth of the plant cell wall. Nat. Rev. Mol. Cell Biol. 6, 850-861.

Derbyshire, P., McCann, M. C., and Roberts, K. (2007). Restricted cell elongation in *Arabidopsis* hypocotyls is associated with a reduced average pectin esterification level. BMC Plant Biol. 7, 31.

Dunkley, T. P., Hester, S., Shadforth, I. P., Runions, J., Weimar, T., Hanton, S. L., Griffin, J. L., Bessant, C., Brandizzi, F., Hawes, C., Watson, R. B., Dupree, P., and Lilley, K. S. (2006). Mapping the *Arabidopsis* organelle proteome. Proc. Natl. Acad. Sci. USA 103, 6518-6523.

Ezaki, N., Kido, N., Takahashi, K., and Katou, K. (2005). The role of wall Ca2+ in the regulation of wall extensibility during the acid-induced extension of soybean hypocotyl cell walls. Plant Cell Physiol. 46, 1831-1838.

Filisetti-Cozzi, T. M., and Carpita, N.C. (1991). Measurement of uronic acids without interference from neutral sugars. Anal. Biochem. 197, 157-162.

Foster, C. E., Martin, T. M., and Pauly, M. Comprehensive compositional analysis of plant cell walls (Lignocellulosic biomass) part I: lignin. J. Vis. Exp.

Francis, K. E., Lam, S. Y., and Copenhaver, G. P. (2006). Separation of *Arabidopsis* pollen tetrads is regulated by QUARTET 1, a pectin methylesterase gene. Plant Physiol. 142, 1004-1013.

Gendreau, E., Traas, J., Desnos, T., Grandjean, O., Caboche, M., and Hofte, H. (1997). Cellular basis of hypocotyl growth in *Arabidopsis thaliana*. Plant Physiol. 114, 295-305.

Goubet, F., and Mohnen, D. (1999). Subcellular localization and topology of homogalacturonan methyltransferase in suspension-cultured *Nicotiana tabacum* cells. Planta 209, 112-117.

Goubet, F., Council, L. N., and Mohnen, D. (1998). Identification and partial characterization of the pectin methyltransferase "homogalacturonan-methyltransferase" from membranes of tobacco cell suspensions. Plant Physiol. 116, 337-347.

Held, M. A., Be, E., Zemelis, S., Withers, S., Wilkerson, C., and Brandizzi, F. (2011). CGR3: a Golgi-localized protein influencing homogalacturonan methylesterification. Mol. Plant 4, 832-844.

Ibar, C., and Orellana, A. (2007). The import of S-Adenosylmethionine into the golgi apparatus is required for the methylation of homogalacturonan. Plant Physiol. 145, 504-512.

Ishikawa, M., Kuroyama, H., Takeuchi, Y., and Tsumuraya, Y. (2000). Characterization of pectin methyltransferase from soybean hypocotyls. Planta 210, 782-791.

Krupkova, E., Immerzeel, P., Pauly, M., and Schmulling, T. (2007). The TUMOROUS SHOOT DEVELOPMENT2 gene of *Arabidopsis* encoding a putative methyltransferase is required for cell adhesion and co-ordinated plant development. Plant J. 50, 735-750.

Lee, C., Teng, Q., Zhong, R., Yuan, Y., Haghighat, M., and Ye, Z. H. (2012). Three *Arabidopsis* DUF579 domain-containing GXM proteins are methyltransferases catalyzing 4-o-methylation of glucuronic acid on xylan. Plant Cell Physiol. 53, 1934-1949.

Li, Y. Q., Mareck, A., Faleri, C., Moscatelli, A., Liu, Q., and Cresti, M. (2002). Detection and localization of pectin methylesterase isoforms in pollen tubes of *Nicotiana tabacum* L. Planta 214, 734-740.

Liepman, A. H., Wilkerson, C. G., and Keegstra, K. (2005). Expression of cellulose synthase-like (Csl) genes in insect cells reveals that CslA family members encode mannan synthases. Proc. Natl. Acad. Sci. USA 102, 2221-2226.

Lionetti, V., Francocci, F., Ferrari, S., Volpi, C., Bellincampi, D., Galletti, R., D'Ovidio, R., De Lorenzo, G., and Cervone, F. (2010). Engineering the cell wall by reducing demethylesterified homogalacturonan improves saccharification of plant tissues for bioconversion. Proc. Natl. Acad. Sci. USA 107, 616-621.

Miao, Y. S., Li, H. Y., Shen, J. B., Wang, J. Q., and Jiang, L. W. (2011). QUASIMODO 3 (QUA3) is a putative homogalacturonan methyltransferase regulating cell wall biosynthesis in *Arabidopsis* suspension-cultured cells. J. Exp. Bot. 62, 5063-5078.

Mohnen, D. (2008). Pectin structure and biosynthesis. Curr. Opin. Plant Biol. 11, 266-277.

Mouille, G., Ralet, M. C., Cavelier, C., Eland, C., Effroy, D., Hematy, K., McCartney, L., Truong, H. N., Gaudon, V., Thibault, J. F., Marchant, A., and Hofte, H. (2007). Homogalacturonan synthesis in *Arabidopsis thaliana* requires a Golgi-localized protein with a putative methyltransferase domain. Plant J. 50, 605-614.

Obayashi, T., Nishida, K., Kasahara, K., and Kinoshita, K. (2011). ATTED-II updates: condition-specific gene coexpression to extend coexpression analyses and applications to a broad range of flowering plants. Plant Cell Physiol. 52, 213-219.

O'Neill, M., Albersheim, P., and Darvill, A. (1990). The pectic polysaccharides of primary cell walls. In Methods in Plant Biochemistry, 2nd edn, Dey P. M., ed. (London: Academic Press), pp. 415-441.

Richard, L., Qin, L. X., and Goldberg, R. (1996). Clustered genes within the genome of *Arabidopsis thaliana* encoding pectin methylesterase-like enzymes. Gene 170, 207-211.

Ridley, B. L., O'Neill, M. A., and Mohnen, D. (2001). Pectins: structure, biosynthesis, and oligogalacturonide-related signaling. Phytochemistry 57, 929-967.

Rockel, N., Wolf, S., Kost, B., Rausch, T., and Greiner, S. (2008). Elaborate spatial patterning of cell-wall PME and PMEI at the pollen tube tip involves PMEI endocytosis, and reflects the distribution of esterified and de-esterified pectins. Plant J. 53, 133-143.

Sterling, J. D., Atmodjo, M. A., Inwood, S. E., Kumar Kolli, V. S., Quigley, H. F., Hahn, M. G., and Mohnen, D. (2006). Functional identification of an *Arabidopsis* pectin biosynthetic homogalacturonan galacturonosyltransferase. Proc. Natl. Acad. Sci. USA 103, 5236-5241.

Suzuki, T., Tomita-Yokotani, K., Yoshida, S., Takase, Y., Kusakabe, I., and Hasegawa, K. (2002). Preparation and Isolation of Oligogalacturonic Acids and Their Biological Effects in Cockscomb (*Celosia argentea* L.) Seedlings. J. Plant Growth Regul. 21, 209-215.

Tian, G. W., Chen, M. H., Zaltsman, A., and Citovsky, V. (2006). Pollen-specific pectin methylesterase involved in pollen tube growth. Dev. Biol. 294, 83-91.

Urbanowicz, B. R., Pena, M. J., Ratnaparkhe, S., Avci, U., Backe, J., Steet, H. F., Foston, M., Li, H., O'Neill, M. A., Ragauskas, A. J., Darvill, A. G., Wyman, C., Gilbert, H. J., and York, W. S. (2012). 4-O-methylation of glucuronic acid in *Arabidopsis* glucuronoxylan is catalyzed by a domain of unknown function family 579 protein. Proc. Natl. Acad. Sci. USA 109, 14253-14258.

Vannier, M. P., Thoiron, B., Morvan, C., and Demarty, M. (1992). Localization of methyltransferase activities throughout the endomembrane system of flax (*Linum usitatissimum* L) hypocotyls. Biochem. J. 286 (Pt 3), 863-868.

Verhertbruggen, Y., Marcus, S. E., Haeger, A., Ordaz-Ortiz, J. J., and Knox, J. P. (2009). An extended set of monoclonal antibodies to pectic homogalacturonan. Carbohydr. Res. 344, 1858-1862.

Wen, F., Zhu, Y., and Hawes, M. C. (1999). Effect of pectin methylesterase gene expression on pea root development. Plant Cell 11, 1129-1140.

Willats, W. G., Orfila, C., Limberg, G., Buchholt, H. C., van Alebeek, G. J., Voragen, A. G., Marcus, S. E., Christensen, T. M., Mikkelsen, J. D., Murray, B. S., and Knox, J. P. (2001). Modulation of the degree and pattern of methyl-esterification of pectic homogalacturonan in plant cell walls. Implications for pectin methyl esterase action, matrix properties, and cell adhesion. J. Biol. Chem. 276, 19404-19413.

Winter, D., Vinegar, B., Nahal, H., Ammar, R., Wilson, G. V., and Provart, N. J. (2007). An "Electronic Fluorescent Pictograph" browser for exploring and analyzing large-scale biological data sets. PLoS One 2, e718.

Wood, P. J., and Siddiqui, I. R. (1971). Determination of methanol and its application to measurement of pectin ester content and pectin methyl esterase activity. Anal. Biochem. 39, 418-428.

York, W., Darvill, A., McNeil, M., Stevenson, T. T., and Albersheim, P. (1985). Isolation and characterization of plant cell walls and cell wall components. In Methods in Enzymology, Weissbach A. and Weissbach H., eds. (Orlando, Fla.: Academic Press), 3-40.

Zhang, G. F., and Staehelin, L. A. (1992). Functional compartmentation of the Golgi apparatus of plant cells: immunocytochemical analysis of high-pressure frozen- and freeze-substituted sycamore maple suspension culture cells. Plant Physiol. 99, 1070-1083.

Zhang, G. Y., Feng, J., Wu, J., and Wang, X. W. (2010). BoPMEI1, a pollen-specific pectin methylesterase inhibitor, has an essential role in pollen tube growth. Planta 231, 1323-1334.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods, devices and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The following statements describe some of the elements or features of the invention.

Statements:

1. A plant comprising: an expression cassette comprising an isolated nucleic acid segment encoding a CGR2 enzyme (or a CGR2 methyltransferase segment that has methyltransferase activity) and/or an isolated nucleic acid segment encoding a CGR3 enzyme (or a CGR3 methyltransferase segment that has methyltransferase activity), wherein the expression cassette expresses the CGR2 enzyme (or the CGR2 methyltransferase segment) and/or the CGR3 enzyme (or the CGR3 methyltransferase segment), or can be induced to express the CGR2 enzyme (or the CGR2 methyltransferase segment) and/or the CGR3 enzyme (or the CGR3 methyltransferase segment), at levels sufficient to increase the plant's biomass by at least 5% compared to a wild type plant of the same species that does not comprise the expression cassette.

2. The plant of statement 1, wherein expression cassette comprises a heterologous promoter operably linked to the isolated nucleic acid segment encoding a CGR2 enzyme (or CGR2 methyltransferase segment) and/or the isolated nucleic acid segment encoding a CGR3 enzyme (or CGR3 methyltransferase segment).

3. The plant of statement 1 or 2, wherein expression cassette comprises a first heterologous promoter operably linked to the isolated nucleic acid segment encoding a CGR2 enzyme (or CGR2 methyltransferase segment) and a second heterologous promoter operably linked to the isolated nucleic acid segment encoding a CGR3 enzyme (or CGR3 methyltransferase segment).

4. The plant of any of statements 1-3, wherein the plant's biomass is increased by at least 10%, or at least 15%, or at least 20%, or at least 25%, or at least 30%, or at least 33% compared to a wild type plant of the same species that does not comprise the CGR2 expression cassette or the CGR3 expression cassette.

5. The plant of any of statements 1-4, wherein the plant's pectin has at least 10%, or at least 15%, or at least 20%, or at least 25%, or at least 30%, or at least 33% more methylesters than a wild type plant of the same species that does not have the expression cassette.

6. The plant of any of statements 1-5, wherein upon enzymatic digestion of biomass from the plant at least 10%, or at least 15%, or at least 20%, or at least 25%, or at least 30%, or at least 35%, or at least 40%, or at least 45%, or at least 50% more fermentable sugar is recovered than from a wild type plant biomass of the same species that does not have the expression cassette and is digested by the same procedure.

7. The plant of any of statements 1-6, wherein the CGR2 enzyme has at least 60% amino acid sequence identity to any of SEQ ID NO:2, 5, 7, 9, 11, 13, 15, 17, 19, 21, 23 or 24.

8. The plant of any of statements 1-7, wherein the CGR2 enzyme has at least 60% amino acid sequence identity to any of SEQ ID NO:2, 5, 7, 9, 11, 13, 15, or 17.

9. The plant of any of statements 1-8, wherein the CGR2 enzyme has at least 70%, or at least 80%, or at least 90% or at least 95% amino acid sequence identity to any of SEQ ID NO:2, 5, 7, 9, 11, 13, 15, 17, 19, 21, 23 or 24.

10. The plant of any of statements 1-9, wherein the CGR3 enzyme has at least 60% amino acid sequence identity to any of SEQ ID NO:2, 5, 7, 9, 11, 13, 15, 17, 19, 21, 23 or 24.

11. The plant of any of statements 1-10, wherein the CGR3 enzyme has at least 60% amino acid sequence identity to any of SEQ ID NO: 19, 21, 23 or 24.

12. The plant of any of statements 1-11, wherein the CGR3 enzyme has at least 70%, or at least 80%, or at least 90% or at least 95% amino acid sequence identity to any of SEQ ID NO:2, 5, 7, 9, 11, 13, 15, 17, 19, 21, 23 or 24.

13. The plant of any of statements 1-12, wherein the heterologous promoter for the CGR2 expression cassette or the CGR3 expression cassette is independently selected from a plant gene promoter, a bacterial gene promoter, a plant housekeeping gene promoter, a tissue-specific promoter, or an inducible promoter.

14. The plant of any of statements 1-13, wherein the heterologous promoter for the CGR2 expression cassette or the CGR3 expression cassette is independently selected from a dermal tissue-specific promoter, a vascular tissue-specific promoter, or a ground tissue-specific promoter.

15. The plant of any of statements 1-14, wherein the heterologous promoter for the CGR2 expression cassette or the CGR3 expression cassette is independently selected from a cell-wall tissue-specific promoter, a leaf tissue-specific promoter, a xylem tissue-specific promoter, a phloem-specific promoter, a collenchyma cell-specific promoter, a parenchyma-specific promoter, a seed specific promoter, or a meristematic-specific promoter.

16. The plant of any of statements 1-15, wherein the heterologous promoter for the CGR2 expression cassette or the CGR3 expression cassette is independently selected from a cauliflower mosaic virus promoter, a CaMV 35S promoter, a CaMV 19S promoter, a nos promoter, an Adh1 promoter, a sucrose synthase promoter, an α-tubulin promoter, a ubiquitin promoter, an actin promoter, an actin promoter from rice, a cab promoter, a PEPCase promoter, an R gene complex promoter, a poplar xylem-specific secondary cell wall specific cellulose synthase 8 promoter, a Z10 promoter from a gene encoding a 10 kD zein protein, a Z27 promoter from a gene encoding a 27 kD zein protein, a light inducible promoter from the pea rbcS gene, or a phaseolin promoter from beans.

17. The plant of any of statements 1-16, wherein the plant is an oil-producing plant, a starch plant, a forage plant, a vegetable plant, a grain-producing plant, straw-producing plant, a grass plant, a woody plant, a softwood, a hardwood, a gymnosperm, or a legume.

18. The plant of any of statements 1-17, wherein the plant is canola, potato, lupin, sunflower, cottonseed, alfalfa, clover, fescue, cucumber, tomato, maize, wheat, barley, oats, rice, sorghum, millet, rye, switchgrass, prairie grass, wheat grass, sudangrass, sorghum, a poplar, a pine, a *eucalyptus*, a loblolly pine, a Jack pine, a Southern pine, a *Radiata* pine, a spruce, a Douglas fir, aspen, *miscanthus*, willow, bromegrass, or bluestem.

19. The plant of any of statements 1-18, wherein the isolated nucleic acid encoding the CGR2 enzyme and/or the isolated nucleic acid segment encoding a CGR3 enzyme is a cDNA.

20. The plant of any of statements 1-19, wherein the expression cassette comprises a nucleic acid segment encoding a CGR2 methyltransferase segment that has methyltransferase activity and/or an isolated nucleic acid segment encoding a CGR3 methyltransferase segment that has methyltransferase activity.

21. A plant biomass from the plant of any of statements 1-20.

22. A seed from the plant of any of statements 1-21.

23. A seed comprising: an expression cassette comprising an isolated nucleic acid segment encoding a CGR2 enzyme (or a CGR2 methyltransferase segment that has methyltransferase activity) and/or an isolated nucleic acid segment encoding a CGR3 enzyme (or a CGR3 methyltransferase segment that has methyltransferase activity).

24. The seed of statement 23, wherein expression cassette comprises a heterologous promoter operably linked to the isolated nucleic acid segment encoding a CGR2 enzyme and/or the isolated nucleic acid segment encoding a CGR3 enzyme.

25. The seed of statement 23 or 24, wherein expression cassette comprises a first heterologous promoter operably linked to the isolated nucleic acid segment encoding a CGR2 enzyme and a second heterologous promoter operably linked to the isolated nucleic acid segment encoding a CGR3 enzyme.

26. The seed of any of statement 23-25, wherein the plant's biomass is increased by at least 10%, or at least 15%, or at least 20%, or at least 25%, or at least 30%, or at least 33% compared to a wild type plant of the same species that does not comprise the CGR2 expression cassette or the CGR3 expression cassette.

27. The seed of any of statement 23-26, wherein the plant's pectin has at least 10%, or at least 15%, or at least 20%, or at least 25%, or at least 30%, or at least 33% methylesters than a wild type plant of the same species that does not have the expression cassette.

28. The seed of any of statement 23-27, wherein upon enzymatic digestion of biomass from the plant at least 10%, or at least 15%, or at least 20%, or at least 25%, or at least 30%, or at least 35%, or at least 40%, or at least 45%, or at least 50% more fermentable sugar is recovered than from a wild type plant biomass of the same species that does not have the expression cassette.

29. The seed of any of statements 23-28, wherein the CGR2 enzyme has at least 60% amino acid sequence identity to any of SEQ ID NO:2, 5, 7, 9, 11, 13, 15, 17, 19, 21, 23 or 24.

30. The seed of any of statements 23-29, wherein the CGR2 enzyme has at least 60% amino acid sequence identity to any of SEQ ID NO:2, 5, 7, 9, 11, 13, 15, or 17.

31. The seed of any of statements 23-30, wherein the CGR2 enzyme has at least 70%, or at least 80%, or at least 90% or at least 95% amino acid sequence identity to any of SEQ ID NO:2, 5, 7, 9, 11, 13, 15, 17, 19, 21, 23 or 24.

32. The seed of any of statements 23-31, wherein the CGR3 enzyme has at least 60% amino acid sequence identity to any of SEQ ID NO:2, 5, 7, 9, 11, 13, 15, 17, 19, 21, 23 or 24.
33. The seed of any of statements 23-32, wherein the CGR3 enzyme has at least 60% amino acid sequence identity to any of SEQ ID NO: 19, 21, 23 or 24.
34. The seed of any of statements 23-33, wherein the CGR3 enzyme has at least 70%, or at least 80%, or at least 90% or at least 95% amino acid sequence identity to any of SEQ ID NO:2, 5, 7, 9, 11, 13, 15, 17, 19, 21, 23 or 24.
35. The seed of any of statements 23-34, wherein the heterologous promoter for the CGR2 expression cassette or the CGR3 expression cassette is independently selected from a plant gene promoter, a bacterial gene promoter, a plant housekeeping gene promoter, a tissue-specific promoter, or an inducible promoter.
36. The seed of any of statements 23-35, wherein the heterologous promoter for the CGR2 expression cassette or the CGR3 expression cassette is independently selected from a dermal tissue-specific promoter, a vascular tissue-specific promoter, or a ground tissue-specific promoter.
37. The seed of any of statements 23-36, wherein the heterologous promoter for the CGR2 expression cassette or the CGR3 expression cassette is independently selected from a cell-wall tissue-specific promoter, a leaf tissue-specific promoter, a xylem tissue-specific promoter, a phloem-specific promoter, a collenchyma cell-specific promoter, a parenchyma-specific promoter, a seed specific promoter, or a meristematic-specific promoter.
38. The seed of any of statements 23-37, wherein the heterologous promoter for the CGR2 expression cassette or the CGR3 expression cassette is independently selected from a cauliflower mosaic virus promoter, a CaMV 35S promoter, a CaMV 19S promoter, a nos promoter, an Adh1 promoter, a sucrose synthase promoter, an α-tubulin promoter, a ubiquitin promoter, an actin promoter, an actin promoter from rice, a cab promoter, a PEPCase promoter, an R gene complex promoter, a poplar xylem-specific secondary cell wall specific cellulose synthase 8 promoter, a Z10 promoter from a gene encoding a 10 kD zein protein, a Z27 promoter from a gene encoding a 27 kD zein protein, a light inducible promoter from the pea rbcS gene, or a phaseolin promoter from beans.
39. The seed of any of statements 23-38, wherein the plant is an oil-producing plant, a starch plant, a forage plant, a vegetable plant, a grain-producing plant, straw-producing plant, a grass plant, a woody plant, a softwood, a hardwood, a gymnosperm, or a legume.
40. The seed of any of statements 23-39, wherein the plant is canola, potato, lupin, sunflower, cottonseed, alfalfa, clover, fescue, cucumber, tomato, maize, wheat, barley, oats, rice, sorghum, millet, rye, switchgrass, prairie grass, wheat grass, sudangrass, sorghum, a poplar, a pine, a *eucalyptus*, a loblolly pine, a Jack pine, a Southern pine, a *Radiata* pine, a spruce, a Douglas fir, aspen, *miscanthus*, willow, bromegrass, or bluestem.
41. A method comprising digesting biomass from the plant of any of statements 1-20 to yield fermentable sugars.
42. A method comprising:
    obtaining plant biomass from a plant comprising an expression cassette comprising an isolated nucleic acid segment encoding a CGR2 enzyme (or a CGR2 methyltransferase segment that has methyltransferase activity) and/or an isolated nucleic acid segment encoding a CGR3 enzyme (or a CGR3 methyltransferase segment that has methyltransferase activity); and
    digesting the plant biomass to yield fermentable sugars.

43. The method of either statement 42, wherein pectin in the plant biomass has at least 10%, or at least 15%, or at least 20%, or at least 25%, or at least 30%, or at least 33% more methylesters than a wild type plant of the same species that does not have the expression cassette.
44. The method of any of statements 41-43, wherein upon enzymatic digestion of the biomass at least 10%, or at least 15%, or at least 20%, or at least 25%, or at least 30%, or at least 35%, or at least 40%, or at least 45%, or at least 50% more fermentable sugar is recovered than from a wild type plant biomass of the same species that does not have the expression cassette and is digested by the same procedure.
45. A method comprising:
    expressing CGR2 (or a CGR2 methyltransferase polypeptide segment) and/or CGR3 (or a CGR3 methyltransferase polypeptide segment) from an expression cassette at levels sufficient to increase the plant's biomass by at least 5% compared to a wild type plant of the same species that does not comprise the expression cassette;
    wherein the expression cassette comprises at least one heterologous promoter and an isolated nucleic acid segment encoding a CGR2 enzyme (or a CGR2 methyltransferase polypeptide segment) and/or an isolated nucleic acid segment encoding a CGR3 enzyme (or a CGR3 methyltransferase polypeptide segment).
46. The method of any of statements 41-45, wherein at least one heterologous promoter is operably linked to the isolated nucleic acid segment encoding a CGR2 enzyme or to the isolated nucleic acid segment encoding a CGR3 enzyme.
47. The method of any of statements 41-46, wherein the expression cassette is a transgene.
48. The method of any of statements 41-47, wherein the expression cassette is a heterologous to the plant.
49. The method of any of statements 41-48, wherein expression cassette comprises a first heterologous promoter operably linked to the isolated nucleic acid segment encoding a CGR2 enzyme and a second heterologous promoter operably linked to the isolated nucleic acid segment encoding a CGR3 enzyme.
50. The method of any of statement 41-49, wherein the plant's biomass is increased by at least 10%, or at least 15%, or at least 20%, or at least 25%, or at least 30%, or at least 33% compared to a wild type plant of the same species that does not comprise the CGR2 expression cassette or the CGR3 expression cassette.
51. The method of any of statement 41-50, wherein the plant's pectin has at least 10%, or at least 15%, or at least 20%, or at least 25%, or at least 30%, or at least 33% methylesters than a wild type plant of the same species that does not have the expression cassette.
52. The method of any of statement 41-51, wherein upon enzymatic digestion of biomass from the plant at least 10%, or at least 15%, or at least 20%, or at least 25%, or at least 30%, or at least 35%, or at least 40%, or at least 45%, or at least 50% more fermentable sugar is recovered than from a wild type plant biomass of the same species that does not have the expression cassette.
53. The method of any of statements 41-52, wherein the CGR2 enzyme has at least 60% amino acid sequence identity to any of SEQ ID NO:2, 5, 7, 9, 11, 13, 15, 17, 19, 21, 23 or 24.
54. The method of any of statements 41-53, wherein the CGR2 enzyme has at least 60% amino acid sequence identity to any of SEQ ID NO:2, 5, 7, 9, 11, 13, 15, or 17.
55. The method of any of statements 41-54, wherein the CGR2 enzyme has at least 70%, or at least 80%, or at least 90% or at least 95% amino acid sequence identity to any of SEQ ID NO:2, 5, 7, 9, 11, 13, 15, 17, 19, 21, 23 or 24.

56. The method of any of statements 41-55, wherein the CGR3 enzyme has at least 60% amino acid sequence identity to any of SEQ ID NO:2, 5, 7, 9, 11, 13, 15, 17, 19, 21, 23 or 24.

57. The method of any of statements 41-56, wherein the CGR3 enzyme has at least 60% amino acid sequence identity to any of SEQ ID NO: 19, 21, 23 or 24.

58. The method of any of statements 41-57, wherein the CGR3 enzyme has at least 70%, or at least 80%, or at least 90% or at least 95% amino acid sequence identity to any of SEQ ID NO:2, 5, 7, 9, 11, 13, 15, 17, 19, 21, 23 or 24.

59. The method of any of statements 41-58, wherein the heterologous promoter for the CGR2 expression cassette or the CGR3 expression cassette is independently selected from a plant gene promoter, a bacterial gene promoter, a plant housekeeping gene promoter, a tissue-specific promoter, or an inducible promoter.

60. The method of any of statements 41-59, wherein the heterologous promoter for the CGR2 expression cassette or the CGR3 expression cassette is independently selected from a dermal tissue-specific promoter, a vascular tissue-specific promoter, or a ground tissue-specific promoter.

61. The method of any of statements 41-60, wherein the heterologous promoter for the CGR2 expression cassette or the CGR3 expression cassette is independently selected from a cell-wall tissue-specific promoter, a leaf tissue-specific promoter, a xylem tissue-specific promoter, a phloem-specific promoter, a collenchyma cell-specific promoter, a parenchyma-specific promoter, a seed specific promoter, or a meristematic-specific promoter.

62. The method of any of statements 41-61, wherein the heterologous promoter for the CGR2 expression cassette or the CGR3 expression cassette is independently selected from a cauliflower mosaic virus promoter, a CaMV 35S promoter, a CaMV 19S promoter, a nos promoter, an Adh1 promoter, a sucrose synthase promoter, an α-tubulin promoter, a ubiquitin promoter, an actin promoter, an actin promoter from rice, a cab promoter, a PEPCase promoter, an R gene complex promoter, a poplar xylem-specific secondary cell wall specific cellulose synthase 8 promoter, a Z10 promoter from a gene encoding a 10 kD zein protein, a Z27 promoter from a gene encoding a 27 kD zein protein, a light inducible promoter from the pea rbcS gene, or a phaseolin promoter from beans.

63. The method of any of statements 41-62, wherein the plant is an oil-producing plant, a starch plant, a forage plant, a vegetable plant, a grain-producing plant, straw-producing plant, a grass plant, a woody plant, a softwood, a hardwood, a gymnosperm, or a legume.

64. The method of any of statements 41-63, wherein the plant is canola, potato, lupin, sunflower, cottonseed, alfalfa, clover, fescue, cucumber, tomato, maize, wheat, barley, oats, rice, sorghum, millet, rye, switchgrass, prairie grass, wheat grass, sudangrass, sorghum, a poplar, a pine, a *eucalyptus*, a loblolly pine, a Jack pine, a Southern pine, a *Radiata* pine, a spruce, a Douglas fir, aspen, *miscanthus*, willow, bromegrass, or bluestem.

The following claims summarize aspects of the invention.

What is claimed:

1. A plant comprising: a heterologous expression cassette comprising a heterologous promoter operably linked to an isolated nucleic acid segment encoding a methyltransferase CGR2 or CGR3 enzyme with at least 95% amino acid sequence identity to any of SEQ ID NO: 2, 5, 7, 9, 11, 13, 15, 17, 19, 21, 23 or 24, wherein the plant's pectin has at least 10% more methylesters than a wild type plant of the same species that does not have the expression cassette.

2. The plant of claim 1, wherein the expression cassette expresses the CGR2 enzyme and/or the CGR3 enzyme, or can be induced to express the CGR2 enzyme and/or the CGR3 enzyme, at levels sufficient to increase the plant's biomass by at least 5% compared to a wild type plant of the same species that does not, comprise the expression cassette.

3. The plant of claim 1, wherein enzymatic digestion of biomass from the plant releases at least 10% more fermentable sugar than is released than from a wild type plant biomass of the same species that does not have the expression cassette.

4. The plant of claim 1, wherein the heterologous promoter is a plant gene promoter, a bacterial gene promoter, a plant housekeeping gene promoter, a tissue-specific promoter, or an inducible promoter.

5. The plant of claim 1, wherein the heterologous promoter is a dermal tissue-specific promoter, a vascular tissue-specific promoter, or a ground tissue-specific promoter.

6. The plant of claim 1, wherein the heterologous promoter is a cauliflower mosaic virus promoter, a CaMV 35S promoter, a CaMV 19S promoter, a nos promoter, an Adh 1 promoter, a sucrose synthase promoter, an a-tubulin promoter, a ubiquitin promoter, an actin promoter, an actin promoter from rice, a cab promoter, a PEPCase promoter, an R gene complex promoter, a poplar xylem-specific secondary cell wall specific cellulose synthase 8 promoter, a Z10 promoter from a gene encoding a 10 kD zein protein, a Z27 promoter from a gene encoding a 27 kD zein protein, a light inducible promoter from the pea rbcS gene, or a phaseolin promoter from beans.

7. The plant of claim 1, wherein the plant is an oil-producing plant, a starch plant, a forage plant, a vegetable plant, a grain-producing plant, straw-producing plant, a grass plant, a woody plant, a softwood, a hardwood, a gymnosperm, or a legume.

8. A plant biomass from the plant of claim 1.

9. A seed from the plant of claim 1, wherein the seed comprises the heterologous expression cassette of claim 1.

10. A method comprising digesting biomass from the plant of claim 1 to yield fermentable sugars.

11. A method comprising:
obtaining plant biomass from a plant comprising an expression cassette comprising an isolated nucleic acid segment encoding a methyltransferase CGR2 or CGR3 enzyme with at least 95% amino acid sequence identity to any of SEQ ID NO: 2, 5, 7, 9, 11, 13, 15, 17, 19, 21, 23 or 24; and
digesting the plant biomass to yield at least 10% more fermentable sugars than is recovered than from a wild type plant biomass of the same species that does not have the expression cassette and is digested by the same procedure.

12. The method of either claim 10, wherein pectin in the plant biomass has at least 5% more methylesters than a wild type plant of the same species that does not have the expression cassette.

13. A method comprising:
expressing a methyltransferase CGR2 and/or CGR3 enzyme with at least 95% amino acid sequence identity to any of SEQ ID NO: 2, 5, 7, 9, 11, 13, 15, 17, 19, 21, 23 or 24 from a heterologous expression cassette at levels sufficient to increase a plant's biomass by at least 5% compared to a wild type plant of the same species that does not comprise the expression cassette;
wherein the expression cassette comprises at least one heterologous promoter and an isolated nucleic acid segment encoding a CGR2 enzyme and/or an isolated nucleic acid segment encoding a CGR3 enzyme.

14. The method of claim 10, wherein the heterologous promoter for the CGR2 expression cassette or the CGR3 expression cassette is independently selected from a plant gene promoter, a bacterial gene promoter, a plant housekeeping gene promoter, a tissue-specific promoter, or an inducible promoter.

15. The method of claim 10, wherein the heterologous promoter for the CGR2 expression cassette or the CGR3 expression cassette is independently selected from a dermal tissue-specific promoter, a vascular tissue-specific promoter, or a ground tissue-specific promoter, a cell-wall tissue-specific promoter, a leaf tissue-specific promoter, a xylem tissue-specific promoter, a phloem-specific promoter, a collenchyma cell-specific promoter, a parenchyma-specific promoter, a seed specific promoter, or a meristematic-specific promoter.

16. The method of claim 10, wherein the plant is an oil-producing plant, a starch plant, a forage plant, a vegetable plant, a grain-producing plant, straw-producing plant, a grass plant, a woody plant, a softwood, a hardwood, a gymnosperm, or a legume.

17. The method of claim 10, wherein the plant is canola, potato, lupin, sunflower, cottonseed, alfalfa, clover, fescue, cucumber, tomato, maize, wheat, barley, oats, rice, sorghum, millet, rye, switchgrass, prairie grass, wheat grass, sudangrass, sorghum, soybean, a poplar, a pine, a *eucalyptus*, a loblolly pine, a Jack pine, a Southern pine, a *Radiata* pine, a spruce, a Douglas fir, aspen, *miscanthus*, willow, bromegrass, or Western.

* * * * *

UNITED STATES PATENT AND TRADEMARK OFFICE
CERTIFICATE OF CORRECTION

PATENT NO. : 10,202,614 B2
APPLICATION NO. : 14/901904
DATED : February 12, 2019
INVENTOR(S) : Brandizzi et al.

Page 1 of 1

It is certified that error appears in the above-identified patent and that said Letters Patent is hereby corrected as shown below:

On the Title Page

Item (65), in "Prior Publication Data", in Column 1, Line 1, after "Nov. 24, 2016", insert
--¶ Related U.S. Application Data
(60) Provisional application No. 61/842,077, filed on Jul. 2, 2013.--

In the Claims

In Column 113, Line 65, in Claim 2, delete "not," and insert --not-- therefor

In Column 116, Line 35, in Claim 17, delete "Western." and insert --bluestem.-- therefor Signed and Sealed this
Nineteenth Day of May, 2020

Andrei Iancu
*Director of the United States Patent and Trademark Office*

SEQUENCE LISTING

```
<160> NUMBER OF SEQ ID NOS: 55

<210> SEQ ID NO 1
<211> LENGTH: 1139
<212> TYPE: DNA
<213> ORGANISM: Arabidopsis thaliana

<400> SEQUENCE: 1
agtgatatta acacttcgaa gcttcttctt cctttagtaa attcaagtgt gaggtgtgtt      60
tattgataaa gtgctcattt tctcggatct cagatcttag atccaaaccc tcattatttc     120
attgatccaa gatctaatag cttgagcttg ctgggatttt agttatggcg agacggcaag     180
taggttcaac aagacgtgtt ggcgatggtg gaagcttccc ttttgcagga gctttacact     240
caaagtctcg atcttctcca ctactatcta tttgccttgt tcttgtgggg gcttgtcttc     300
tcattggtta tgcttacagt ggtccaggta tatttaaaag tatcaaagaa gttagcaaag     360
ttacaggtga ctattcttgc acagcagaag tccaaagagc cattcctgta cttaagaagg     420
cttatggaga tggcatgcgc aaagtcttgc atgtgggccc tgacacatgc tcagtggttt     480
ccagtctatt gaaagaagaa gagactgaag catggggtgt tgaaccatat gatattgagg     540
atgcagattc tcactgcaag agttttgtga gcaaaggtct tgtacgtgtt gctgatatca     600
agtttcctct gccctaccgg gcaaaatcct tctctcttgt gattgtgtca gatgctctgg     660
attatctctc acccaagtac ctgaacaaga ccgttcctga actcgcaagg gtggcttcag     720
acggtgtggt tcttttttgca ggtctccctg gtcagcagag agctaaagtt gctgaactct     780
ctaaattcgg ccgacccgct aaaatgcgta gcgcatcgtg gtggaaccgc ttttcgtcc     840 agacaaactt agaagaaaac gatgcaccaa gcaagaagtt cgaacaggct gtttccaaag     900
gattatacaa accagcctgc caagtcttcc acctcaagcc attacattaa ccagccacca     960
```

```
ccaaagccta ctggttccac accaaagcat atttacacgt agagccgcac gcgaaaaaaa      1020
aaaatagcgt aatcgatatt tctccttgta ttttgtaaca ggtcagtttt tatccttcaa      1080
tgttgtatcc gccaacacaa ttttttcctat tcaattaaat cataattatt atcaccaat     1139
```

<210> SEQ ID NO 2
<211> LENGTH: 261
<212> TYPE: PRT
<213> ORGANISM: Arabidopsis thaliana

<400> SEQUENCE: 2

```
Met Ala Arg Arg Gln Val Gly Ser Thr Arg Arg Val Gly Asp Gly Gly
  1               5                  10                  15

Ser Phe Pro Phe Ala Gly Ala Leu His Ser Lys Ser Arg Ser Ser Pro
             20                  25                  30

Leu Leu Ser Ile Cys Leu Val Leu Val Gly Ala Cys Leu Leu Ile Gly
         35                  40                  45

Tyr Ala Tyr Ser Gly Pro Gly Ile Phe Lys Ser Ile Lys Glu Val Ser
     50                  55                  60

Lys Val Thr Gly Asp Tyr Ser Cys Thr Ala Glu Val Gln Arg Ala Ile
 65                  70                  75                  80

Pro Val Leu Lys Lys Ala Tyr Gly Asp Gly Met Arg Lys Val Leu His
                 85                  90                  95

Val Gly Pro Asp Thr Cys Ser Val Val Ser Ser Leu Leu Lys Glu Glu
            100                 105                 110

Glu Thr Glu Ala Trp Gly Val Glu Pro Tyr Asp Ile Glu Asp Ala Asp
        115                 120                 125

Ser His Cys Lys Ser Phe Val Ser Lys Gly Leu Val Arg Val Ala Asp
    130                 135                 140

Ile Lys Phe Pro Leu Pro Tyr Arg Ala Lys Ser Phe Ser Leu Val Ile
145                 150                 155                 160

Val Ser Asp Ala Leu Asp Tyr Leu Ser Pro Lys Tyr Leu Asn Lys Thr
                165                 170                 175

Val Pro Glu Leu Ala Arg Val Ala Ser Asp Gly Val Val Leu Phe Ala
            180                 185                 190

Gly Leu Pro Gly Gln Gln Arg Ala Lys Val Ala Glu Leu Ser Lys Phe
        195                 200                 205

Gly Arg Pro Ala Lys Met Arg Ser Ala Ser Trp Trp Asn Arg Phe Phe
    210                 215                 220

Val Gln Thr Asn Leu Glu Glu Asn Asp Ala Pro Ser Lys Lys Phe Glu
225                 230                 235                 240

Gln Ala Val Ser Lys Gly Leu Tyr Lys Pro Ala Cys Gln Val Phe His
                245                 250                 255

Leu Lys Pro Leu His
            260
```

<210> SEQ ID NO 3
<211> LENGTH: 1143
<212> TYPE: DNA
<213> ORGANISM: Arabidopsis thaliana

<400> SEQUENCE: 3

```
attaacactt cgaagcttct tcttccttta gtaaattcaa gtgtgaggtg tgtttattga        60
taaagtgctc attttctcgg atctcagatc ttagatccaa accctcatta tttcattgat       120
ccaagatcta atagcttgag cttgctggga ttttagttat ggcgagacgg caagtaggtt       180
```

```
caacaagacg tgttggcgat ggtggaagct tcccttttgc aggagcttta cactcaaagt      240
ctcgatcttc tccactacta tctatttgcc ttgttcttgt gggggcttgt cttctcattg      300
gttatgctta cagtggtcca ggtatattta aaagtatcaa agaagttagc aaagttacag      360
gtgactattc ttgcacagca gaagtccaaa gagccattcc tgtacttaag aaggcttatg      420
gagatggcat gcgcaaagtc ttgcatgtgg gccctgacac atgctcagtg gtttccagtc      480
tattgaaaga agaagagact gaagcatggg gtgttgaacc atatgatatt gaggatgcag      540
attctcactg caagagtttt gtgagcaaag tcttgtacg tgttgctgat atcaagtttc      600
ctctgcccta ccgggcaaaa tccttctctc ttgtgattgt gtcagatgct ctggattatc      660
tctcacccaa gtacctgaac aagaccgttc tgaactcgc aagggtggct cagacggtg      720 tggttctttt tgcaggtctc cctggtcagc agagagctaa agttgctgaa ctctctaaat      780
tcggccgacc cgctaaaatg cgtagcgcat cgtggtggaa ccgcttttc gtccagacaa      840 acttagaaga aaacgatgca ccaagcaaga agttcgaaca ggctgtttcc aaaggattat      900
acaaaccagc ctgccaagtc ttccacctca gccattaca ttaaccagcc accaccaaag      960
cctactggtt ccacaccaaa gcatatttac acgtagagcc gcacgcgaaa aaaaaaaata     1020
gcgtaatcga tatttctcct tgtattttgt aacaggtcag ttttttatcct tcaatgttgt     1080 atccgccaac acaattttc ctattcaatt aaatcataat tattatcaaa aaaaaaaaa     1140 aaa                                                                 1143

<210> SEQ ID NO 4
<211> LENGTH: 777
<212> TYPE: DNA
<213> ORGANISM: Arabidopsis lyrata

<400> SEQUENCE: 4
atgtcaagaa ggcaagtaag gcgtgtaggg gatagtggaa gcttcccatt tgtaggagct       60
ttgcattcga aatcgcgttc gtctcctttg ttatctgttt gccttgttct cgtgggagca      120
tgccttctca ttggttatgc ttacagtggt ccaggtatgt tcaaaagtat cagagaagtc      180
agcaagatca caggggacta ctcttgcaca gcagaagttc aaagagccat tcctgttctt      240
aagagtgcgt atggagatac catgcgcaaa gtcttgcacg tgggtcccga acatgctca      300 gtcgtctcga gtctgttgaa tgaagaagag acggaagcat ggggtgttga accgtatgat      360
gtggaggatg cagattctaa ctgcaaaagt cttttgcaca aaggccttgt acgtgtggct      420
gacatcaaat tccctctgcc ttaccggtca agtcgttttt ctcttgtgat cgtctcagac      480
gcattggatt acctctcacc caggtacctg aacaaaaccg tgcctgaact tgcacgggtc      540
gcttcagatg gtgtcgttct ttttgcaggt aaccctggtc aacaaaaggc taaaggtgcg      600
gaattgtcga aatttggacg accagctaaa atgcgtagct cgtcctggtg gatccgtttc      660
ttctcacaga cgaacttaga ggaaaacgaa gcagcaatca agaaattcga acaagcagct      720
tccaagagtt catacaaacc agcttgtcaa gttttccacc tcaagccatt acattag      777

<210> SEQ ID NO 5
<211> LENGTH: 258
<212> TYPE: PRT
<213> ORGANISM: Arabidopsis lyrata

<400> SEQUENCE: 5

Met Ser Arg Arg Gln Val Arg Val Gly Asp Ser Gly Ser Phe Pro
1               5                   10                  15
```

```
Phe Val Gly Ala Leu His Ser Lys Ser Arg Ser Ser Pro Leu Leu Ser
            20                  25                  30
Val Cys Leu Val Leu Val Gly Ala Cys Leu Leu Ile Gly Tyr Ala Tyr
        35                  40                  45
Ser Gly Pro Gly Met Phe Lys Ser Ile Arg Glu Val Ser Lys Ile Thr
    50                  55                  60
Gly Asp Tyr Ser Cys Thr Ala Glu Val Gln Arg Ala Ile Pro Val Leu
65                  70                  75                  80
Lys Ser Ala Tyr Gly Asp Thr Met Arg Lys Val Leu His Val Gly Pro
                85                  90                  95
Glu Thr Cys Ser Val Val Ser Ser Leu Leu Asn Glu Glu Thr Glu
            100                 105                 110
Ala Trp Gly Val Glu Pro Tyr Asp Val Glu Asp Ala Asp Ser Asn Cys
        115                 120                 125
Lys Ser Leu Leu His Lys Gly Leu Val Arg Val Ala Asp Ile Lys Phe
    130                 135                 140
Pro Leu Pro Tyr Arg Ser Lys Ser Phe Ser Leu Val Ile Val Ser Asp
145                 150                 155                 160
Ala Leu Asp Tyr Leu Ser Pro Arg Tyr Leu Asn Lys Thr Val Pro Glu
                165                 170                 175
Leu Ala Arg Val Ala Ser Asp Gly Val Val Leu Phe Ala Gly Asn Pro
            180                 185                 190
Gly Gln Gln Lys Ala Lys Gly Ala Glu Leu Ser Lys Phe Gly Arg Pro
        195                 200                 205
Ala Lys Met Arg Ser Ser Ser Trp Trp Ile Arg Phe Phe Ser Gln Thr
    210                 215                 220
Asn Leu Glu Glu Asn Glu Ala Ala Ile Lys Lys Phe Glu Gln Ala Ala
225                 230                 235                 240
Ser Lys Ser Ser Tyr Lys Pro Ala Cys Gln Val Phe His Leu Lys Pro
                245                 250                 255
Leu His
```

`<210>` SEQ ID NO 6
`<211>` LENGTH: 3000
`<212>` TYPE: DNA
`<213>` ORGANISM: Vitis vinifera

`<400>` SEQUENCE: 6

```
tttcatcaat caatggtatg agttgaggtg aaacacctgg catgctggct tgtaagactt      60
cttggctgca gcctgatcaa acttttttgat ggcagcttca ttctcttcta agctggtctg     120
aacaaaatac cgtatccacc aagatgagct tcgcattttt gccttcacac agaaaaaagg     180
cattgggata tgtcatattt taattaaact gaggttttag tgatagaatt caatgttact     240
gaccagaaac gaaccccata ataaacaag gcctgccaaa acaaaatttt ccataccct       300
tttgtctcac tccataataa actaatcatc tcagcagatg cactcatgtt tttttcaatt     360
ttcaagcatg aaatgtaaca atgttacaat ttttttttgga ctaatctttt gtttggtctc   420
tttataaaat taaatattcc actccgtatc ttcctgttgt tattaccaag ttgccattat    480
ttgattgttt tactgtaagt tctaatcata aaaattttgt atggaacaag taaaattgta    540
caagcagtag atcgccactt actggccgtc caaatttgga taactctgca actttagctt    600
tctgttgacc aggaagacct acacagaaat tgaaaacagt gaaaacccat taacattaac   660
cactttttat gtcaattgaa cttttagcgc tagaaaaatt acagatgaag tttatttgcc   720
```

```
caagcaaaca aactactgaa gttcacccgg aggaacctgg agagatataca acatgcaatt    780
aaacaatcat ttagaaatct atttatgtcc aacaggaaag tcacctaaac actaaagaag    840
tttgtattgc ttctaaatcg ttgattgtga tgaaagggta attataggag tttctttcac    900
cgtcaactat caaatcaaaa ccaaagctaa gaggcaagag aaaatatatg atatcatctc    960
tattcacaaa attaccaacc tagcagagag agtgcaatag cttatcatca catcaattgg   1020
gaggttacta aggttgctca tgcattgacc aaaaaggata gctagacaga gagaccagaa   1080
cagcttatca tcgcatcaat tgggaggtta ccgaagttgc tggtgtattg gccaaaaaag   1140
atgtagctag aatgaaatta tttcctaaat catcaagtaa aacaaaaatt ctaccaaata   1200
cgacatattt atatttagca aattttctat agcatgactt tttttatagg ttttttttctt  1260
tctttctact tggaattccc catcccaccc caccccaccc caaccccttg ccactagagc   1320
taggcctcaa gagcctctta tgacgaatat aaatatttca gggaattacc tgcaaaaata   1380
acaagaccat cactggacac ccttgccaaa tcaggaagag tcttgttcaa gtactttgga   1440
gaaaggtaat ccaatgcatc tgacacaata acaagagaaa atgactttgg cctgtagggc   1500
atagggaact tgatatcagc cacacgaaca atgcttttac ggacaagact cttgcagctc   1560
ccatcagcat cctctatgtc atatggttct acaccccatg cttctgtttc ctcctccttt   1620
aacaatttag agaccactga acaggtatca gggcccacat gcaaaacttt gcgcatgctg   1680
tcaccatatg ctttctttag aataggtatt gctctctgaa cttctaaggt gcatgaaaaa   1740
tcacctacat gcattgacat atttgagtct ttctgcagga gataaatagt tccatcctaa   1800
taaaatgaaa ttccaactac cactatcatg aaggttaaag atagtgctaa tggttcttaa   1860
ccacaaaaca tttactagtg ctttatccat accagttcaa acctcatttt tttggccaga   1920
atttcagtag caacttgaga tggaaataat atattactaa aaagctaaaa ccgattagca   1980
ttatgaaatg gctaaattaa aaataaaaac aaaaatgaaa atctaagtct caagaactgg   2040
tagagggtta cagcctttat ctataaagat aaagggtagg aatatttcaa ggtgaccaac   2100
tcgttatact gaatccacga ggaaaccata acaaggacat aataatacaa gaaattatct   2160
tgaataacat ttttggagtt caagtcaaaa gttagaatat cctttcaatc atttccacta   2220
tggaagaaca attgttagtc ttctgtatgg ccatttacaa gagaagaara gatccatggg   2280
cagcaacatt actgaagaaa ttagacaaga agtcatagca ctccatcctg cagactcctg   2340
aacaagaaat ccaacaagat gagaataaaa gagccaaatt ttttttacct tcaaccttac   2400
taaaagcttc cttgtcacca ccaaatagac ctgtattgtg aaaaacaaga tcgaaatcaa   2460
tttaaagaaa gaaaaatgta caactgtcta gaatttcaaa gcaagtatgg caaatcaaga   2520
catgagaatc atcctaagat taaaagtgta atagttcatg atgtagatag ctatctatga   2580
cagcaagaag ccaagttccc atgactagtc cattggattg aaagaaaagc aaatacagac   2640
ctgacccact ataagaataa gcaacaagaa ggaatgcccc ctgcatgttt caagaaaaaa   2700
gaatcagaac ttgtattgtc aaccagaacc acttgtggtg tttctcaaag tggggaaata   2760
tttgggcaac aataaccaat taaccataat ctttaaatga agtaataacc aatgctagaa   2820
attgtcaaaa ggaaaaggtg aaccagagac gagaaatacc agaaggacaa gaccaatgga   2880
taataaggga gaagagcgtg attttgaatg taaggctcct gcaaatggaa tgcttccact   2940
gtccacaaag cgccgtgagg gatttacttg tctccttgac atgactactc ttgtaataca   3000
```

<210> SEQ ID NO 7

<211> LENGTH: 256
<212> TYPE: PRT
<213> ORGANISM: Vitis vinifera

<400> SEQUENCE: 7

```
Met Ser Arg Arg Gln Val Asn Pro Ser Arg Arg Phe Val Asp Ser Gly
 1               5                  10                  15

Ser Ile Pro Phe Ala Gly Ala Leu His Ser Lys Ser Arg Ser Ser Pro
            20                  25                  30

Leu Leu Ser Ile Gly Leu Val Leu Gly Ala Phe Leu Leu Val Ala
         35                  40                  45

Tyr Ser Tyr Ser Gly Ser Asp Ser Asn Met Ser Met His Val Gly Asp
 50                  55                  60

Phe Ser Cys Thr Leu Glu Val Gln Arg Ala Ile Pro Ile Leu Lys Lys
 65                  70                  75                  80

Ala Tyr Gly Asp Ser Met Arg Lys Val Leu His Val Gly Pro Asp Thr
                 85                  90                  95

Cys Ser Val Val Ser Lys Leu Leu Lys Glu Glu Thr Glu Ala Trp
            100                 105                 110

Gly Val Glu Pro Tyr Asp Ile Glu Asp Ala Asp Gly Ser Cys Lys Ser
            115                 120                 125

Leu Val Arg Lys Ser Ile Val Arg Val Ala Asp Ile Lys Phe Pro Met
130                 135                 140

Pro Tyr Arg Pro Lys Ser Phe Ser Leu Val Ile Val Ser Asp Ala Leu
145                 150                 155                 160

Asp Tyr Leu Ser Pro Lys Tyr Leu Asn Lys Thr Leu Pro Asp Leu Ala
                165                 170                 175

Arg Val Ser Ser Asp Gly Leu Val Ile Phe Ala Gly Leu Pro Gly Gln
            180                 185                 190

Gln Lys Ala Lys Val Ala Glu Leu Ser Lys Phe Gly Arg Pro Ala Lys
        195                 200                 205

Met Arg Ser Ser Ser Trp Trp Ile Arg Tyr Phe Val Gln Thr Ser Leu
    210                 215                 220

Glu Glu Asn Glu Ala Ala Ile Lys Lys Phe Asp Gln Ala Ala Ala Lys
225                 230                 235                 240

Lys Ser Tyr Lys Pro Ala Cys Gln Val Phe His Leu Asn Ser Tyr His
                245                 250                 255
```

<210> SEQ ID NO 8
<211> LENGTH: 1323
<212> TYPE: DNA
<213> ORGANISM: Cucumis sativus

<400> SEQUENCE: 8

```
gtatttctat ttcccacttg cacttccttc tttctccacc tctccacctc tccacctctc    60
tacctctcta ccatccatcc tgttggatgt aactacgcca caacgaacta ataaaacccc   120
ccaaaagagg aatttaattt ccagatccaa gatctacact tcacaaact aaatgctgct    180 ttccttcttg tctgatctga tctgaggtgg ttttccagat tccgattcaa tttctcttac   240
ctttgtgttt gattccagaa acatattctt tggaactctt aattatgcaa cggaggcaac   300
ccacttcgac tcgtcgcaat ggaagctttc catttgctgg ggccctcaat gccaaatcaa   360
aagcatctcc cttgctatct atatgcttgg tccttgtggg agcaattctt ctacttgtct   420
atgcttttag tggaccaggt ttatttggag gcaccaagat agtcagcaag attgaaggtg   480 attttttcatg cacattggag ttgcaaagag caatacccat cttaaagaaa gcattcggcg   540
```

```
atagcatgcg caaagttttg catgttggtc ccgatacctg ttctgtggta tccaagctgt    600
tgaaagaagg tgaaacagaa gcatggggca tagaaccata cgacatagaa gatgctgatg    660
gaaagtgcaa atcacttgtg aacaaaggca ttgtacgtgt ggcagatatc aaattccctc    720 tacctatag gtcaaagtca ttttcccacg ttattgtgtc cgatgcattg gactacctat    780 ccccaaata cctgaacaaa actcttccag aatttgcaag ggtttcttct gatggtcttg    840
ttatatttac aggttcccct ggtcaacaga aagctaaagt aaacgagtta tcaaagtttg    900
gacgaccggc caaattgcgg agctcgtctt ggtggattcg attttttgtc caaacaagct   960
tagaagagga cgaaggttct gccaagaaat ttgagcaagc agcatcgaag cagtcttaca   1020
agcccggttg tcaagttttc catctcaatt cataccattg atatcgtgaa atcacaagct   1080
atgaaattat tttcttaccc cctttttgtc tcctttctt ctccgtctta tgttataaac    1140
aaacacaaga gaagctaggg aggtggattt gttttgtttt gttttgtttt ttatatggta   1200
ggttggggga acgttttgg cacataattg tgaaccatag gagatttag tgttctcaaa    1260 ttcttacatt acgatatatt aattattttt tatttaatga gataaatata actgatattc   1320
ata                                                                 1323
```

<210> SEQ ID NO 9
<211> LENGTH: 258
<212> TYPE: PRT
<213> ORGANISM: Cucumis sativus

<400> SEQUENCE: 9

```
Met Gln Arg Arg Gln Pro Thr Ser Thr Arg Arg Asn Gly Ser Phe Pro
  1               5                  10                  15

Phe Ala Gly Ala Leu Asn Ala Lys Ser Lys Ala Ser Pro Leu Leu Ser
             20                  25                  30

Ile Cys Leu Val Leu Val Gly Ala Ile Leu Leu Val Tyr Ala Phe
         35                  40                  45

Ser Gly Pro Gly Leu Phe Gly Gly Thr Lys Ile Val Ser Lys Ile Glu
     50                  55                  60

Gly Asp Phe Ser Cys Thr Leu Glu Leu Gln Arg Ala Ile Pro Ile Leu
 65                  70                  75                  80

Lys Lys Ala Phe Gly Asp Ser Met Arg Lys Val Leu His Val Gly Pro
                 85                  90                  95

Asp Thr Cys Ser Val Val Ser Lys Leu Leu Lys Glu Gly Glu Thr Glu
            100                 105                 110

Ala Trp Gly Ile Glu Pro Tyr Asp Ile Glu Asp Ala Asp Gly Lys Cys
        115                 120                 125

Lys Ser Leu Val Asn Lys Gly Ile Val Arg Val Ala Asp Ile Lys Phe
    130                 135                 140

Pro Leu Pro Tyr Arg Ser Lys Ser Phe Ser His Val Ile Val Ser Asp
145                 150                 155                 160

Ala Leu Asp Tyr Leu Ser Pro Lys Tyr Leu Asn Lys Thr Leu Pro Glu
                165                 170                 175

Phe Ala Arg Val Ser Ser Asp Gly Leu Val Ile Phe Thr Gly Ser Pro
            180                 185                 190

Gly Gln Gln Lys Ala Lys Val Asn Glu Leu Ser Lys Phe Gly Arg Pro
        195                 200                 205

Ala Lys Leu Arg Ser Ser Ser Trp Trp Ile Arg Phe Phe Val Gln Thr
    210                 215                 220
```

Ser Leu Glu Glu Asp Glu Gly Ser Ala Lys Lys Phe Glu Gln Ala Ala
225                 230                 235                 240

Ser Lys Gln Ser Tyr Lys Pro Gly Cys Gln Val Phe His Leu Asn Ser
            245                 250                 255

Tyr His

<210> SEQ ID NO 10
<211> LENGTH: 1426
<212> TYPE: DNA
<213> ORGANISM: Fragaria vesca

<400> SEQUENCE: 10

```
gtagaaatcg gtgtgtccca agctacgact ctcttcaacc ttcagtatta gaaacttagt      60
ctaagctctc caaagtgtaa gaccagcagt ccagcacaga tctgaatcgg ccttcccta     120
gatctcatat tccacttaag gtccattgct attatatcag catgtccagg aggccagtca    180
atcctgctag gcgcattggt gatggtggaa gcatcccatt tgtgggtgcg gtgcaggcca    240
aagcgagctc atcacctgta ctgtctgtag cgcttgtgct tctgggtaca attcttcttg    300
tctgctatgc ttttagcggg tcaggtggag tgagcagtaa agaggctgtg attaaacttg    360
aaggtggtgt ttcatgtaca ctcgaagttc agagagcaat acctatacta agaaggcat    420
atggtgatag catgcataag gtattgcatg taggccctga acatgttca gttgtatcta    480
aattattaaa agaggaggag actgaagcct ggggtgtgga accatatgac ttggaagatg    540
ttgatggaaa ttgcaagagt cttgtgaaca aaggcattgt gcgtgctgct gatataaagt    600
ttcctcttcc ataccgggca aaatcatttt ctctggtaat agtatcagat gcattagatt    660
acttgtctcc gaagtacctc aacagaactc ttccagagtt agcaagggta tctgctgatg    720
gcgtaattat tttctctggt tatccaggtc aacaaagagc taagttgca gagctatcca    780
aatttggccg tccagccaaa ttgcgaagct catcctggtg gataagattt tttgttcaaa    840
caagcttaga agagaatgaa tcagcctcga gaagtttga acaggctgca ttaaagagat    900
cttataagcc cgaatgtcag gtattccacc ttaagtcata ccattgagaa tcacatcatt    960
gtatctttca ttgtatcagt tataccattg cacaaaaggt aactatatat tttgtgaaat   1020
acggaacctc attatgtgct cctttatgag acgagatttc tgatagatgt gtactaagga   1080
atgatttccc aagaattggg tactgtcatc acttttgtatt cttttatacg atgtatttgc   1140
cgcccacatt gctggttctt gttgttgcaa tgatagattt gttagaatgt tcagatatac   1200
atttgttgat tatattgata agacagtcgt atatcgtttt agtgatgcaa tcaattctat   1260
cttttgatgc atgccctcag tggagaagtc aatttccact aaaattaaaa cttattttac   1320
cacgttgagg accttattta cgccatgact ggaggctgta cctgacgcca tggccggagg   1380
ctttacctta atgtgtcata gatccacata gtattgaaaa gggaat                   1426
```

<210> SEQ ID NO 11
<211> LENGTH: 261
<212> TYPE: PRT
<213> ORGANISM: Fragaria vesca

<400> SEQUENCE: 11

Met Ser Arg Arg Pro Val Asn Pro Ala Arg Arg Ile Gly Asp Gly Gly
1               5                   10                  15

Ser Ile Pro Phe Val Gly Ala Val Gln Ala Lys Ala Ser Ser Ser Pro
            20                  25                  30

Val Leu Ser Val Ala Leu Val Leu Leu Gly Thr Ile Leu Leu Val Cys

```
                35                  40                  45
Tyr Ala Phe Ser Gly Ser Gly Val Ser Ser Lys Glu Ala Val Ile
 50                  55                  60
Lys Leu Glu Gly Gly Val Ser Cys Thr Leu Glu Val Gln Arg Ala Ile
 65                  70                  75                  80
Pro Ile Leu Lys Lys Ala Tyr Gly Asp Ser Met His Lys Val Leu His
                 85                  90                  95
Val Gly Pro Glu Thr Cys Ser Val Val Ser Lys Leu Leu Lys Glu Glu
            100                 105                 110
Glu Thr Glu Ala Trp Gly Val Glu Pro Tyr Asp Leu Glu Asp Val Asp
            115                 120                 125
Gly Asn Cys Lys Ser Leu Val Asn Lys Gly Ile Val Arg Ala Ala Asp
130                 135                 140
Ile Lys Phe Pro Leu Pro Tyr Arg Ala Lys Ser Phe Ser Leu Val Ile
145                 150                 155                 160
Val Ser Asp Ala Leu Asp Tyr Leu Ser Pro Lys Tyr Leu Asn Arg Thr
                165                 170                 175
Leu Pro Glu Leu Ala Arg Val Ser Ala Asp Gly Val Ile Ile Phe Ser
            180                 185                 190
Gly Tyr Pro Gly Gln Gln Arg Ala Lys Val Ala Glu Leu Ser Lys Phe
            195                 200                 205
Gly Arg Pro Ala Lys Leu Arg Ser Ser Trp Trp Ile Arg Phe Phe
210                 215                 220
Val Gln Thr Ser Leu Glu Glu Asn Glu Ser Ala Ser Lys Lys Phe Glu
225                 230                 235                 240
Gln Ala Ala Leu Lys Arg Ser Tyr Lys Pro Glu Cys Gln Val Phe His
                245                 250                 255
Leu Lys Ser Tyr His
            260

<210> SEQ ID NO 12
<211> LENGTH: 1163
<212> TYPE: DNA
<213> ORGANISM: Populus trichocarpa

<400> SEQUENCE: 12
ggatcaagca atcaatctct gggtctctcg ctcgctctcc caactagctt accatcaaaa      60
cagatagatc cagatcgcgc tttaaaagat ctccaacccc taaccctttc cactcgatct     120
ctcagtttga ttgtaggcag gcctcttttg ttttaggtta ataacagaaa atgtcgagg      180 aggccaggga atcctgccag acgtttggct gatggaggaa gtcttccttt tgctgggtcg     240
atgcattcta atcgcgttc gtcgccgtta ctatccattg gccttgttgt cgtgggcgcg      300
attcttctta ttggatactg ttacagtggc tcaggtgggc atatccacaa tagagaagct     360
ttaagtaaga cagaaggtgg tgtttcttgc acactagaag tccaaagagc gatacctttt     420
ctgaagaagg cttatggtga cagcatgcgt aaagtactgc atgtaggccc ggacacttgt     480
tctgcagtat caagcttatt aaaagaagag gataccgagg cctggggtgt ggagccatat     540
gacttagatg atgtgagtgc caactgcaag agtcttgtgc gcaaaggcct tgtgcgtgta     600
gctgatatca aatttcctct gccctaccgg ccaaaatcat tctctcttgt tatagtgtca     660
gatgcgttgg attacttgtc tccaaaatat ctcaacaaaa cacttccaga attggcaagg     720
gtgtctgctg atggcctagt tgtatttttct ggcgctccag gtcagcaaag agttaaagtt     780
gcagagttgt ctaagtttgg tcgtccggcc aaattccgga cctcaacatg gtggataagg     840
```

-continued

```
tactttgttc agactggttt acaagagaat gaatctgcct taaagaagtt tgagcaggcg      900
gcattgaaga agtcatataa gccagcctgc caagttttcc acctccagtc atatgattga      960
aagttttggt gtcataacat tttccattgc tctgtctgca aactggcaac aaaccatgcc     1020
aatgtaagct attttgtgga attacgttca tgttggttct tatcttgata cagtaaatct     1080
cttgatcatt atttattgag gaaagtaagc atgtatgaat tcacttccac tattctttat     1140
aagataagtt tttgcactct atc                                             1163
```

<210> SEQ ID NO 13
<211> LENGTH: 262
<212> TYPE: PRT
<213> ORGANISM: Populus trichocarpa

<400> SEQUENCE: 13

Met Ser Arg Arg Pro Gly Asn Pro Ala Arg Leu Ala Asp Gly Gly
1               5                   10                  15
Ser Leu Pro Phe Ala Gly Ser Met His Ser Lys Ser Arg Ser Ser Pro
            20                  25                  30
Leu Leu Ser Ile Gly Leu Val Val Gly Ala Ile Leu Leu Ile Gly
        35                  40                  45
Tyr Cys Tyr Ser Gly Ser Gly Gly His Ile Thr Asn Arg Glu Ala Leu
    50                  55                  60
Ser Lys Thr Glu Gly Gly Val Ser Cys Thr Leu Glu Val Gln Arg Ala
65                  70                  75                  80
Ile Pro Phe Leu Lys Lys Ala Tyr Gly Asp Ser Met Arg Lys Val Leu
                85                  90                  95
His Val Gly Pro Asp Thr Cys Ser Ala Val Ser Ser Leu Leu Lys Glu
            100                 105                 110
Glu Asp Thr Glu Ala Trp Gly Val Glu Pro Tyr Asp Leu Asp Asp Val
        115                 120                 125
Ser Ala Asn Cys Lys Ser Leu Val Arg Lys Gly Leu Val Arg Val Ala
    130                 135                 140
Asp Ile Lys Phe Pro Leu Pro Tyr Arg Pro Lys Ser Phe Ser Leu Val
145                 150                 155                 160
Ile Val Ser Asp Ala Leu Asp Tyr Leu Ser Pro Lys Tyr Leu Asn Lys
                165                 170                 175
Thr Leu Pro Glu Leu Ala Arg Val Ser Ala Asp Gly Leu Val Val Phe
            180                 185                 190
Ser Gly Ala Pro Gly Gln Gln Arg Val Lys Val Ala Glu Leu Ser Lys
        195                 200                 205
Phe Gly Arg Pro Ala Lys Phe Arg Thr Ser Thr Trp Trp Ile Arg Tyr
    210                 215                 220
Phe Val Gln Thr Gly Leu Gln Glu Asn Glu Ser Ala Leu Lys Lys Phe
225                 230                 235                 240
Glu Gln Ala Ala Leu Lys Lys Ser Tyr Lys Pro Ala Cys Gln Val Phe
                245                 250                 255
His Leu Gln Ser Tyr Asp
            260

<210> SEQ ID NO 14
<211> LENGTH: 747
<212> TYPE: DNA
<213> ORGANISM: Ricinus communis

<400> SEQUENCE: 14

```
atgtcaagga ggcaagttag ctccactcgt agatttgtgg acacaggaaa ttttcctttt      60
tcaggagcac ttcaagctaa atctcgttct tctcctttct tatctgttgc ccttatcctt     120
ctgggagcaa tccttcttat cgcctatgct tatggtggtc atggtgactt tcatgtacc     180 ctagaagtcc agagaaccat tcccctttta agaaagcat atggtgacag tatgcgcaag     240
gttttgcatg tgggccctga tacttgttca gtcgtctctc aattgttgaa agaagaagaa     300
actgaagcat ggggtgttga accatatgat atagaggatg cagatgcaaa ctgcaagaat     360
tctatccgta aaggcattgt tcgtgtcgct gatattaagt tccctctgcc ttacaggacg     420
aagtcattct ctcttgttat tgtgtcagat gcacttgatt acctatcccc aaaatacctg     480
aacaggacac ttccagagtt ggcaagggtg gctgctgatg gtcttgttat ttatgcaggt     540 tacccctggac aacagagagc taaagttgca gaattgtcta aatttggacg accggccaaa     600
atgaggagct cgtcctggtg ggttcggttt tttgtccaga caagcataga agaaaatgaa     660
actgctatga agaagtttga gcaggctata tccaagaagt catacaagcc aacctgccaa     720
gtgttccact tgaagccata ccattag                                         747
```

<210> SEQ ID NO 15
<211> LENGTH: 248
<212> TYPE: PRT
<213> ORGANISM: Ricinus communis

<400> SEQUENCE: 15

```
Met Ser Arg Arg Gln Val Ser Ser Thr Arg Arg Phe Val Asp Thr Gly
  1               5                  10                  15

Asn Phe Pro Phe Ser Gly Ala Leu Gln Ala Lys Ser Arg Ser Ser Pro
                 20                  25                  30

Phe Leu Ser Val Ala Leu Ile Leu Leu Gly Ala Ile Leu Leu Ile Ala
             35                  40                  45

Tyr Ala Tyr Gly Gly His Gly Asp Phe Ser Cys Thr Leu Glu Val Gln
 50                  55                  60

Arg Thr Ile Pro Leu Leu Lys Lys Ala Tyr Gly Asp Ser Met Arg Lys
 65                  70                  75                  80

Val Leu His Val Gly Pro Asp Thr Cys Ser Val Val Ser Gln Leu Leu
                 85                  90                  95

Lys Glu Glu Thr Glu Ala Trp Gly Val Pro Tyr Asp Ile Glu
            100                 105                 110

Asp Ala Asp Ala Asn Cys Lys Asn Ser Ile Arg Lys Gly Ile Val Arg
            115                 120                 125

Val Ala Asp Ile Lys Phe Pro Leu Pro Tyr Arg Thr Lys Ser Phe Ser
        130                 135                 140

Leu Val Ile Val Ser Asp Ala Leu Asp Tyr Leu Ser Pro Lys Tyr Leu
145                 150                 155                 160

Asn Arg Thr Leu Pro Glu Leu Ala Arg Val Ala Ala Asp Gly Leu Val
                165                 170                 175

Ile Tyr Ala Gly Tyr Pro Gly Gln Gln Arg Ala Lys Val Ala Glu Leu
            180                 185                 190

Ser Lys Phe Gly Arg Pro Ala Lys Met Arg Ser Ser Trp Trp Val
        195                 200                 205

Arg Phe Phe Val Gln Thr Ser Ile Glu Glu Asn Glu Thr Ala Met Lys
    210                 215                 220

Lys Phe Glu Gln Ala Ile Ser Lys Lys Ser Tyr Lys Pro Thr Cys Gln
225                 230                 235                 240
```

Val Phe His Leu Lys Pro Tyr His
            245

<210> SEQ ID NO 16
<211> LENGTH: 1179
<212> TYPE: DNA
<213> ORGANISM: Glycine max

<400> SEQUENCE: 16

| | | | | |
|---|---|---|---|---|
| gagagtctgt tcggtcaca gcagagcaga gagtagtaag aagacactgc acagatctga | | | | 60 |
| gtggtgactg aaggaatcta gcttctttca tttctcatca ctattcttag gtctgagggc | | | | 120 |
| tcattgccat tatcatgtca aggaggccag taaatccttc gcgtcggtta ggtgatggtg | | | | 180 |
| gaagtatacc atttgctgca tctatccggt ctaaatctca aaactctccc ctactatcta | | | | 240 |
| ttgggcttgt cattgtgggt gcaatccttc tgattggtta ttgttacagc aattcaggtg | | | | 300 |
| gagctagcgg tggtattaag gatgtaagta aacttgaagg tggtgcatca tgctcatcag | | | | 360 |
| aagtcctaca agcattgccc gttttgaaga aatcatatgg agacagtttg cacaaggttt | | | | 420 |
| tgcatgttgg ccctgactct tgttctgtgt tatctagttt gttagaagaa gaggatactg | | | | 480 |
| aggcttgggg aatagaacca tatgagttag atgatgttgg tgcaaagtgt aaaagtcttg | | | | 540 |
| tacgcaaggg cattgtgcgt gtggctgatt tgaagttttc tctaccctac cgtgcaaagt | | | | 600 |
| cattttctct ggttattgtg tcagatgcat tggattactt atctccaaga tacctgaata | | | | 660 |
| aaaccctgcc agagttggtg agggtgtctg ctgatggtgt tgttatcttt gcaggttatc | | | | 720 |
| caggtcaaca gagaactaga ggtgaagaag tggccaaatt tggtcgtcca gccaaattgc | | | | 780 |
| gcagctcatc ttggtggata aggttttttcg ttcagtctag tttagatgaa atgaaactg | | | | 840 |
| ctggaaagaa gtttgaacag gcttcagcca agaaggcata caagccagca tgccaaattt | | | | 900 |
| ttcacctcaa atcatacccct gaaatttca ctgtcttatt tgtatactcc acttaatggt | | | | 960 |
| tagaagccat gctgatgaga taggcatctt cagcacccga agggtaaagt tccatatatg | | | | 1020 |
| ctgttgaaat tatagttcga tggtgatgac atattttatt tagattcaat tattaaacta | | | | 1080 |
| ttttgtctt ggatagtgtt cctcatgttt ttgtattcac aactgctatt tattatttag | | | | 1140 |
| aaaaatttct aatttgacac gaaaaaaaaa aaaaaaaaa | | | | 1179 |

<210> SEQ ID NO 17
<211> LENGTH: 262
<212> TYPE: PRT
<213> ORGANISM: Glycine max

<400> SEQUENCE: 17

Met Ser Arg Arg Pro Val Asn Pro Ser Arg Arg Leu Gly Asp Gly Gly
 1               5                  10                  15

Ser Ile Pro Phe Ala Ala Ser Ile Arg Ser Lys Ser Gln Asn Ser Pro
            20                  25                  30

Leu Leu Ser Ile Gly Leu Val Ile Val Gly Ala Ile Leu Leu Ile Gly
        35                  40                  45

Tyr Cys Tyr Ser Asn Ser Gly Gly Ala Ser Gly Gly Ile Lys Asp Val
    50                  55                  60

Ser Lys Leu Glu Gly Gly Ala Ser Cys Ser Ser Glu Val Leu Gln Ala
65                  70                  75                  80

Leu Pro Val Leu Lys Lys Ser Tyr Gly Asp Ser Leu His Lys Val Leu
                85                  90                  95

His Val Gly Pro Asp Ser Cys Ser Val Leu Ser Ser Leu Leu Glu Glu

```
                100                 105                 110
Glu Asp Thr Glu Ala Trp Gly Ile Glu Pro Tyr Glu Leu Asp Asp Val
            115                 120                 125

Gly Ala Lys Cys Lys Ser Leu Val Arg Lys Gly Ile Val Arg Val Ala
130                 135                 140

Asp Leu Lys Phe Ser Leu Pro Tyr Arg Ala Lys Ser Phe Ser Leu Val
145                 150                 155                 160

Ile Val Ser Asp Ala Leu Asp Tyr Leu Ser Pro Arg Tyr Leu Asn Lys
                165                 170                 175

Thr Leu Pro Glu Leu Val Arg Val Ser Ala Asp Gly Val Val Ile Phe
            180                 185                 190

Ala Gly Tyr Pro Gly Gln Gln Arg Thr Arg Gly Glu Glu Val Ala Lys
        195                 200                 205

Phe Gly Arg Pro Ala Lys Leu Arg Ser Ser Ser Trp Trp Ile Arg Phe
    210                 215                 220

Phe Val Gln Ser Ser Leu Asp Glu Asn Glu Thr Ala Gly Lys Lys Phe
225                 230                 235                 240

Glu Gln Ala Ser Ala Lys Lys Ala Tyr Lys Pro Ala Cys Gln Ile Phe
                245                 250                 255

His Leu Lys Ser Tyr Pro
            260
```

<210> SEQ ID NO 18
<211> LENGTH: 1124
<212> TYPE: DNA
<213> ORGANISM: Arabidopsis thaliana

<400> SEQUENCE: 18

```
gcgtttgaga gcagagcact cgataattaa cactagggac gaagaagctc tcgtttagta      60
aattttagct tagaacacag aagaagcatt ttttcggatc tgagatcttt agatccgaac     120
atcgtttatt tcaaatcgtt tattcaaggt ctaaaaaaaa gttttgaaga atcatagcca     180
tgtcaagaag gcaagtaagg cgtgtagggg atagtggaag cttcccattt gtaggagctc     240
tgcattcaaa atcacgttcg tctcctctgt tatcagtttg ccttgttctc gtgggagcat     300
gccttctcat tggttatgct tacagtggtc caggtatgtt caaaagtatc agagaagtca     360
gcaagattac aggtgactat tcttgcacag cagaagttca aagagccatt cctattctta     420
agagtgcgta tggagatagc atgcgcaaag tcctgcacgt gggtcctgaa acatgctcag     480
tggtctcgag tctgttgaat gaagaagaga cagaagcatg gggtgttgaa ccatatgatg     540
tggaggatgc agactctaac tgcaaaagtc ttttgcacaa gggccttgta cgtgtggctg     600
acatcaaatt ccctcttcct taccggtcaa agtcgttttc tcttgtgatc gtctcagacg     660
ctttggatta cctctcaccc aggtacctga caaaactgt gcctgaactt gctcgcgtcg     720
cttcagatgg tgtcgttctt ttagcaggta accctggtca acaaaaggct aaaggtgggg     780
aattgtcgaa atttggacgg cctgctaaaa tgcgtagctc gtcgtggtgg atccgtttct     840
tctcacagac gaacttagag gaaaacgaag cagcaagcaa gaaattcgaa caagcagctt     900
ccaagagttc atacaaacca gcttgtcaag ttttccacct caagccatta cattagtaca     960
cactattatt actggtctta agacatcaaa ccagatatct ctcctctctg tttaataccc    1020
tttttttccg ctatagaaag aaactaaact cccacaaatt gtaattcatt ctcaacgatt    1080
tgattcataa tttaactatt taataaattt gcctcttctc taca                     1124
```

<210> SEQ ID NO 19
<211> LENGTH: 258
<212> TYPE: PRT
<213> ORGANISM: Arabidopsis thaliana

<400> SEQUENCE: 19

Met Ser Arg Arg Gln Val Arg Val Gly Asp Ser Gly Ser Phe Pro
1               5                   10                  15

Phe Val Gly Ala Leu His Ser Lys Ser Arg Ser Pro Leu Leu Ser
                20                  25                  30

Val Cys Leu Val Leu Val Gly Ala Cys Leu Leu Ile Gly Tyr Ala Tyr
                35                  40                  45

Ser Gly Pro Gly Met Phe Lys Ser Ile Arg Glu Val Ser Lys Ile Thr
50                      55                  60

Gly Asp Tyr Ser Cys Thr Ala Glu Val Gln Arg Ala Ile Pro Ile Leu
65                  70                      75                  80

Lys Ser Ala Tyr Gly Asp Ser Met Arg Lys Val Leu His Val Gly Pro
                85                  90                  95

Glu Thr Cys Ser Val Val Ser Ser Leu Leu Asn Glu Glu Thr Glu
                100                 105                 110

Ala Trp Gly Val Glu Pro Tyr Asp Val Glu Asp Ala Asp Ser Asn Cys
                115                 120                 125

Lys Ser Leu Leu His Lys Gly Leu Val Arg Val Ala Asp Ile Lys Phe
130                 135                 140

Pro Leu Pro Tyr Arg Ser Lys Ser Phe Ser Leu Val Ile Val Ser Asp
145                 150                 155                 160

Ala Leu Asp Tyr Leu Ser Pro Arg Tyr Leu Asn Lys Thr Val Pro Glu
                165                 170                 175

Leu Ala Arg Val Ala Ser Asp Gly Val Val Leu Leu Ala Gly Asn Pro
                180                 185                 190

Gly Gln Gln Lys Ala Lys Gly Gly Glu Leu Ser Lys Phe Gly Arg Pro
                195                 200                 205

Ala Lys Met Arg Ser Ser Ser Trp Trp Ile Arg Phe Phe Ser Gln Thr
210                 215                 220

Asn Leu Glu Glu Asn Glu Ala Ala Ser Lys Lys Phe Glu Gln Ala Ala
225                 230                 235                 240

Ser Lys Ser Ser Tyr Lys Pro Ala Cys Gln Val Phe His Leu Lys Pro
                245                 250                 255

Leu His

<210> SEQ ID NO 20
<211> LENGTH: 1129
<212> TYPE: DNA
<213> ORGANISM: Arabidopsis lyrata

<400> SEQUENCE: 20
atattaacac ttcgaagctt cttcttcatt ttaagtaaat tcaagtggag gtgtttattc      60
ataaagtgct cattttctcg gatctcagat cttagatcca aaccctcttc gtttcattga     120
tccaagatct aatagcttga gcttgtgggg attttagtta tggcgagacg gcaagtaggt     180
tcaacaagac gtgtaggaga tggtggaagc ttcccgtttg caggagcttt gcattcaaag     240
tctcgatctt ctccactact ctctatttgc cttgttcttg tgggggcttg ccttctcatt     300
ggttatgctt acagtggtcc tggaatcttt aaaagtatca agaagtcag caaagttaca     360 ggtgactatt cttgcacagc agaagtccaa agagccattc ctgttcttaa gaaggcttat     420

```
ggagatggca tgcgcaaagt cttgcatgtg ggccctgaca catgctcagt ggtttccagt    480
ctactgaaag aagaagagac tgaagcatgg ggtgttgaac catatgacat cgaggatgca    540
gattctcact gcaagagttt tgtgagcaaa ggccttgtac gtgtggctga tatcaagttc    600
cctctgccct accgggcaaa atctttctct cttgtgattg tgtcagatgc tctggattat    660
ctctcaccca agtacctgaa caagactgtg cctgaactcg caagggtggc ttcagacggt    720
gttgttcttt ttgcaggtct ccctggtcag cagagagcta agttgctga actgtctaaa     780 tttggccgac ccgctaaaat gcgtagtgca tcgtggtgga accgcttttt cgtccagaca    840
aacttagaag aaaacgaagc accaagcaag aagttcgatc aggctgtttc caaaggatta    900
tacaaaccag cctgccaagt cttccacctc aagccattac attaaccagc caccaccaag    960
cctattgggt ccacaccaaa gcatatttac acgtagagcc gcacgcaaaa aaaaaaaata    1020
gcgtaatcga tattctcctt gtattttgta acaggtcagt ttttatcctt caatgttgta    1080
tccgtcaaca caattttttcc tattcaatta aatcataatt attatcacc              1129
```

<210> SEQ ID NO 21
<211> LENGTH: 261
<212> TYPE: PRT
<213> ORGANISM: Arabidopsis lyrata

<400> SEQUENCE: 21

Met Ala Arg Arg Gln Val Gly Ser Thr Arg Arg Val Gly Asp Gly Gly
1               5                   10                  15

Ser Phe Pro Phe Ala Gly Ala Leu His Ser Lys Ser Arg Ser Ser Pro
                20                  25                  30

Leu Leu Ser Ile Cys Leu Val Leu Val Gly Ala Cys Leu Leu Ile Gly
            35                  40                  45

Tyr Ala Tyr Ser Gly Pro Gly Ile Phe Lys Ser Ile Lys Glu Val Ser
        50                  55                  60

Lys Val Thr Gly Asp Tyr Ser Cys Thr Ala Glu Val Gln Arg Ala Ile
65                  70                  75                  80

Pro Val Leu Lys Lys Ala Tyr Gly Asp Gly Met Arg Lys Val Leu His
                85                  90                  95

Val Gly Pro Asp Thr Cys Ser Val Val Ser Ser Leu Leu Lys Glu Glu
            100                 105                 110

Glu Thr Glu Ala Trp Gly Val Glu Pro Tyr Asp Ile Glu Asp Ala Asp
        115                 120                 125

Ser His Cys Lys Ser Phe Val Ser Lys Gly Leu Val Arg Val Ala Asp
    130                 135                 140

Ile Lys Phe Pro Leu Pro Tyr Arg Ala Lys Ser Phe Ser Leu Val Ile
145                 150                 155                 160

Val Ser Asp Ala Leu Asp Tyr Leu Ser Pro Lys Tyr Leu Asn Lys Thr
                165                 170                 175

Val Pro Glu Leu Ala Arg Val Ala Ser Asp Gly Val Val Leu Phe Ala
            180                 185                 190

Gly Leu Pro Gly Gln Gln Arg Ala Lys Val Ala Glu Leu Ser Lys Phe
        195                 200                 205

Gly Arg Pro Ala Lys Met Arg Ser Ala Ser Trp Trp Asn Arg Phe Phe
    210                 215                 220

Val Gln Thr Asn Leu Glu Glu Asn Glu Ala Pro Ser Lys Lys Phe Asp
225                 230                 235                 240

Gln Ala Val Ser Lys Gly Leu Tyr Lys Pro Ala Cys Gln Val Phe His
                245                 250                 255

Leu Lys Pro Leu His
        260

<210> SEQ ID NO 22
<211> LENGTH: 1281
<212> TYPE: DNA
<213> ORGANISM: Solanum lycopersicum

<400> SEQUENCE: 22

```
aatctatggc ataaagttgg aggagttatt ttattttccc tctacagatt ccccaacaca      60
gacgacacag ttactactag caaaaccaaa ggaagcagat ccagatccca ccttcatcct     120
caagatctcg atctcacttc acactgattg ttcaacccag ttattactac ttgtcaatat     180
gtcaagaagg ccaactcgcc gctttgcaga tgctggtagt attccatttg tgggctcctt     240
gcaccccaaa tcacgtccat ctcctttatt gtccttagga cttgttttgg gtgcattgct     300
gatcattggt tacgtatatc atagttcagg tggaagaagt gcagcagatg cttttagtag     360
acttgaaggt ggtacttcat gcacagcgga gcttcacaga gcattacctg tactgaagaa     420
agcatatggg gataacatgc ggaaagtgtt gcacgtaggc cctgacactt gttcagtggt     480
ctctaatcta ttaaaagaag aggatactga agcttgggc attgaaccat atgatttaga     540
tgaaactgat agcaactgca aggctcttgt tcacaaaggg attgttcgag tagccgatgt     600
taaatttcct ctcccctacc gttcaaagtc gttctctcta gtcatagtat ctgatgcagt     660
ggattacttg tctccaagat accttaacaa actattccca gagttggcaa gggtggctgc     720
tgatggatta gttatttat ctggttaccc tggtcagcaa aaggttaaag gagcggagct     780
gtcaaaattt ggccggccag ccaaattgcg gagctcgtcc tggtggatta gattttcat     840
tcaaccagc ttagaagaga atgaacctgt aactaagaaa tttgaacaag cagcagccaa     900
gaggtcttac aagccagcct gccaagtttt ccacctcaag ccacttcttt gataataaaa     960
caccaactct gtttaaaaga tgcttagcgt cttcagctgt gtattaaatg acatgctcca    1020
agttctgaaa agttgacaat ttttgttgga ggaagttgtt tctgtatgat aggtttcaca    1080
agtaatgtat aataggctag gagcttgctg tcaattgata ttgctccttg taactgcaaa    1140
catagctggt tttagcatgt ccagaccaaa aacattgttt gagaattagt actgtataag    1200
ctaagatcaa taagtaattt atgatctttt tgctgtcata ttgtgtactc tctggttcat    1260
ctgaaattaa gtatctgttt a                                              1281
```

<210> SEQ ID NO 23
<211> LENGTH: 257
<212> TYPE: PRT
<213> ORGANISM: Solanum lycopersicum

<400> SEQUENCE: 23

Met Ser Arg Arg Pro Thr Arg Arg Phe Ala Asp Ala Gly Ser Ile Pro
1               5                   10                  15

Phe Val Gly Ser Leu His Pro Lys Ser Arg Pro Ser Pro Leu Leu Ser
            20                  25                  30

Leu Gly Leu Val Leu Gly Ala Leu Leu Ile Ile Gly Tyr Val Tyr His
        35                  40                  45

Ser Ser Gly Gly Arg Ser Ala Ala Asp Ala Phe Ser Arg Leu Glu Gly
    50                  55                  60

Gly Thr Ser Cys Thr Ala Glu Leu His Arg Ala Leu Pro Val Leu Lys
65                  70                  75                  80

```
Lys Ala Tyr Gly Asp Asn Met Arg Lys Val Leu His Val Gly Pro Asp
                 85                  90                  95

Thr Cys Ser Val Val Ser Asn Leu Leu Lys Glu Glu Asp Thr Glu Ala
            100                 105                 110

Trp Gly Ile Glu Pro Tyr Asp Leu Asp Glu Thr Asp Ser Asn Cys Lys
        115                 120                 125

Ala Leu Val His Lys Gly Ile Val Arg Val Ala Asp Val Lys Phe Pro
    130                 135                 140

Leu Pro Tyr Arg Ser Lys Ser Phe Ser Leu Val Ile Val Ser Asp Ala
145                 150                 155                 160

Val Asp Tyr Leu Ser Pro Arg Tyr Leu Asn Lys Thr Ile Pro Glu Leu
                165                 170                 175

Ala Arg Val Ala Ala Asp Gly Leu Val Ile Leu Ser Gly Tyr Pro Gly
            180                 185                 190

Gln Gln Lys Val Lys Gly Ala Glu Leu Ser Lys Phe Gly Arg Pro Ala
        195                 200                 205

Lys Leu Arg Ser Ser Ser Trp Trp Ile Arg Phe Phe Ile Gln Thr Ser
    210                 215                 220

Leu Glu Glu Asn Glu Pro Val Thr Lys Lys Phe Glu Gln Ala Ala Ala
225                 230                 235                 240

Lys Arg Ser Tyr Lys Pro Ala Cys Gln Val Phe His Leu Lys Pro Leu
                245                 250                 255

Leu

<210> SEQ ID NO 24
<211> LENGTH: 261
<212> TYPE: PRT
<213> ORGANISM: Prunus persica

<400> SEQUENCE: 24

Met Ser Arg Arg Pro Val Asn Pro Ala Arg Ile Gly Asp Gly Gly
1               5                   10                  15

Ser Ile Pro Phe Val Gly Val Val Gln Ser Lys Ala Arg Ser Ser Pro
                20                  25                  30

Leu Leu Ser Ile Gly Leu Val Leu Val Gly Ala Ile Leu Leu Val Cys
            35                  40                  45

Tyr Ala Phe Ser Gly Ser Gly Gly Arg Ser Ser Lys Glu Ala Val Ile
    50                  55                  60

Lys Leu Glu Gly Gly Ala Ser Cys Thr Phe Glu Val Gln Arg Ala Ile
65                  70                  75                  80

Pro Ile Leu Lys Lys Ala Tyr Gly Asp Ser Met Lys Lys Val Leu His
                85                  90                  95

Val Gly Pro Asp Thr Cys Ser Val Ser Lys Leu Leu Lys Glu Glu
            100                 105                 110

Asp Thr Glu Ala Trp Gly Val Glu Pro Phe Asp Leu Glu Asp Ala Asp
        115                 120                 125

Ala Asn Cys Lys Ser Leu Val Ser Lys Gly Ile Val Arg Ala Ala Asp
    130                 135                 140

Ile Lys Phe Ser Leu Pro Tyr Arg Pro Lys Ser Phe Ser Leu Val Ile
145                 150                 155                 160

Ala Ser Asp Ala Leu Asp Tyr Leu Ser Pro Lys Tyr Leu Asn Lys Thr
                165                 170                 175

Leu Pro Glu Leu Ala Arg Val Ser Ala Asp Gly Val Val Ile Phe Thr
            180                 185                 190
```

```
Gly Tyr Pro Gly Gln His Lys Ala Lys Val Ala Glu Leu Ser Lys Phe
            195                 200                 205

Gly Arg Pro Ala Lys Leu Arg Ser Ser Ser Trp Trp Ile Arg Tyr Phe
210                 215                 220

Val Gln Thr Ser Leu Glu Glu Asn Glu Val Ala Ser Lys Lys Phe Glu
225                 230                 235                 240

Gln Ala Ala Leu Lys Lys Ser Tyr Thr Pro Ala Cys Gln Val Phe His
            245                 250                 255

Leu Lys Ser Tyr His
            260
```

<210> SEQ ID NO 25
<211> LENGTH: 684
<212> TYPE: PRT
<213> ORGANISM: Arabidopsis thaliana

<400> SEQUENCE: 25

```
Met Ser Met Pro Leu Gln Arg Gly Ile Ser Gly Val Arg Val Ser Asp
1               5                   10                  15

Ser Ser Asp Asp Leu Arg Asp Ser Gln Met Lys Asp Lys Thr Glu Arg
                20                  25                  30

Ala Arg Ser Thr Glu Asn Asn Asn Leu Thr Leu Arg Phe Pro Phe Gly
            35                  40                  45

Phe Leu Phe Ser Asn Gln Ser Ser Lys His Gly Gly Gly Gly Gly Glu
    50                  55                  60

Asn Gly Phe Ser Ala Asp Pro Tyr Ser Ala Arg Ser Arg His Arg Leu
65                  70                  75                  80

Met Leu Leu Phe Leu Lys Ile Ser Leu Val Leu Ile Val Val Ile Ala
                85                  90                  95

Leu Ala Gly Ser Phe Trp Trp Thr Ile Ser Ile Ser Thr Ser Ser Arg
            100                 105                 110

Gly His Val Tyr His Asn Tyr Arg Arg Leu Gln Glu Gln Leu Val Ser
        115                 120                 125

Asp Leu Trp Asp Ile Gly Glu Ile Ser Leu Gly Pro Asn Arg Trp Lys
    130                 135                 140

Glu Leu Glu Tyr Cys Asn Ile Glu Ser Glu Asn Phe Val Pro Cys Phe
145                 150                 155                 160

Asn Val Ser Glu Asn Leu Ala Leu Gly Tyr Ser Asn Gly Asp Glu Asn
                165                 170                 175

Asp Arg Phe Cys Gly Pro Gly Ser Lys Gln Glu Cys Leu Glu Leu Pro
            180                 185                 190

Pro Val Lys Tyr Arg Val Pro Leu Arg Trp Pro Thr Gly Lys Asp Ile
        195                 200                 205

Ile Trp His Ser Asn Val Lys Ile Thr Ala Gln Glu Val Val Ser Ser
    210                 215                 220

Gly Ser Ile Thr Lys Arg Met Met Met Glu Asp Asp Gln Ile Ser
225                 230                 235                 240

Phe Arg Ser Ala Ser Pro Met Ser Asp Glu Val Asp Tyr Ser His
                245                 250                 255

Gln Ile Ala Glu Met Ile Gly Ile Lys Lys Asp Asn Phe Ile Glu Ala
            260                 265                 270

Gly Val Arg Thr Ile Leu Asp Ile Gly Cys Gly Tyr Gly Ser Phe Gly
        275                 280                 285

Ala His Leu Leu Ser Lys Gln Ile Leu Thr Met Cys Ile Ala Asn Tyr
    290                 295                 300
```

Glu Ala Ser Gly Ser Gln Val Gln Leu Thr Leu Glu Arg Gly Leu Pro
305                 310                 315                 320

Ala Met Ile Gly Ser Phe Ile Ser Lys Gln Leu Pro Tyr Pro Ser Leu
            325                 330                 335

Ser Phe Asp Met Leu His Cys Leu Arg Cys Gly Ile Asp Trp Asp Gln
            340                 345                 350

Lys Asp Gly Leu Leu Leu Val Glu Ile Asp Arg Val Leu Lys Pro Gly
            355                 360                 365

Gly Tyr Phe Val Trp Thr Ser Pro Leu Thr Asn Pro Arg Asn Lys Asp
            370                 375                 380

His Leu Lys Arg Trp Asn Phe Val His Asp Phe Ala Glu Ser Ile Cys
385                 390                 395                 400

Trp Thr Leu Leu Asn Gln Gln Asp Glu Thr Val Val Trp Lys Lys Thr
                405                 410                 415

Ile Asn Thr Lys Cys Tyr Ser Ser Arg Lys Pro Gly Val Gly Pro Ser
                420                 425                 430

Val Cys Thr Lys Gly His Asp Val Glu Ser Pro Tyr Tyr Arg Pro Leu
            435                 440                 445

Gln Met Cys Ile Gly Gly Thr Arg Ser Arg Trp Ile Pro Ile Glu
    450                 455                 460

Gly Arg Thr Arg Trp Pro Ser Arg Ser Asn Met Asn Lys Thr Glu Leu
465                 470                 475                 480

Ser Leu Tyr Gly Leu His Pro Glu Val Leu Gly Glu Asp Ala Glu Asn
                485                 490                 495

Trp Lys Ile Thr Val Arg Glu Tyr Trp Ser Leu Leu Ser Pro Leu Ile
                500                 505                 510

Phe Ser Asp His Pro Lys Arg Pro Gly Asp Glu Asp Pro Ser Pro Pro
            515                 520                 525

Tyr Asn Met Leu Arg Asn Val Leu Asp Met Asn Ala Gln Phe Gly Gly
            530                 535                 540

Leu Asn Ser Ala Leu Leu Glu Ala Arg Lys Ser Val Trp Val Met Asn
545                 550                 555                 560

Val Val Pro Thr Ala Gly Pro Asn His Leu Pro Met Ile Leu Asp Arg
                565                 570                 575

Gly Phe Val Gly Val Leu His Asn Trp Cys Glu Pro Phe Pro Thr Tyr
                580                 585                 590

Pro Arg Thr Tyr Asp Leu Val His Ala Asp Asn Leu Leu Ser Leu Gln
            595                 600                 605

Thr Ser Gln Pro Arg Lys Thr Cys Leu Leu Ile Asp Ile Phe Thr Glu
            610                 615                 620

Ile Asp Arg Leu Leu Arg Pro Glu Gly Trp Val Ile Ile Arg Asp Thr
625                 630                 635                 640

Ala Gln Leu Val Glu Lys Ala Arg Glu Thr Ile Thr Gln Leu Lys Trp
            645                 650                 655

Glu Ala Arg Val Ile Glu Val Glu Ser Ser Glu Gln Arg Leu Leu
            660                 665                 670

Ile Cys Gln Lys Pro Phe Thr Lys Arg Gln Ser Ile
            675                 680

<210> SEQ ID NO 26
<211> LENGTH: 208
<212> TYPE: PRT
<213> ORGANISM: Arabidopsis thaliana

<400> SEQUENCE: 26

Pro Gly Ile Phe Lys Ser Ile Lys Glu Val Ser Lys Val Thr Gly Asp
1               5                   10                  15

Tyr Ser Cys Thr Ala Glu Val Gln Arg Ala Ile Pro Val Leu Lys Lys
            20                  25                  30

Ala Tyr Gly Asp Gly Met Arg Lys Val Leu His Val Gly Pro Asp Thr
        35                  40                  45

Cys Ser Val Val Ser Ser Leu Leu Lys Glu Glu Thr Glu Ala Trp
    50                  55                  60

Gly Val Glu Pro Tyr Asp Ile Glu Asp Ala Asp Ser His Cys Lys Ser
65              70                  75                  80

Phe Val Ser Lys Gly Leu Val Arg Val Ala Asp Ile Lys Phe Pro Leu
                85                  90                  95

Pro Tyr Arg Ala Lys Ser Phe Ser Leu Val Ile Val Ser Asp Ala Leu
            100                 105                 110

Asp Tyr Leu Ser Pro Lys Tyr Leu Asn Lys Thr Val Pro Glu Leu Ala
        115                 120                 125

Arg Val Ala Ser Asp Gly Val Val Leu Phe Ala Gly Leu Pro Gly Gln
    130                 135                 140

Gln Arg Ala Lys Val Ala Glu Leu Ser Lys Phe Gly Arg Pro Ala Lys
145                 150                 155                 160

Met Arg Ser Ala Ser Trp Trp Asn Arg Phe Phe Val Gln Thr Asn Leu
                165                 170                 175

Glu Glu Asn Asp Ala Pro Ser Lys Lys Phe Glu Gln Ala Val Ser Lys
            180                 185                 190

Gly Leu Tyr Lys Pro Ala Cys Gln Val Phe His Leu Lys Pro Leu His
        195                 200                 205

<210> SEQ ID NO 27
<211> LENGTH: 206
<212> TYPE: PRT
<213> ORGANISM: Arabidopsis thaliana

<400> SEQUENCE: 27

Met Phe Lys Ser Ile Arg Glu Val Ser Lys Ile Thr Gly Asp Tyr Ser
1               5                   10                  15

Cys Thr Ala Glu Val Gln Arg Ala Ile Pro Ile Leu Lys Ser Ala Tyr
            20                  25                  30

Gly Asp Ser Met Arg Lys Val Leu His Val Gly Pro Glu Thr Cys Ser
        35                  40                  45

Val Val Ser Ser Leu Leu Asn Glu Glu Thr Glu Ala Trp Gly Val
    50                  55                  60

Glu Pro Tyr Asp Val Glu Asp Ala Asp Ser Asn Cys Lys Ser Leu Leu
65              70                  75                  80

His Lys Gly Leu Val Arg Val Ala Asp Ile Lys Phe Pro Leu Pro Tyr
                85                  90                  95

Arg Ser Lys Ser Phe Ser Leu Val Ile Val Ser Asp Ala Leu Asp Tyr
            100                 105                 110

Leu Ser Pro Arg Tyr Leu Asn Lys Thr Val Pro Glu Leu Ala Arg Val
        115                 120                 125

Ala Ser Asp Gly Val Val Leu Leu Ala Gly Asn Pro Gly Gln Gln Lys
    130                 135                 140

Ala Lys Gly Gly Glu Leu Ser Lys Phe Gly Arg Pro Ala Lys Met Arg
145                 150                 155                 160

```
Ser Ser Ser Trp Trp Ile Arg Phe Phe Ser Gln Thr Asn Leu Glu Glu
                165                 170                 175

Asn Glu Ala Ala Ser Lys Lys Phe Glu Gln Ala Ser Lys Ser Ser
            180                 185                 190

Tyr Lys Pro Ala Cys Gln Val Phe His Leu Lys Pro Leu His
        195                 200                 205

<210> SEQ ID NO 28
<211> LENGTH: 580
<212> TYPE: PRT
<213> ORGANISM: Arabidopsis thaliana

<400> SEQUENCE: 28

Ile Ser Ile Ser Thr Ser Ser Arg Gly His Val Tyr His Asn Tyr Arg
1               5                   10                  15

Arg Leu Gln Glu Gln Leu Val Ser Asp Leu Trp Asp Ile Gly Glu Ile
            20                  25                  30

Ser Leu Gly Pro Asn Arg Trp Lys Glu Leu Glu Tyr Cys Asn Ile Glu
        35                  40                  45

Ser Glu Asn Phe Val Pro Cys Phe Asn Val Ser Glu Asn Leu Ala Leu
    50                  55                  60

Gly Tyr Ser Asn Gly Asp Glu Asn Asp Arg Phe Cys Gly Pro Gly Ser
65              70                  75                  80

Lys Gln Glu Cys Leu Glu Leu Pro Pro Val Lys Tyr Arg Val Pro Leu
                85                  90                  95

Arg Trp Pro Thr Gly Lys Asp Ile Ile Trp His Ser Asn Val Lys Ile
            100                 105                 110

Thr Ala Gln Glu Val Val Ser Ser Gly Ser Ile Thr Lys Arg Met Met
        115                 120                 125

Met Met Glu Asp Asp Gln Ile Ser Phe Arg Ser Ala Ser Pro Met Ser
    130                 135                 140

Asp Glu Val Glu Asp Tyr Ser His Gln Ile Ala Glu Met Ile Gly Ile
145             150                 155                 160

Lys Lys Asp Asn Phe Ile Glu Ala Gly Val Arg Thr Ile Leu Asp Ile
                165                 170                 175

Gly Cys Gly Tyr Gly Ser Phe Gly Ala His Leu Leu Ser Lys Gln Ile
            180                 185                 190

Leu Thr Met Cys Ile Ala Asn Tyr Glu Ala Ser Gly Ser Gln Val Gln
        195                 200                 205

Leu Thr Leu Glu Arg Gly Leu Pro Ala Met Ile Gly Ser Phe Ile Ser
    210                 215                 220

Lys Gln Leu Pro Tyr Pro Ser Leu Ser Phe Asp Met Leu His Cys Leu
225             230                 235                 240

Arg Cys Gly Ile Asp Trp Asp Gln Lys Asp Gly Leu Leu Leu Val Glu
                245                 250                 255

Ile Asp Arg Val Leu Lys Pro Gly Gly Tyr Phe Val Trp Thr Ser Pro
            260                 265                 270

Leu Thr Asn Pro Arg Asn Lys Asp His Leu Lys Arg Trp Asn Phe Val
        275                 280                 285

His Asp Phe Ala Glu Ser Ile Cys Trp Thr Leu Leu Asn Gln Gln Asp
    290                 295                 300

Glu Thr Val Val Trp Lys Lys Thr Ile Asn Thr Lys Cys Tyr Ser Ser
305             310                 315                 320

Arg Lys Pro Gly Val Gly Pro Ser Val Cys Thr Lys Gly His Asp Val
                325                 330                 335
```

-continued

Glu Ser Pro Tyr Tyr Arg Pro Leu Gln Met Cys Ile Gly Gly Thr Arg
              340                 345                 350

Ser Arg Arg Trp Ile Pro Ile Glu Gly Arg Thr Arg Trp Pro Ser Arg
          355                 360                 365

Ser Asn Met Asn Lys Thr Glu Leu Ser Leu Tyr Gly Leu His Pro Glu
      370                 375                 380

Val Leu Gly Glu Asp Ala Glu Asn Trp Lys Ile Thr Val Arg Glu Tyr
385                 390                 395                 400

Trp Ser Leu Leu Ser Pro Leu Ile Phe Ser Asp His Pro Lys Arg Pro
              405                 410                 415

Gly Asp Glu Asp Pro Ser Pro Tyr Asn Met Leu Arg Asn Val Leu
          420                 425                 430

Asp Met Asn Ala Gln Phe Gly Gly Leu Asn Ser Ala Leu Leu Glu Ala
      435                 440                 445

Arg Lys Ser Val Trp Val Met Asn Val Val Pro Thr Ala Gly Pro Asn
450                 455                 460

His Leu Pro Met Ile Leu Asp Arg Gly Phe Val Gly Val Leu His Asn
465                 470                 475                 480

Trp Cys Glu Pro Phe Pro Thr Tyr Pro Arg Thr Tyr Asp Leu Val His
              485                 490                 495

Ala Asp Asn Leu Leu Ser Leu Gln Thr Ser Gln Pro Arg Lys Thr Cys
          500                 505                 510

Leu Leu Ile Asp Ile Phe Thr Glu Ile Asp Arg Leu Leu Arg Pro Glu
      515                 520                 525

Gly Trp Val Ile Ile Arg Asp Thr Ala Gln Leu Val Glu Lys Ala Arg
530                 535                 540

Glu Thr Ile Thr Gln Leu Lys Trp Glu Ala Arg Val Ile Glu Val Glu
545                 550                 555                 560

Ser Ser Ser Glu Gln Arg Leu Leu Ile Cys Gln Lys Pro Phe Thr Lys
              565                 570                 575

Arg Gln Ser Ile
          580

<210> SEQ ID NO 29
<211> LENGTH: 46
<212> TYPE: DNA
<213> ORGANISM: Artificial Sequence
<220> FEATURE:
<223> OTHER INFORMATION: A synthetic oligonucleotide

<400> SEQUENCE: 29
gagaacctgt acttccaggg tatggcgaga cggcaagtag gttcaa        46

<210> SEQ ID NO 30
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 30
catgacccct gcaggctaat gtaatggctt gaggtgga        38

<210> SEQ ID NO 31
<211> LENGTH: 51
<212> TYPE: DNA
<213> ORGANISM: Artificial Sequence
<220> FEATURE:

<223> OTHER INFORMATION: A synthetic oligonucleotide

<400> SEQUENCE: 31
gagaacctgt acttccaggg tatgttcaaa agtatcagag aagtcagcaa g        51

<210> SEQ ID NO 32
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 32 catgaccct gcaggctaat gtaatggctt gaggtgga        38

<210> SEQ ID NO 33
<211> LENGTH: 50
<212> TYPE: DNA
<213> ORGANISM: Artificial Sequence
<220> FEATURE:
<223> OTHER INFORMATION: A synthetic oligonucleotide

<400> SEQUENCE: 33
gagaacctgt acttccaggg tatgatttcc atttcgactt cttccagagg        50

<210> SEQ ID NO 34
<211> LENGTH: 40
<212> TYPE: DNA
<213> ORGANISM: Artificial Sequence
<220> FEATURE:
<223> OTHER INFORMATION: A synthetic oligonucleotide

<400> SEQUENCE: 34 catgaccct gcaggtcaga ttgattgtcg cttggtgaat        40

<210> SEQ ID NO 35
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 35
tttcattgct tcaaagatgg c        21

<210> SEQ ID NO 36
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 36
gaggatgcag attctcactg c        21

<210> SEQ ID NO 37
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 37
atattgacca tcatactcat tgc        23

<210> SEQ ID NO 38
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 38
aggacgtcta gatggcgaga cggcaagtag gttcaac                                37

<210> SEQ ID NO 39
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 39
catgaccgtc gacttatgta atggcttgag gtggaagac                              39

<210> SEQ ID NO 40
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 40
caggacgtct agatgtcaag aaggcaagta aggcg                                  35

<210> SEQ ID NO 41
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 41
catgaccgtc gacttatgta atggcttgag gtggaaaac                              39

<210> SEQ ID NO 42
<211> LENGTH: 29
<212> TYPE: DNA
<213> ORGANISM: Artificial Sequence
<220> FEATURE:
<223> OTHER INFORMATION: A synthetic oligonucleotide

<400> SEQUENCE: 42
tcaattctct ctaccgtgat caagatgca                                         29

<210> SEQ ID NO 43
<211> LENGTH: 28
<212> TYPE: DNA
<213> ORGANISM: Artificial Sequence
<220> FEATURE:
<223> OTHER INFORMATION: A synthetic oligonucleotide

<400> SEQUENCE: 43
ggtgtcagaa ctctccacct caagagta                                          28

<210> SEQ ID NO 44
<211> LENGTH: 20
<212> TYPE: DNA
<213> ORGANISM: Artificial Sequence
<220> FEATURE:
<223> OTHER INFORMATION: A synthetic oligonucleotide

```
<400> SEQUENCE: 44
caaaccagcc tgccaagtct                                              20

<210> SEQ ID NO 45
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 45
tggtgtggaa ccagtaggct tt                                           22

<210> SEQ ID NO 46
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 46
caaagtcgtt ttctcttgtg atcgt                                        25

<210> SEQ ID NO 47
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 47
tcaggcacag ttttgttcag gta                                          23

<210> SEQ ID NO 48
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 48
tgtcggagtt ttgcacaact g                                            21

<210> SEQ ID NO 49
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 49
tgtctgcatg taccaggtca tatg                                         24

<210> SEQ ID NO 50
<211> LENGTH: 25
<212> TYPE: DNA
<213> ORGANISM: Artificial Sequence
<220> FEATURE:
<223> OTHER INFORMATION: A synthetic oligonucleotide

<400> SEQUENCE: 50
cgcttcgttt ttattatctg tgctt                                        25

<210> SEQ ID NO 51
<211> LENGTH: 24
```

```
<212> TYPE: DNA
<213> ORGANISM: Artificial Sequence
<220> FEATURE:
<223> OTHER INFORMATION: A synthetic oligonucleotide

<400> SEQUENCE: 51
tcgcagaact gcactaaaca gagt                                          24

<210> SEQ ID NO 52
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 52
caggacgtct agatggcgag acggcaagta ggttcaac                           38

<210> SEQ ID NO 53
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 53
catgaccgtc gacttatgta atggcttgag gtggaagac                          39

<210> SEQ ID NO 54
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 54
caggacgtct agatgtcaag aaggcaagta aggcg                              35

<210> SEQ ID NO 55
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 55
catgaccgtc gacttatgta atggcttgag gtggaaaac                          39
```